(12) United States Patent
Sacherman et al.

(10) Patent No.: US 11,273,295 B2
(45) Date of Patent: Mar. 15, 2022

(54) INNER EAR DRUG DELIVERY DEVICES AND METHODS OF USE

(71) Applicant: Spiral Therapeutics, Inc., Brisbane, CA (US)

(72) Inventors: Kevin W. Sacherman, Brisbane, CA (US); Signe Erickson, Brisbane, CA (US); Hugo Peris, Brisbane, CA (US); Eugene de Juan, Jr., Brisbane, CA (US)

(73) Assignee: SPIRAL THERAPEUTICS, INC., South San Francisco, CA (US)

( * ) Notice: Subject to any disclaimer, the term of this patent is extended or adjusted under 35 U.S.C. 154(b) by 295 days.

(21) Appl. No.: 16/388,159

(22) Filed: Apr. 18, 2019

(65) Prior Publication Data

US 2019/0321611 A1     Oct. 24, 2019

Related U.S. Application Data

(60) Provisional application No. 62/660,163, filed on Apr. 19, 2018.

(51) Int. Cl.
*A61M 31/00* (2006.01)
*A61M 37/00* (2006.01)

(52) U.S. Cl.
CPC .......... *A61M 31/002* (2013.01); *A61M 37/00* (2013.01); *A61M 2205/04* (2013.01); *A61M 2210/0662* (2013.01)

(58) Field of Classification Search
CPC ................ A61M 31/002; A61M 37/00; A61M 2205/04; A61M 2210/0662; A61F 11/00
See application file for complete search history.

(56) References Cited

U.S. PATENT DOCUMENTS 5,421,818 A * 6/1995 Arenberg ................ A61F 11/00
                                                604/20
5,895,372 A * 4/1999 Zenner ................ A61M 5/1428
                                                604/93.01
(Continued)

FOREIGN PATENT DOCUMENTS

CA      2740877 A1    4/2010
CA      2743252 A1    5/2010
(Continued)

OTHER PUBLICATIONS

PCT International Preliminary Report on Patentability in International Appln. No. PCT/US2019/028189, dated Oct. 29, 2020, 11 pages.

(Continued)

*Primary Examiner* — Bradley J Osinski
(74) *Attorney, Agent, or Firm* — Fish & Richardson P.C.

(57) ABSTRACT

An implantable device for delivering a therapeutic agent to treat an ear of a patient includes a body having a distal end region and a proximal end region. The body defines, at least in part, a reservoir configured to contain the therapeutic agent. The device includes a shaft attached to the distal end region of the body and a lumen extending through the shaft having at least one inlet at a proximal end region in fluid communication with the reservoir and at least one outlet at a distal end region. Upon implantation of the body in a region of the ear, a length of the shaft is sufficient to extend from the body to at least the round window membrane of the ear. The device is configured to deliver the therapeutic agent to the ear from the reservoir via passive diffusion. Related devices and methods are described.

13 Claims, 39 Drawing Sheets

(56) References Cited

U.S. PATENT DOCUMENTS

| | | | |
|---|---|---|---|
| 6,120,484 A * | 9/2000 | Silverstein | A61F 11/00 424/427 |
| 6,156,728 A | 12/2000 | Gao | |
| 6,377,849 B1 | 4/2002 | Lenarz et al. | |
| 6,440,102 B1 | 8/2002 | Arenberg et al. | |
| 6,589,286 B1 | 7/2003 | Litner | |
| 6,648,873 B2 | 11/2003 | Arenberg et al. | |
| 6,685,697 B1 * | 2/2004 | Arenberg | A61F 11/00 604/11 |
| 7,044,942 B2 | 5/2006 | Jolly et al. | |
| 7,571,012 B2 | 8/2009 | Gibson | |
| 7,589,110 B2 | 9/2009 | Puel et al. | |
| 7,803,148 B2 | 9/2010 | Lobl et al. | |
| 8,197,461 B1 | 6/2012 | Arenberg et al. | |
| 8,224,417 B2 | 7/2012 | Vetter | |
| 8,267,905 B2 | 9/2012 | Lobl et al. | |
| 8,271,101 B2 | 9/2012 | Overstreet et al. | |
| 8,298,176 B2 | 10/2012 | Lobl et al. | |
| 8,399,006 B2 | 3/2013 | de Juan, Jr et al. | |
| 8,515,560 B2 | 8/2013 | Debruyne et al. | |
| 8,750,988 B2 | 6/2014 | Jolly et al. | |
| 8,876,795 B2 | 11/2014 | Fiering et al. | |
| 9,040,701 B2 | 5/2015 | Messeguer Peypoch et al. | |
| 9,050,444 B2 | 6/2015 | Gharib et al. | |
| 9,352,136 B2 | 5/2016 | Gharib et al. | |
| 9,616,207 B2 | 4/2017 | Verhoeven et al. | |
| 9,764,121 B2 | 9/2017 | Fiering et al. | |
| 2006/0287689 A1 | 12/2006 | Debruyne et al. | |
| 2007/0160648 A1 | 7/2007 | Ashton et al. | |
| 2009/0028923 A1 | 1/2009 | Muni et al. | |
| 2010/0106134 A1 | 4/2010 | Jolly et al. | |
| 2010/0121422 A1 | 5/2010 | Jolly et al. | |
| 2013/0245569 A1 * | 9/2013 | Jolly | A61N 1/0541 604/265 |
| 2015/0044271 A1 | 2/2015 | Slattery et al. | |
| 2018/0221208 A1 | 8/2018 | Goldfarb et al. | |

FOREIGN PATENT DOCUMENTS

| | | |
|---|---|---|
| WO | WO-00/33775 A1 | 6/2000 |
| WO | WO-02/100318 A2 | 12/2002 |
| WO | WO-2017/160948 A1 | 9/2017 |
| WO | WO-2017/203397 A1 | 11/2017 |
| WO | WO-2018/027102 A1 | 2/2018 |

OTHER PUBLICATIONS

PCT International Search Report and Written Opinion in International Appln. No. PCT/US2019/028189, dated Sep. 16, 2019, 15 pages.

"Drug Delivery—Inner Ear," (Mar. 14, 2012) InCube Labs, LLC, Webpage. Wayback Machine. Web. Jul. 17, 2019. 1 page.

"Novel Drug Delivery Device for Inner Ear Disorders Heads to Preclinical Test, Prompts Formation of Industry Consortium," (Nov. 6, 2017) Draper.com, 5 pages. Web. Jul. 12, 2019.

Ayoob, A.M. et al. (2014) "The role of intracochlear drug delivery devices in the management of inner ear disease," *Expert Opin. Drug Deliv.*, [Early Online] 12(3), 15 pages.

Columbia Technology Ventures (Apr. 27, 2015) "Minimally invasive inner ear fluid aspirator for diagnosis and treatment," Overview. Columbia University in the City of New York. New York, New York. Reference: IR CU15244. Web. Jul. 12, 2019. 2 pages. http://innovation.columbia.edu/technologies/CU15244_minimally-invasive-inner-ear-fluid%20/.

Columbia Technology Ventures (Dec. 3, 2012) "Tool for controlled drug delivery into the inner earthat avoids cochlea injury and preserves hearing," Overview. Columbia University in the City of New York. New York, New York. Reference: IR CU13136. Web. Jul. 12, 2019. 2 pages. http://innovation.columbia.edu/technologies/CU13136_tool-for-controlled-drug-delivery%20/.

Columbia Technology Ventures (Jan. 28, 2016) "Microneedle sensor for precise monitoring of membrane penetration," Overview. Columbia University in the City of New York. New York, New York. Reference: IR CU16194. Web. Jul. 12, 2019. 2 pages. http://innovation.columbia.edu/technologies/CU16194_microneedle-sensor-for-precise.

Columbia Technology Ventures (Jul. 7, 2014) "Single needle perforation of the round window membrane to facilitate cochlear implantation," Overview. Columbia University in the City of New York. New York, New York. Reference: IR CU15002. Web. Jul. 12, 2019. 2 pages. http://innovation.columbia.edu/technologies/CU15002_single-needle-perforation-of-the%20/.

Hochmair, I. et al. (2006). "MED-EL Cochlear Implants: State of the Art and a Glimpse Into the Future," *Trends In Amplification*, 10(4), 201-219. doi:10.1177/1084713806296720.

Nguyen, K. et al. (2017) "Recent advances in therapeutics and drug delivery for the treatment of inner ear diseases: a patent review (2011-2015)," *Expert Opinion on Therapeutic Patents*, vol. 27(2):191-202, DOI: 10.1080/13543776.2017.1252751. (Published online: Nov. 18, 2016).

Peppi, M et al. (2018) "Intracochlear drug delivery systems: a novel approach whose time has come," *Expert Opinion on Drug Delivery*, 15:4, 319-324, DOI: 10.1080/17425247.2018.1444026.

Plontke, S.K. et al. (2014) "Controlled Release Dexamethasone Implants in the Round Window Niche for Salvage Treatment of Idiopathic Sudden Sensorineural Hearing Loss," *Otology & Neurotology*. 35(7): 1168-1171.

Richard, C. et al. (2012) "Round Window Versus Cochleostomy Technique in Cochlear Implantation: Histologic Findings," *Otology & Neurotology*, 33(7), 1181-1187. doi:10.1097/MAO. 0b013e318263d56d.

\* cited by examiner

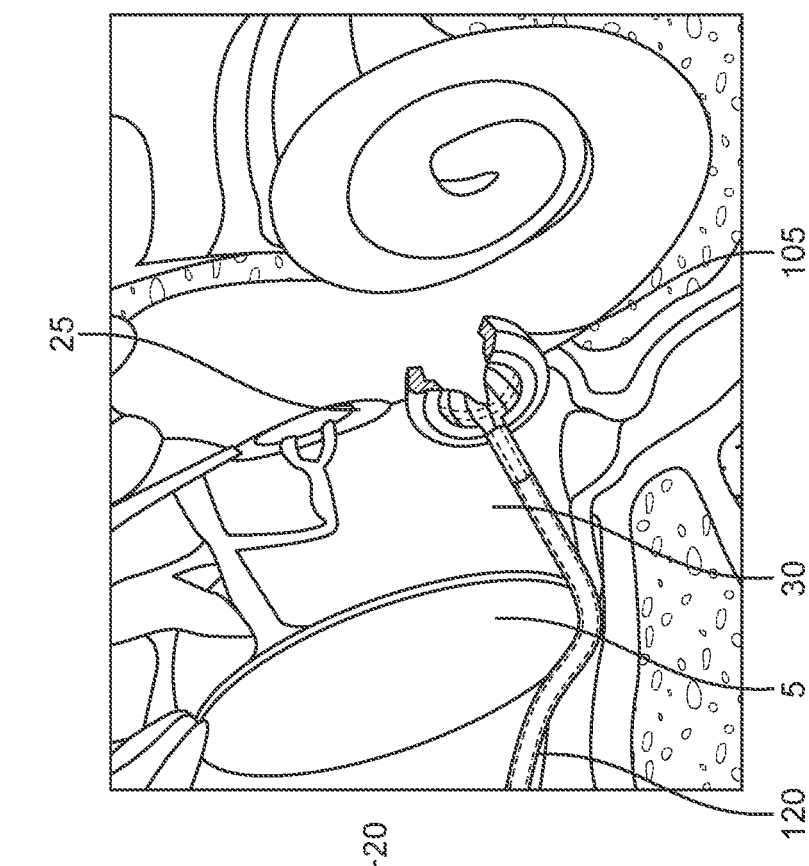
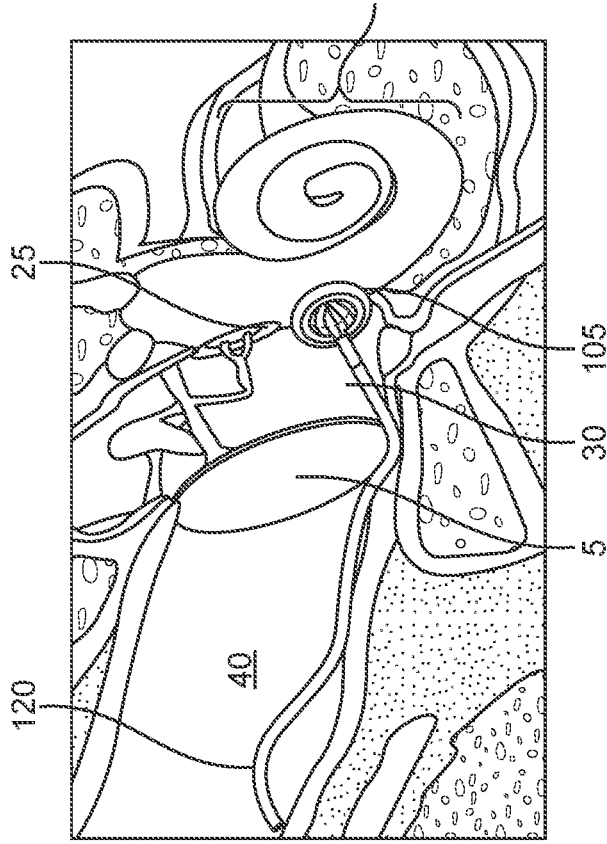
FIG. 10B
FIG. 10A

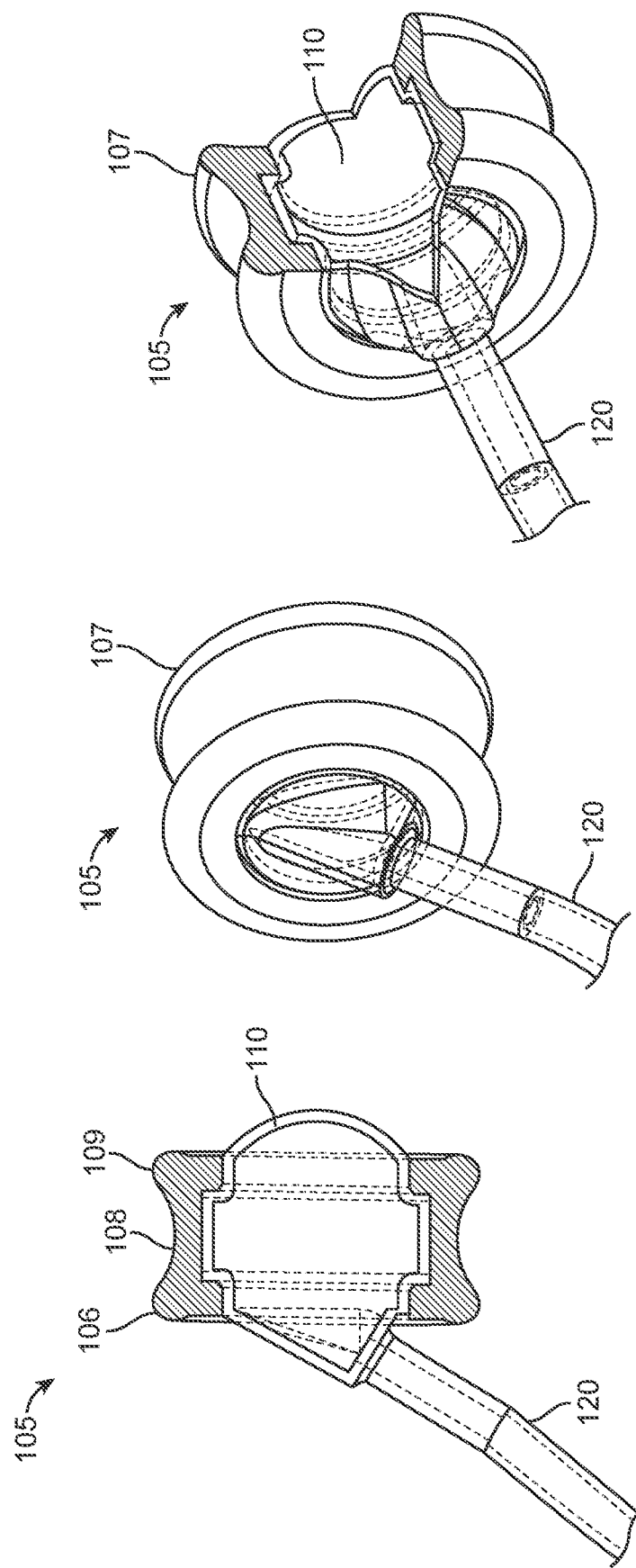

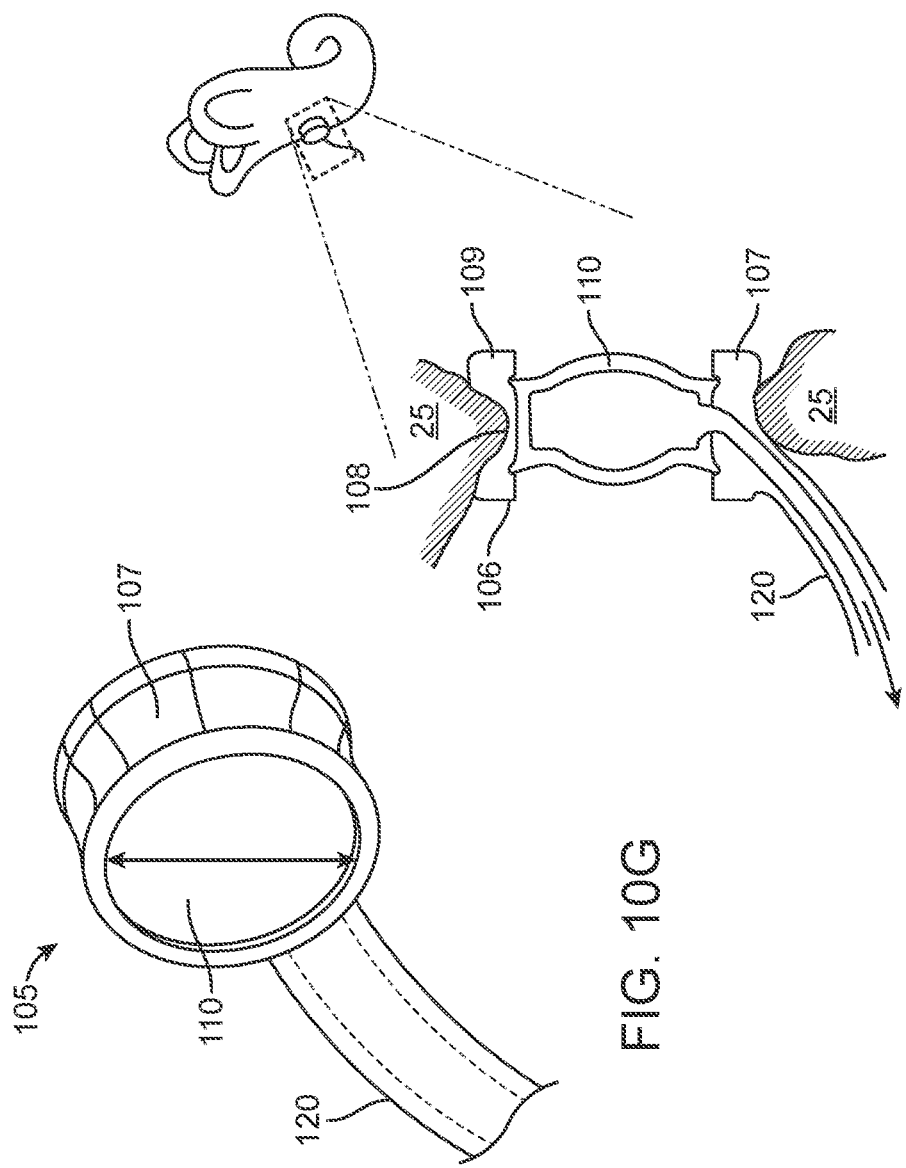

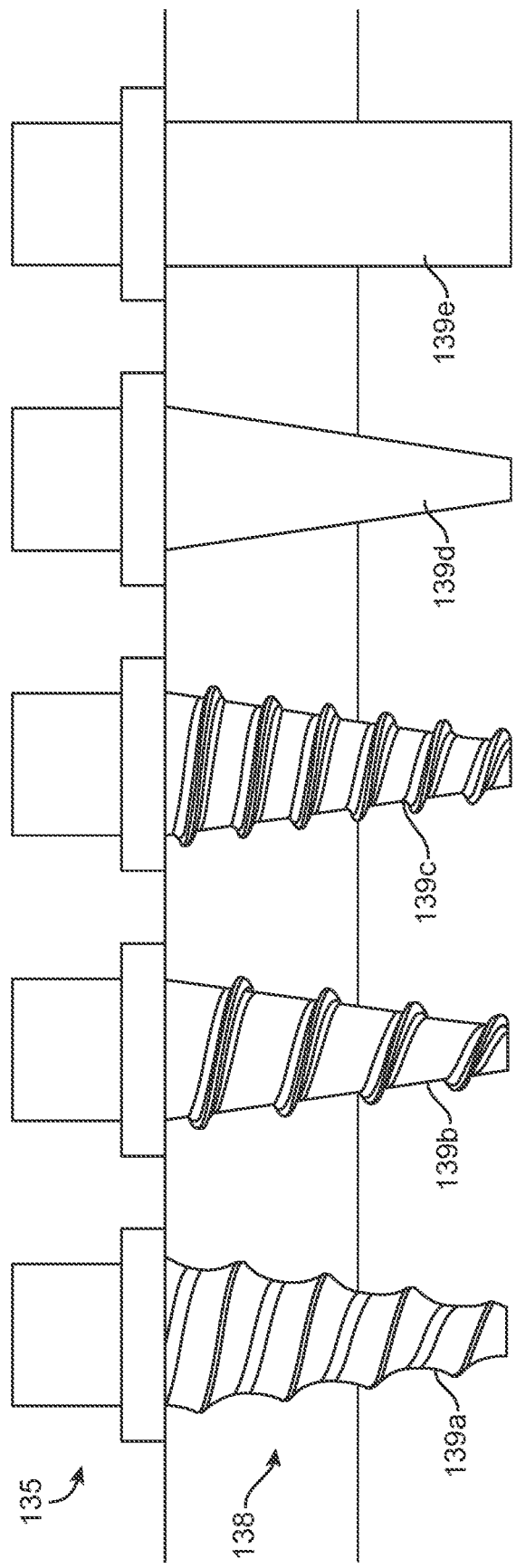

INNER EAR DRUG DELIVERY DEVICES
AND METHODS OF USE

CROSS-REFERENCE TO PRIORITY
DOCUMENT

This application claims the benefit of priority under 35 U.S.C. § 119(e) of U.S. provisional patent application Ser. No. 62/660,163, filed Apr. 19, 2018. The disclosure of the provisional patent application is hereby incorporated by reference in its entirety.

BACKGROUND

When the ear is functioning normally, sound waves travel through the air to the outer ear, which collects the sound and directs it through the ear canal to the middle ear. The sound waves strike the eardrum, or tympanic membrane, and cause it to vibrate. This vibration is transmitted to the cochlea by the middle ear bones, called ossicles. The three ossicles that comprise the ossicular chain are termed the malleus, incus and stapes, but are also commonly referred to as the "hammer", "anvil" and "stirrup", respectively. Motion of these bones, transmits sound pressure waves arriving at the eardrum to the cochlea's oval window membrane, which in turn, gives rise to a travelling displacement wave within the cochlea.

The inner ear consists of the bony labyrinth, a system of passages making up the following two main functional parts: 1) the cochlea, which is dedicated to hearing, and 2) the vestibular system, which is dedicated to balance. The cochlea is lined with thousands of tiny sensory receptors, commonly referred to as hair cells, that are arranged in rows along the basilar membrane. As the basilar membrane vibrates in response to incoming pressure waves, the hair cells transduce this mechanical motion into electrical impulses that result in neurotransmitter release and excitation of the auditory neurons. Afferent signaling from the auditory neurons is then processed and transmitted by a series of neural connections all the way to the cortex, where sound is perceived.

Hearing loss is the most common sensory impairment in humans, affecting over 5% of individuals in industrialized nations. It is also an important health problem in the elderly, and 40% of the population aged 65 years or older have a hearing loss great enough to impair communication.

Hearing loss can be a result of a variety of auditory disorders. Conductive Hearing Loss (CHL) involves the loss of normal mechanical pathways for sound to reach the hair cells in the cochlea, for example by anatomical malformations/anomalies, ear infections, allergies, tumors, bone remodeling, and/or damage to the ossicles. Sensorineural Hearing Loss (SNHL) is due to impaired ability of the cochlea to effectively transduce pressure waves into neural signaling. SNHL is typically associated with exposure to loud noise, aging, head trauma, exposure to ototoxic drugs, infection, autoimmune disease, Meniere's disease, genetic mutations, tumors of the auditory nerve and the like.

Although new therapies to treat hearing loss are emerging, there is a need for safe, direct, efficient and effective drug delivery devices. Methods capable of providing long-term drug delivery for sustained therapeutic effect in treating hearing loss and other maladies of the ear represent unmet medical needs. These needs are particularly pronounced for ailments affecting the inner ear including areas in and around the cochlea, semicircular canals, vestibule for example.

SUMMARY

In an implementation, described is an implantable device for delivering a therapeutic agent to treat an ear of a patient. The device includes a body having a distal end region and a proximal end region. The body defines, at least in part, a reservoir configured to contain the therapeutic agent. The device includes a shaft attached to the distal end region of the body and has a lumen extending through the shaft. The lumen has at least one inlet at a proximal end region of the shaft in fluid communication with the reservoir and at least one outlet at a distal end region of the shaft. The shaft has a length between the proximal end region and the distal end region. Upon implantation of the body in a region of the ear, the length of the shaft is sufficient to extend from the body to at least the round window membrane of the ear. The device is configured to deliver the therapeutic agent to the ear from the reservoir via passive diffusion.

The body may be sized to be implanted in a tympanic cavity or in a mastoid cavity of a middle ear of the patient or in an ear canal of the patient. The reservoir may have a volume of about 5 uL to about 1 mL. The device may further include an access port into the reservoir. A re-sealable penetrable barrier may be positioned within the access port that is configured to be penetrated for refilling of the reservoir with therapeutic agent. The device may further include a porous drug release element positioned relative to at least one of the inlet and the outlet from the lumen of the shaft. The body may be rigid or compliant. The therapeutic agent may include corticosteroids, aminoglycosides, antimicrobials, antifungals, antivirals, non-steroidal anti-inflammatories, decongestants, anticholinesterases, mydriatics, sypathomimetics, antineoplastics, immunological drugs, hormonal agents, beta adrenergic blockers, growth factors, anhysrase inhibitors, prostaglandins, antiprostaglandins, prostaglandin precursors, antioxidants, NMDA receptor antagonists, nootropics, anti-apoptotic agents, neurotrophins, neuroprotective agents, cannabinoids, monoclonal antibodies, gene therapies, cell therapies, and inhibitors of APAF-1.

The shaft may be configured to extend through the round window membrane. The device may further include an annular anchor having an outer surface and an inner surface. The outer surface may be configured to seal against a perimeter of a round window membrane and the inner surface may encircle a first segment of the distal end region of the shaft extending through the annular anchor. The shaft may further include a second segment located immediately proximal to the first segment. The second segment may have a distensible wall.

The device may further include a porous drug release element positioned within the lumen of the shaft proximal to the second segment. The porous drug release element may be configured to control the passive diffusion through the first segment of the shaft. Upon implantation of the device, the first segment of the shaft may be in contact with a liquid environment of a cochlea of the ear and the shaft proximal to the first segment may be in contact with air of a middle ear of the patient. Upon implantation of the device, the porous drug release element may dampen a pressure wave from the cochlea and shunt the pressure wave to the distensible wall of the second segment. Upon implantation of the device, the distensible wall of the second segment may interface with air of the middle ear. The annular anchor may be formed of a conformable material or of a semi-rigid material.

The device may further include an annular anchor having an outer ring surface configured to seal against a perimeter of a round window membrane and an inner ring surface. The anchor may include a channel extending through the annular anchor from a proximal surface of the annular anchor to a distal surface of the annular anchor. The channel may have an inner diameter configured to receive an outer diameter of at least the distal end region of the shaft. The anchor may include a distensible membrane coupled to a distal side of the annular anchor. The anchor may include a rigid plate coupled to a proximal side of the annular anchor opposite the distensible membrane. A chamber may be located within the annular anchor and defined collectively by the inner ring surface, an inner surface of the rigid plate, and an inner surface of the distensible membrane. The length of the shaft may provide the passive diffusion. Upon implantation of the device, the chamber may be filled with air and the distal surface of the distensible membrane may be surrounded by perilymph. The distensible membrane may provide acoustic impedance similar to an acoustic impedance of the round window membrane.

The device may further include an annular anchor having an outer ring surface configured to seal against a perimeter of a round window membrane and an inner ring surface. A first distensible membrane may be coupled to a proximal side of the annular anchor. A second distensible membrane may be coupled to a distal side of the annular anchor opposite the first distensible membrane. The first distensible membrane may be non-permeable to the therapeutic agent and the second distensible membrane may be permeable to the therapeutic agent or both the first and second distensible membranes may be permeable to the therapeutic agent. The annular anchor may include a chamber located within the annular anchor defined collectively by the inner ring surface, an inner surface of the first distensible membrane, and an inner surface of the second distensible membrane. The at least one outlet at the distal end region of the shaft may be positioned in fluid communication with the chamber. The therapeutic agent may passively diffuse through at least one of the first distensible membrane and the second distensible membrane.

In an interrelated implementation, disclosed is an implantable device for delivering a therapeutic agent to treat an ear of a patient. The device includes a body having a distal end region and a proximal end region. The body is configured to be implanted in a cavity of a middle ear of the patient. The body defines, at least in part, a reservoir configured to contain the therapeutic agent. The device further includes a shaft attached to the distal end region of the body. A lumen extends through the shaft and the lumen has at least one inlet at a proximal end region of the shaft in fluid communication with the reservoir and at least one outlet at a distal end region of the shaft. When the body is implanted in the cavity, the shaft extends through a wall of the cavity and the at least one outlet is positioned into a cochlear space. A helical threadform is on an outer surface of the shaft that is configured to cut through and linearly advance into the wall upon rotation. The device is configured to deliver the therapeutic agent from the reservoir via passive diffusion through the at least one outlet of the shaft into the perilymph of the cochlear space.

The shaft may be configured to substantially anchor and seal the device within the wall. The helical thread-form on the shaft may be a self-tapping thread-form. The shaft may be tapered distally. The shaft may have a longitudinal axis that is coaxial with a longitudinal axis of the device. The internal lumen may have a longitudinal axis that is off-set from the longitudinal axis of the shaft. The device may further include a porous drug release element positioned relative to at least one of the inlet and the outlet from the lumen of the shaft. The device may further include an access port into the reservoir and a resealable penetrable barrier positioned within the access port that is configured to be penetrated for refilling of the reservoir with therapeutic agent. The body may be rigid or compliant. The therapeutic agent includes antimicrobials, antifungals, antivirals, nonsteroidal anti-inflammatories, decongestants, anticholinesterases, mydriatics, sypathomimetics, antineoplastics, immunological drugs, hormonal agents, beta adrenergic blockers, growth factors, anhydrase inhibitors, prostaglandins, antiprostaglandins, prostaglandin precursors, antioxidants, NMDA receptor antagonists, nootropics, anti-apoptotic agents, neurotrophins, neuroprotective agents, cannabinoids, monoclonal antibodies, gene therapies, and inhibitors of APAF-1. The reservoir may have a volume of about 5 uL to about 1 mL. The cavity may include the mastoid cavity or the tympanic cavity. The cavity may be the tympanic cavity and the wall may be a medial wall of the tympanic cavity.

Other features and advantages will be apparent from the following description of various implementations, which illustrate, by way of example, the principles of the disclosed devices and methods.

BRIEF DESCRIPTION OF THE DRAWINGS

These and other aspects will now be described in detail with reference to the following drawings. Generally speaking, the figures are not to scale in absolute terms or comparatively but are intended to be illustrative. Also, relative placement of features and elements may be modified for the purpose of illustrative clarity.

FIGS. 10A-10H show various views of an implementation of an implanted portion of a drug delivery device.

FIGS. 15A-15H show implementations of implanted portions having an anchoring feature configured to anchor the device of FIG. 14.

DETAILED DESCRIPTION

Figure 1:
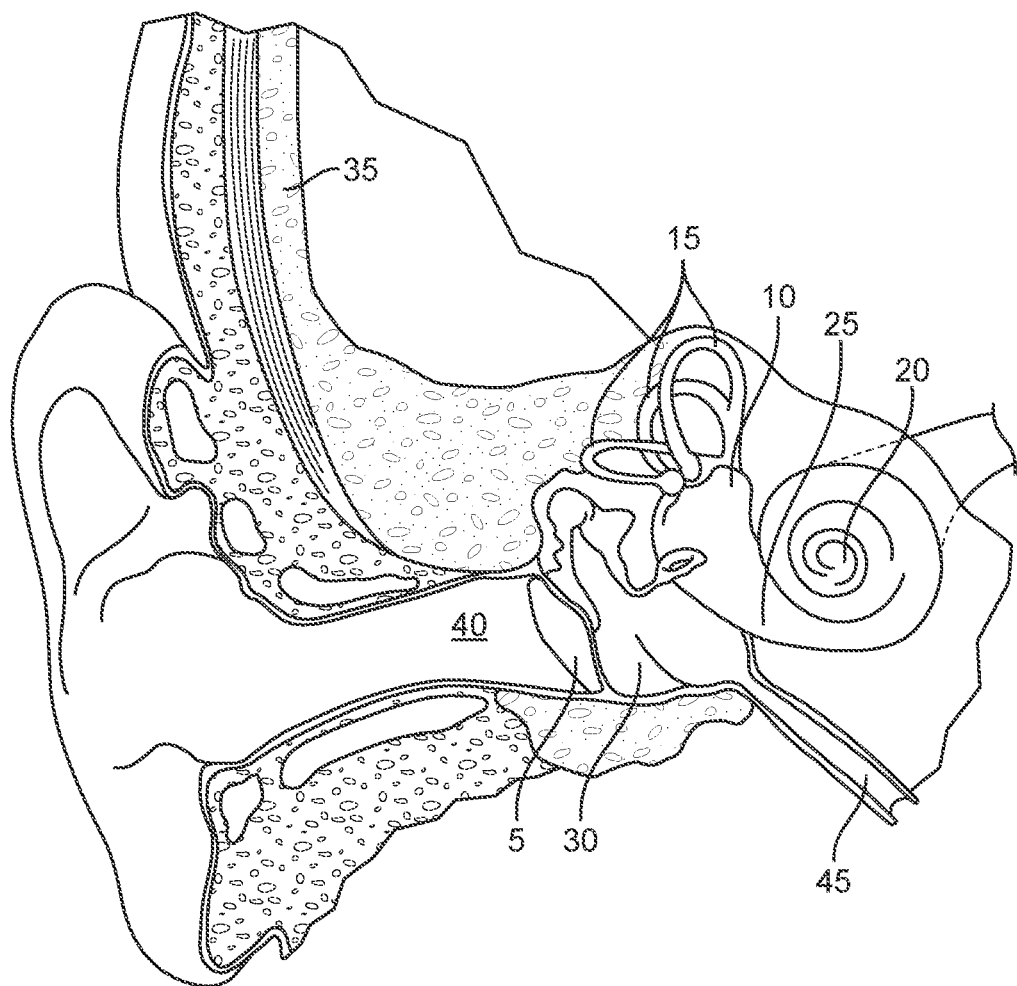
FIG. 1 diagrammatically shows the anatomy of an ear in a coronal section view.

Conductive Hearing Loss (CHL) involves the loss of normal mechanical pathways for sound to reach the hair cells in the cochlea, for example by anatomical malformations/anomalies, ear infections, allergies, tumors, bone remodeling, and/or damage to the ossicles. Sensorineural Hearing Loss (SNHL) is due to impaired ability of the cochlea to effectively transduce pressure waves into neural signaling. SNHL is typically associated with exposure to loud noise, aging, head trauma, exposure to ototoxic drugs, infection, autoimmune disease, Meniere's disease, genetic mutations, tumors of the auditory nerve, and the like.

Treatment of SNHL, depending on the cause, can include drug treatments for hair cell and cochlear nerve afferents regeneration, reversal of cochlear oxidative stress damage, and apoptosis inhibition. There are several drugs in the final stages of clinical development for the treatment of hearing loss including STS (Fennec Pharmaceuticals) to protect against cisplatin-induced hearing loss; AM-101 (Auris Medical) for the treatment of tinnitus; AM-111 (Auris Medical) for otoprotection in acute inner ear hearing loss; OTO-104 (Otonomy) for the treatment of Meniere's Disease; SPI-1005 (Sound Pharmaceuticals) for the treatment of mild to moderate acute noise-induced hearing loss and for the treatment of Meniere's Disease.

However, the inner ear presents a unique and delicate anatomy that is difficult to treat effectively. For example, the presence of the blood-cochlear barrier (BCB) limits access of many of these compounds to the inner ear. Thus systemic administration, oral, intravenous, and intramuscular routes often require high doses and/or result in systemic side effects. Local drug delivery methods are also known. For example, inner ear therapy (e.g. drugs formulated as biocompatible gels) can be delivered to the middle ear via intra-tympanic injections across the tympanic membrane (TM), which are subsequently absorbed into the cochlea through the round and oval window membranes.

Local drug delivery to the inner ear using osmotic pumps or infusion pump is also known. For example, implantable and programmable intracochlear micropumps known in the art can provide targeted, controllable, and extended drug delivery. However, the pumps require precise micromechanical pumping technology in order to maintain a constant fluid volume and can increase the risk of damage to the inner ear due to malfunctions or delivery of too much fluid. Additionally, some pumps like osmotic pumps include reservoirs that are incapable of being refilled, which requires the entire pump to be replaced. Similarly, electronic pumps are dependent upon power and require batteries and/or recharging of the power.

Regardless of the delivery method (i.e. local delivery via injections or pumping), the therapeutic effect achieved by the drug is limited by the clearance and distribution (pharmacokinetics) of the drug within the fluids of the inner ear.

Described herein are drug delivery devices and systems capable of providing long-term (i.e. extended) drug levels for sustained, site-specific, controlled or other modified therapeutic agent(s) released for treating hearing loss and other maladies of the ear. The drug delivery devices and systems can be passive systems in that drug delivery is achieved without active pumping and/or without fluid flow. The drug delivery devices and systems described herein incorporate passive diffusion and capillary action to provide drug delivery. It should be appreciated that the devices and systems described herein can be positioned in many locations of the ear and need not be implanted specifically as shown in the figures or as described herein. The devices and systems described herein can be used to deliver therapeutic agent(s) for an extended period of time from a body that defines, at least in part, a reservoir to one or more of the following tissues: round window membrane, cochlea, hair cells of the cochlea, and other tissues of the middle and inner ear. Although specific reference is made below to the delivery of treatments to the ear, it also should be appreciated that medical conditions besides these conditions can be treated with the devices and systems described herein. For example, the devices and systems can deliver treatments for inflammation, infection, and cancerous growths. Any number of drug combinations can be delivered using any of the devices and systems described herein.

The materials, compounds, compositions, articles, and methods described herein may be understood more readily by reference to the following detailed description of specific aspects of the disclosed subject matter and the examples included therein. Before the present materials, compounds, compositions, articles, devices, and methods are disclosed and described, it is to be understood that the aspects described below are not limited to specific methods or specific reagents, as such may vary. It is also to be understood that the terminology used herein is for the purpose of describing particular aspects only and is not intended to be limiting.

Unless defined otherwise, all technical and scientific terms used herein have the same meaning as is commonly understood by one of ordinary skill in the art. All patents, patent applications, published applications and publications, websites and other published materials referred to throughout the entire disclosure herein, unless noted otherwise, are incorporated by reference in their entirety. In the event that there are pluralities of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, relative directional terms such as anterior, posterior, proximal, distal, lateral, medial, sagittal, coronal, transverse, etc. are used throughout this disclosure. Such terminology is for purposes of describing devices and features of the devices and is not intended to be limited. For example, as used herein "proximal" generally means closest to a user implanting a device and farthest from the target location of implantation, while "distal" means farthest from the user implanting a device in a patient and closest to the target location of implantation.

As used herein, a disease or disorder refers to a pathological condition in an organism resulting from, for example, infection or genetic defect, and characterized by identifiable symptoms.

As used herein, treatment means any manner in which the symptoms of a condition, disorder or disease are ameliorated or otherwise beneficially altered. Treatment also encompasses any pharmaceutical use of the devices described and provided herein.

As used herein, amelioration or alleviation of the symptoms of a particular disorder, such as by administration of a particular pharmaceutical composition, refers to any lessening, whether permanent or temporary, lasting or transient that can be attributed to or associated with administration of the composition.

As used herein, an effective amount of a compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

Pharmaceutically effective amount, therapeutically effective amount, biologically effective amount and therapeutic amount are used interchangeably herein to refer to an amount of a therapeutic that is sufficient to achieve a desired result, (i.e. therapeutic effect, whether quantitative or qualitative). In particular, a pharmaceutically effective amount, in vivo, is that amount that results in the reduction, delay, or elimination of undesirable effects (such as pathological, clinical, biochemical and the like) in the subject.

As used herein, a subject includes any animal for whom diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

As used herein, a therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body. As used herein, sustained release encompasses release of effective amounts of an active ingredient of a therapeutic agent for an extended period of time. The sustained release may encompass first order release of the active ingredient, zero order release of the active ingredient, or other kinetics of release such as intermediate to zero order and first order, or combinations thereof. The sustained release may encompass controlled release of the therapeutic agent via passive molecular diffusion driven by a concentration gradient across a drug release element. The sustained release can generally include liquids, suspensions, emulsions, resins, or gels, for example.

As used herein, a composition refers to any mixture. It can be a solution, a suspension, an emulsion, liquid, powder, a paste, aqueous, non-aqueous or any combination of such ingredients.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination, optionally, including instructions for use of the combination and/or other reactions and components for such use.

Figure 5:
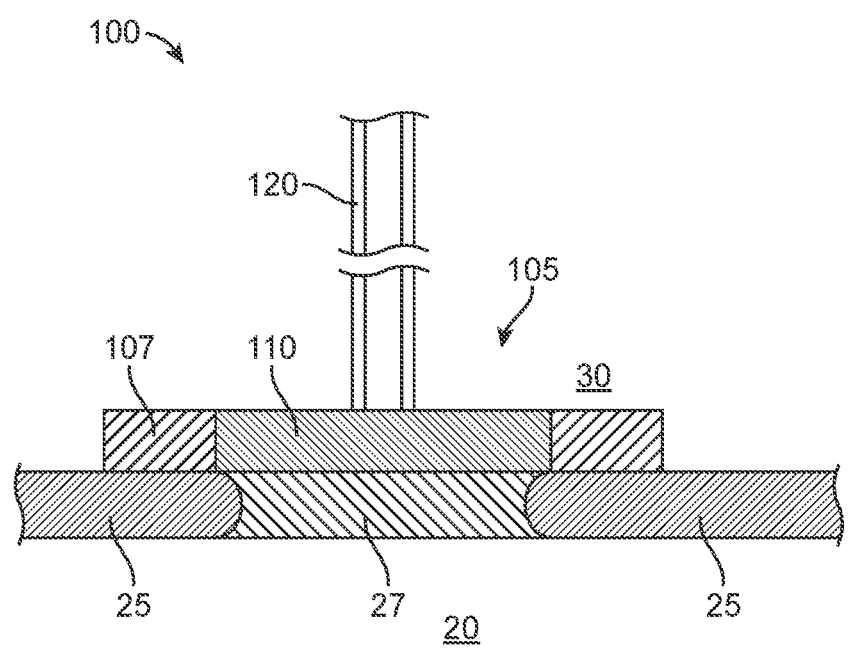
FIG. 5 shows an implementation of a drug delivery system in schematic implanted to deliver therapeutic agent to the round window membrane from a reservoir.

FIG. 1 shows the anatomy of an ear showing the outer ear, the middle ear, and the inner ear. The outer ear includes an auricle and an ear canal 40. The tympanic membrane 5 is disposed across the distal end of the ear canal 40 and provides a barrier between the outer ear and the middle ear. The vibration of the tympanic membrane 5 in response to sound waves is coupled to the oval window or fenestra ovalis, which is adjacent the round window niche 25, through the bones of the middle ear. The round window niche 25 includes a round window membrane 27 (see, for example, FIG. 5) that, in combination with the oval window of the cochlea, allow the fluid in the cochlea 20 to move. The bones of the middle ear include the malleus, the incus, and the stapes, which are collectively referred to as the ossicles. The ossicles are positioned in the middle ear cavity and serve to filter and amplify the sound wave causing the oval window to vibrate. The vibration of the oval window sets up waves of fluid motion of the perilymph within the cochlea 20. Such fluid motion, in turn, activates tiny hair cells inside the cochlea 20. Hair cells of the cochlea 20 are critical in transducing acoustic signals into nerve impulses. The hair cells, which help discern vibrations to assist in the process of hearing, are bathed in secreted fluids such as perilymph (at their basolateral surfaces facing the scala tympani) and endolymph (at their apical surfaces facing the scala media).

Activation of the hair cells in turn causes appropriate nerve impulses to be generated and transferred through the spiral ganglion cells and auditory nerve to the brain where they are perceived as sound. The semicircular canals 15 are three half-circular, interconnected tubes located adjacent the cochlea 20. The vestibule 10 provides fluid communication between the semicircular canals 15 and the cochlea 20. The three canals are the horizontal semicircular canal, the posterior semicircular canal, and the superior semicircular canal.

The devices and systems described herein are referred to as drug delivery devices, drug delivery systems, treatment devices, therapeutic devices, port delivery systems, implants, and the like. It should be appreciated that these terms are used interchangeably herein and are not intended to be limiting to a particular implementation of one device over another device. For the sake of brevity, explicit descriptions of each of those combinations may be omitted although the various combinations are to be considered herein. Additionally, described herein are different methods for implantation and access of the devices. The various implants can be implanted, filled, refilled, etc. according to a variety of different methods and using a variety of different devices and systems. Provided are some representative descriptions of how the various devices may be implanted and accessed, however, for the sake of brevity, explicit descriptions of each method with respect to each implant or system may be summarized or omitted.

The drug delivery devices described herein can deliver drug from a relatively small, self-contained system over an extended period of time by passive mechanisms such as those that involve no fluid flow, such as passive diffusion, or other passive mechanisms such as capillary action, for drug delivery. The devices described need not incorporate an active pumping element or rely upon electrical or mechanical drug delivery. Meaning, the reservoir of the drug delivery devices can be smaller in size even for the long-term, chronic delivery of drug, which given the relatively limited space in the middle ear, ear canal, or mastoid recess, is a distinct advantage. The reservoir can, but need not, be refillable as will be described in more detail below. The devices provide sufficient anchoring within the ear for the life of the device and minimally impact the acoustic impedance at the site of implantation. The devices described herein can incorporate an intracochlear portion and an extracochlear portion.

Described herein are implantable devices for delivering a therapeutic agent to treat an ear of a patient. The device is configured to deliver the therapeutic agent to the ear from the reservoir via passive diffusion. The device can include a body having a distal end region and a proximal end region. The body can define, at least in part, a reservoir configured to contain the therapeutic agent. A shaft can be attached to the distal end region of the body. A lumen can extend through the shaft such that at least one inlet at a proximal end region of the shaft is in fluid communication with the reservoir and at least one outlet at a distal end region of the shaft. The shaft can have a length between the proximal end region and the distal end region such that upon implantation of the body in a region of the ear, the length of the shaft is sufficient to extend from the body to at least the round window membrane of the ear. The body can be sized to be implanted in a cavity of a middle ear of a patient. For example, in some implementations the reservoir of the drug delivery device can be positioned entirely within the tympanic cavity or a mastoid cavity of the middle ear and be coupled to a relatively short, shaft or intracochlear portion for delivery of drug directly into the cochlea. In some implementations, the shaft attached to the distal end region of the body can be a rigid, intracochlear portion having a helical thread-form on an outer surface configured to cut through and linearly advance into a wall of a cavity within which the body is implanted upon rotation.

Figure 2:
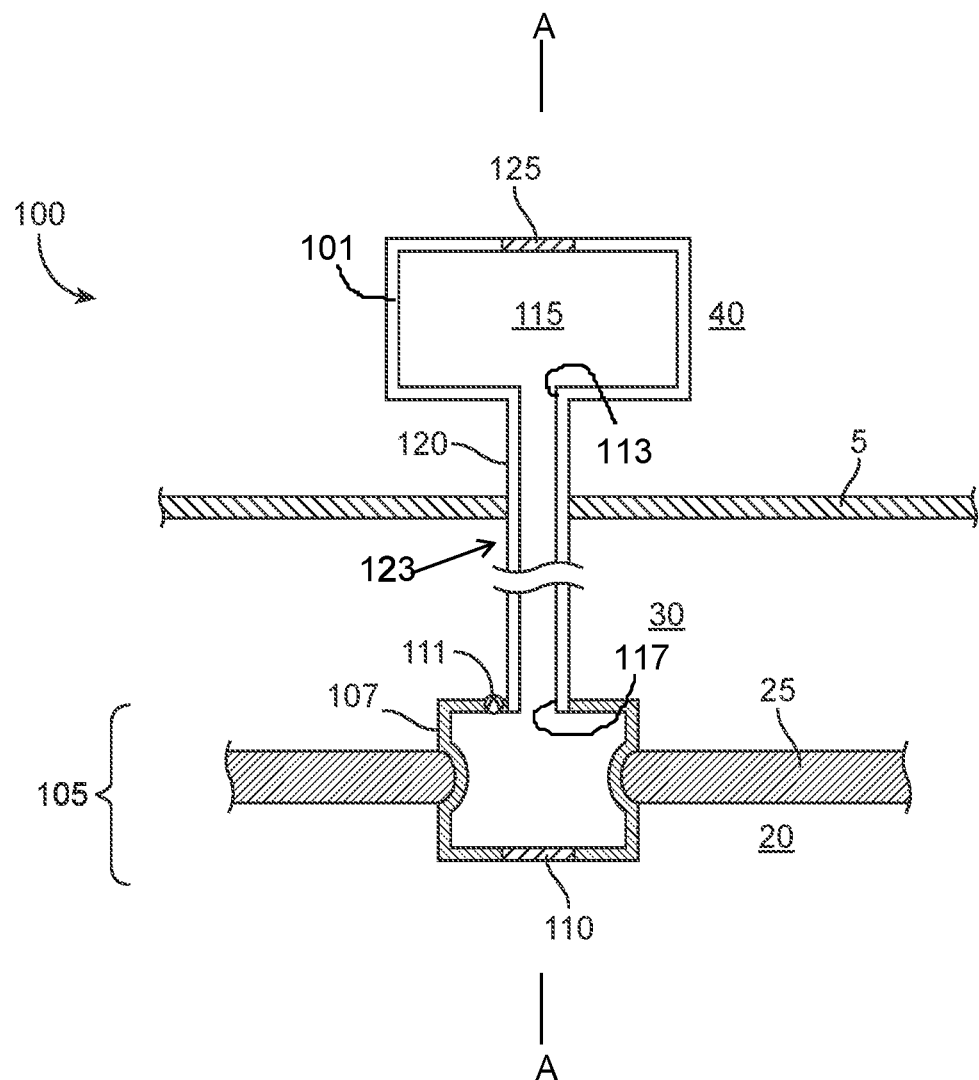
FIGS. 2-4 show various implementations of a drug delivery system in schematic having an implanted portion configured to deliver a therapeutic agent directly to the cochlea from a body that defines, at least in part, a reservoir configured to contain the therapeutic agent.
Figure 3:
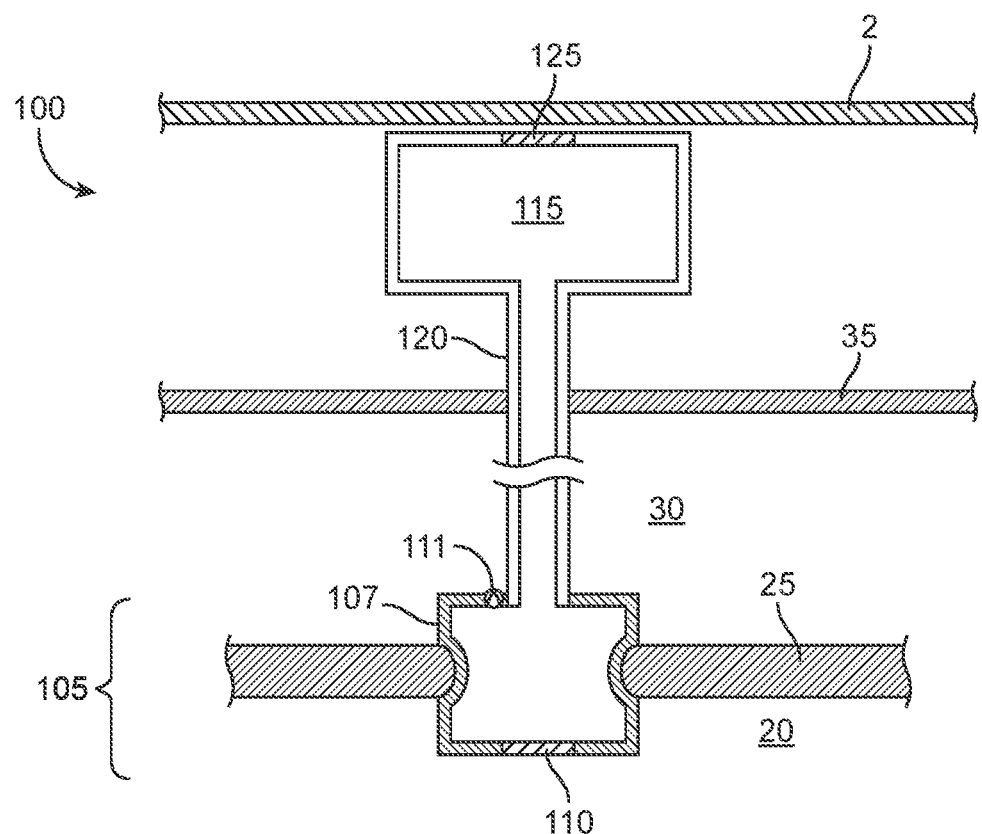
Figure 4:
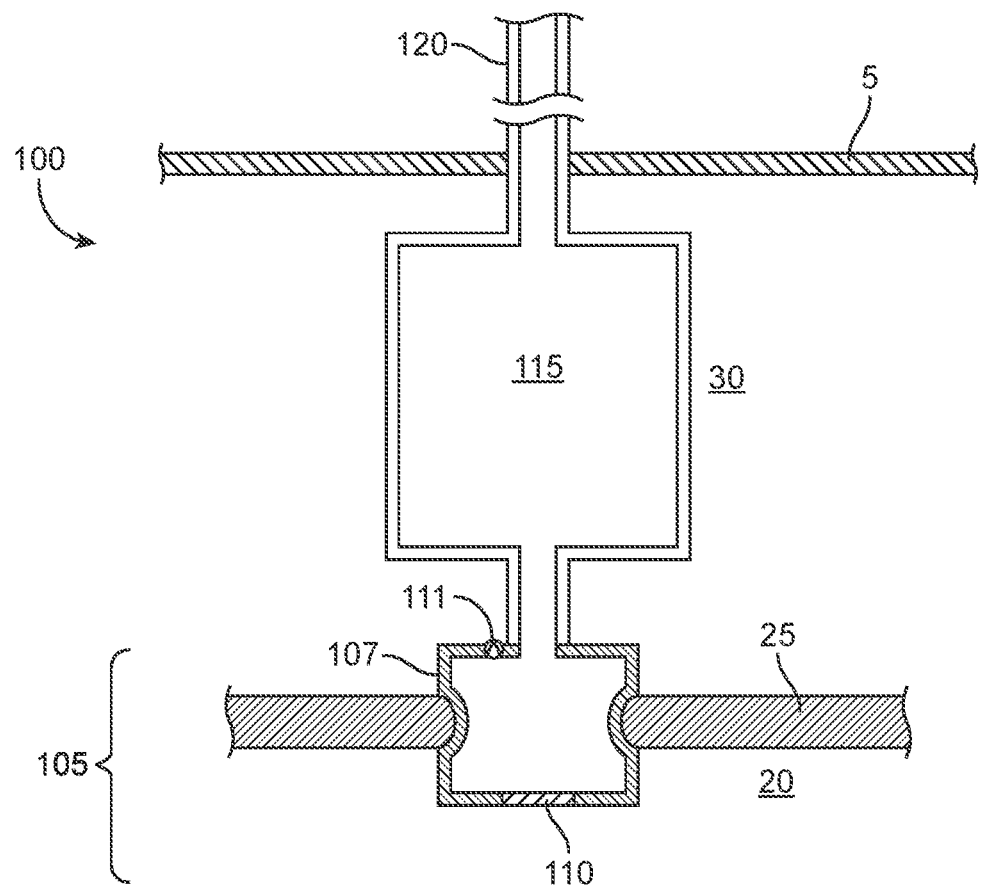

FIGS. 2-4 illustrate in schematic implementations of a drug delivery device 100 configured to deliver one or more therapeutic agents to one or more regions of the ear from a reservoir. The devices described herein can be positioned in many locations of the ear. However, in order to most effectively treat inner ear disorders, such as dysfunction of the hair cells, it can be desirable to deliver a drug from the device 100 directly into the cochlea 20.

Generally, the devices 100 described herein can include a body 101 having a distal end region and a proximal end region. The body 101 can define, at least in part, a reservoir 115 for containing a source of therapeutic agent 133 for sustained delivery to the ear via passive diffusion or capillary action such as via a lumen of a shaft and/or a drug release element 110. The shaft 123 can be an elongate element configured to extend from the body 101 to another region of the ear. Shaft 123 can be attached to the distal end region of the body 101 and have a lumen extending through the shaft 123. The lumen can have at least one inlet 113 at a proximal end region of the shaft 123 in fluid communication with the reservoir 115 and at least one outlet 117 at the distal end region of the shaft 123. Upon implantation of the body 101 in a region of the ear, the length of the shaft 123 is sufficient to extend from the body 101 to at least a portion of the ear for treatment. The length of the shaft 123 can provide the passive diffusion. In some implementations, the shaft 123 can be an elongate and relatively flexible cannula 120, and may be referred to herein interchangeably as a shaft or a cannula depending on configuration of the device and implantation location. In other implementations, the shaft 123 can be a relatively short element configured to extend through a wall of a cavity, such as the medial wall of the tympanic cavity 30 or a wall of the mastoid cavity. For example, the shaft 123 can be a relatively rigid, cannulated screw shaft having threads on an outer surface and a lumen extending through an interior of the shaft 123.

The device can include a porous drug release element 110 positioned relative to at least one of inlet 113 to the lumen of the shaft 123 and the outlet 117 from the lumen of the shaft 123. The drug release element 110 can be positioned near a distal end of the device 100 such that it can be positioned within the target treatment area. For example, the drug release element 110 can be positioned within the cochlea 20 or cochlear space 132 such that the one or more therapeutics 133 contained within the reservoir 115 can be delivered over time directly into the fluid of the cochlea 20 or the cochlear space 132. The drug release element 110 can be positioned at the end of a distal cannula that extends. Alternatively or additionally, the drug release element 110 can be positioned upstream from the cannula within an exit port of the reservoir. Each of these components can vary in material, structure and dimension (e.g. size, shape), as will be described in more detail below depending on the implantation location.

Figure 6A:
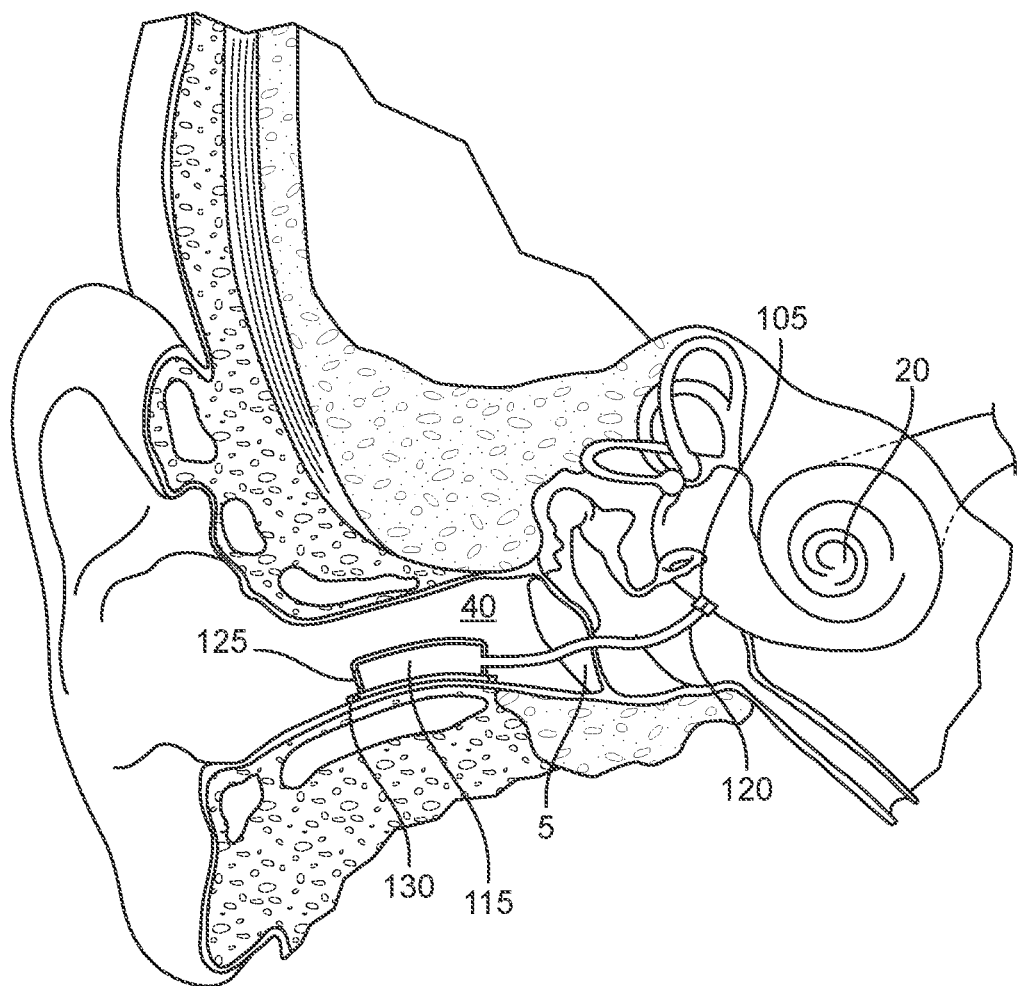
FIGS. 6A-6B show implementations of drug delivery device in schematic having an implanted portion configured to deliver therapeutic agent directly to the cochlea from a reservoir via a cannula extending through the tympanic membrane.
Figure 6B:
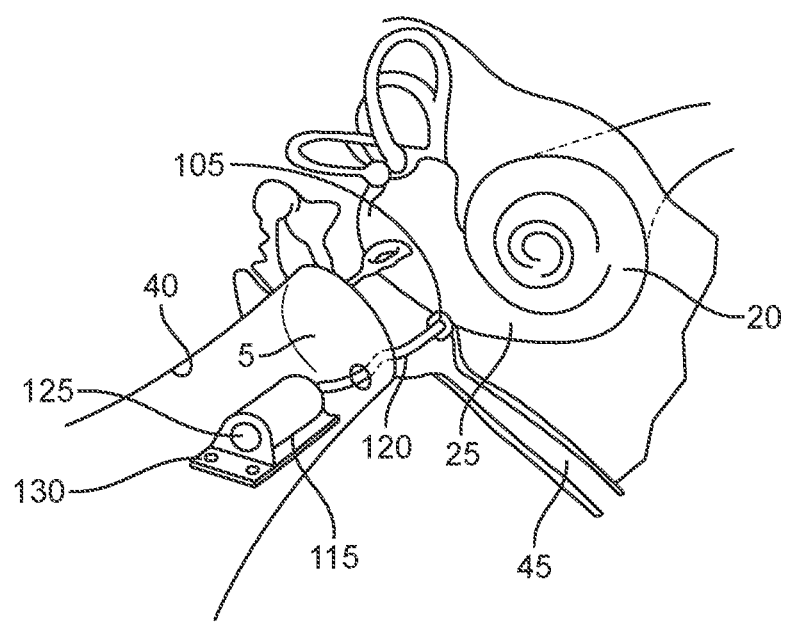
Figure 7:
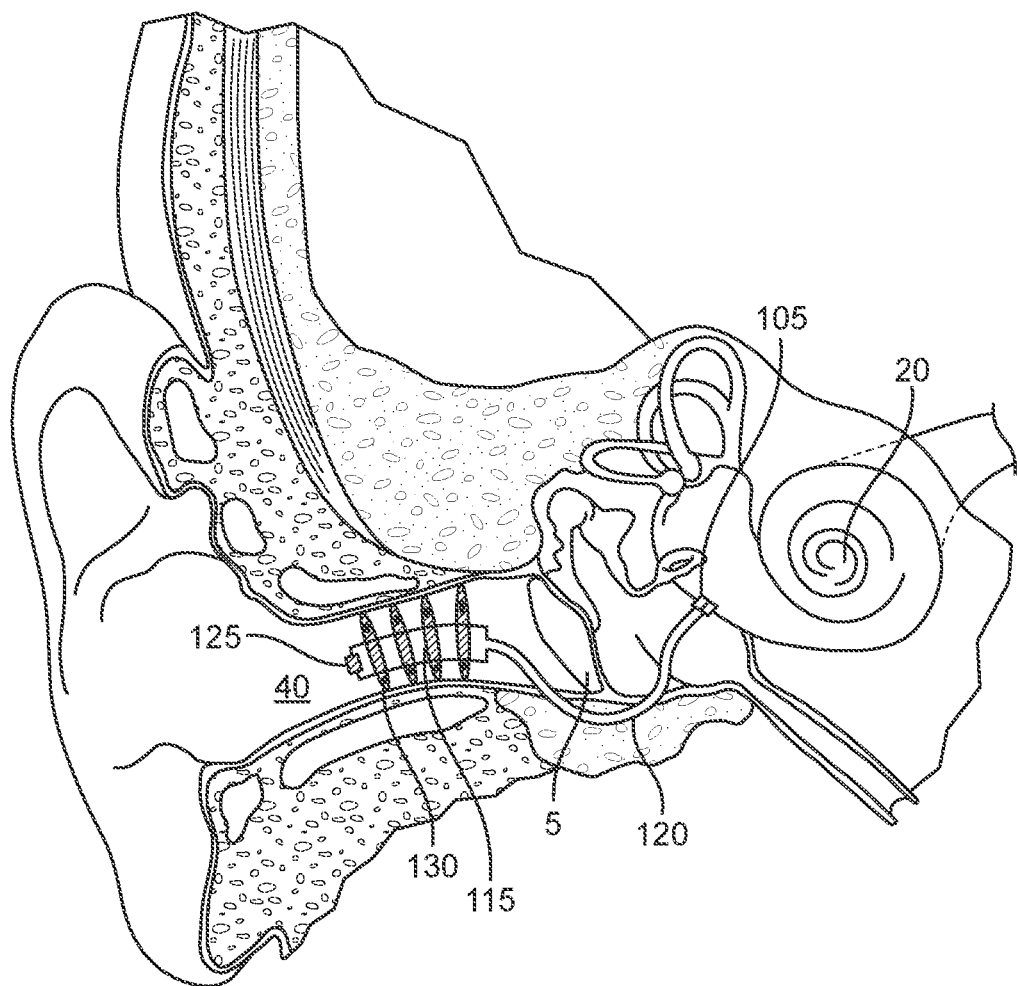
FIG. 7 shows an implementation of a drug delivery device in schematic having an implanted portion configured to deliver therapeutic agent directly to the cochlea from a body that defines, at least in part, a reservoir configured to contain the therapeutic agent via a cannula extending around the tympanic membrane.
Figure 8:
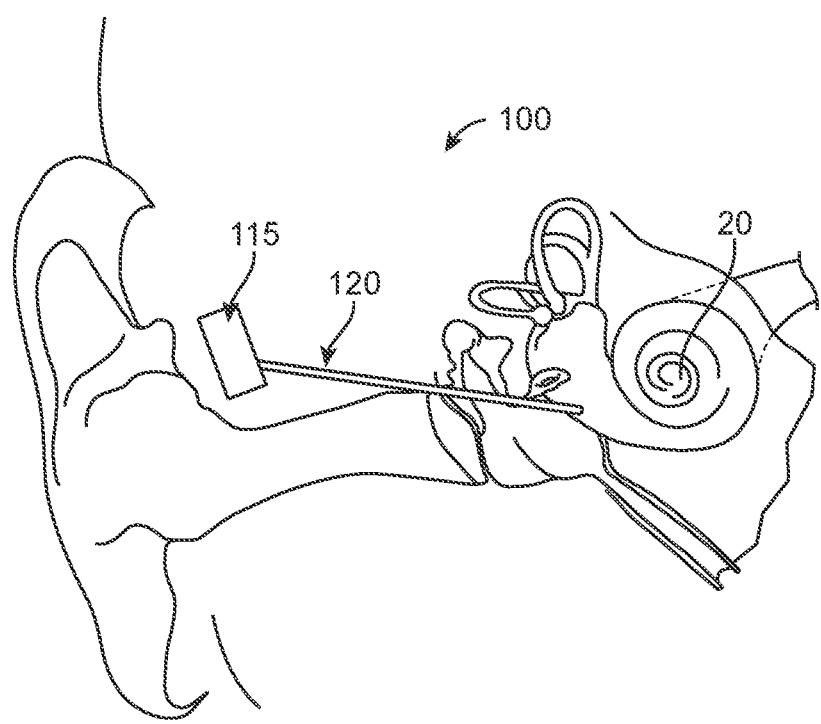
FIG. 8 shows an implementation of a drug delivery device in schematic having a subcutaneous reservoir extending via a cannula to an implanted portion.

A substantial volume of the reservoir 115 of the device 100 can be positioned external to the ear or internal to the ear. In the various implementations, the device 100 can include a shaft having a lumen such as a proximal cannula 120 extending from the reservoir 115. The proximal cannula 120 can communicate with an intracochlear portion of the device 100. The proximal cannula 120 can communicate between an intracochlear portion of the device 100 and an extra-cochlear portion of the device. FIG. 2 shows an implementation of the device 100 where a substantial volume of the reservoir 115 is positioned primarily within the ear canal 40 (see also FIGS. 6A-6B, and 7). FIG. 3 shows an implementation of the device 100 where a substantial volume of the reservoir 115 is positioned primarily within a subcutaneous region over a portion of the skull 35 (see also FIG. 8). FIG. 4 shows an implementation of the device 100 where all or a substantial volume of the reservoir 115 is positioned within the tympanic cavity 30 (see also FIGS. 12A-12E, FIGS. 14 and 23). The device 100 can be sized such that a substantial volume of the reservoir 115 can be positioned within a mastoid cavity of the middle ear. Depending on the configuration, the cannula 120 can extend between a region of the reservoir 115 to a region of the device 100 where the drug release element 110 is positioned. For example, as shown in FIGS. 2 and 3, the cannula 120 can extend from a region of the reservoir 115 to an implanted portion 105, which can be referred to herein as an intracochlear portion 105. The intracochlear portion 105 can vary in its configuration and implant location as will be described in more detail below. The device 100 can include an intracochlear portion 105 having a narrow outer diameter and an inner diameter forming a lumen 121 extending from the reservoir 115 to a distal end of the intracochlear portion 105. The distal end of the intracochlear portion 105 and thus the lumen 121 can be configured to deliver drug directly into the cochlear space 132 (see, for example, FIGS. 12A-12D and 14). If a drug release element 110 is employed, it can be positioned on or near the distal end of the lumen 121.

In some implementations, the intracochlear portion 105 can be positioned within, on, or near the round window 25. The reservoir 115 can include an access port 125 accessible through the ear canal 40, as shown in FIG. 2, or through the skin 2 if positioned subcutaneously as in FIG. 3. It should be appreciated that the reservoir can be placed externally (i.e. under the skin of the external ear canal), but can also be placed within other cavities such as the nasal cavity or the like. FIG. 4 shows a proximal cannula 120 that can extend to a proximal end region of a reservoir 115 and the reservoir 115 connected to the intracochlear portion 105 positioned within the round window 25. The reservoir 115 can be refillable from outside the inner ear via the proximal cannula 120. The volume of the reservoir 115 positioned within the tympanic cavity 30 is relatively small and limited by the anatomy of the middle ear. In some implementations, the reservoir 115 is not connected to a proximal cannula 120 per se. Rather, at least a portion of the reservoir 115 is positioned within the middle ear, or tympanic cavity 30, or mastoid cavity, and is fillable by an intra- or trans-tympanic needle 131 (see FIG. 26). The reservoir 115 can, in turn, be in fluid communication with the cochlear space 132 via the lumen 121 of the implanted portion 105 (see FIGS. 14 and 23). The reservoir 115 can be flushed and filled non-invasively while the intracochlear portion 105 of the device 100 remains implanted. In implementations where the reservoir 115 of the device 100 is positioned remote from the drug release element 110 (i.e. FIG. 2 and FIG. 3) and the substantial volume of the reservoir 115 of the device 100 is positioned outside the inner or middle ear, the volume of the reservoir 115 can be larger because it is not limited by the anatomy of the inner and middle ear.

The drug release element 110 can be positioned such that it is in fluid communication with the cochlea 20. For example, the drug release element 110 can be positioned near a distal end region of the intracochlear portion 105 (see FIGS. 2-4). The drug release element 110 can control or regulate the delivery of the one or more therapeutic agents stored in the reservoir 115. In some implementations, the drug release element 110 can be coupled to a portion of the intracochlear portion 105 configured to be positioned through the medial wall 138 of the tympanic cavity 30 or the round window membrane 27 such that the drug release element 110 is positioned directly within the cochlear space 132 (see FIG. 14).

In some implementations, the device 100 replaces the round window membrane 27 entirely and in other implementations, the device is positioned within a hole created in the round window membrane 27 given the anatomical variations in dimension of the membrane and shape of the round window niche. For example, a drill (e.g. 2 mm) may be used to create a pilot hole in the location of the round window and the drug delivery device 100 may be positioned within the hole. Positioning the drug delivery device 100 in this manner may result in a more reproducible fit relative to the anatomy compared to replacing the entire membrane. The drug delivery device 100 may also be implanted without creating a pilot hole and incorporate self-tapping threads or other anchoring implantation features, which will be described in more detail below.

When placing a cannula through the round window membrane 27 for chronic local drug delivery, there can be a risk of tearing or perforation. Dislocation or wound healing subsequent to cannula placement through the membrane may potentially result in fibrosis or membrane overgrowth of the round window membrane 27. Thus, in some implementations, the round window membrane 27 is removed entirely and replaced with a permanent device. The intracochlear portion 105 can be positioned within the cochlea 20 such that hearing is not impacted by the drug delivery device 100. The intracochlear portion 105 can replace the round window membrane 27. The device can provide anchoring within the location as well as sealing between the device and the surrounding tissues. The device can provide therapy through a drug release element. Importantly, at least a portion of the device can be distensible to allow pressure waves to be transmitted from the oval window as would the natural round window membrane 27. The device can further include an annular anchor having an outer surface and an inner surface. The outer surface can be configured to seal against a region of the eye, such as a perimeter of a round window membrane. For example, the intracochlear portion 105 can include an annular anchor such as a support ring 107 spanned by the drug release element 110. The support ring 107 can be sized and shaped such that the outer surface of the annular structure can seal against and engage with the round window 25. The support ring 107 can be semi-rigid or rigid and the drug release element 110 can be compliant to maintain the functionality of the round window membrane 27. Thus, the drug release element 110 functions as the round window membrane following implantation of the device 100 within the round window 25. The support ring 107 can be sufficiently less compliant than the drug release element 110 such that it can provide support to the compliant drug release element 110 and anchor it within the round window 25. The compliant drug release element 110 can be permeable to the therapeutic agent to be delivered to the cochlea 20.

The various functions of the device (i.e., anchoring/sealing/drug release/distensibility) can be performed by a single component of the device. Alternatively, different components of the device can provide one or more of the functions. For example, in the example provided above, the support ring 107 can provide anchoring and sealing whereas the drug release element 110 can provide both drug release and distensibility for maintaining acoustic impedance. In another implementation, the device 100 can include a drug release element 110 that is a rigid, porous outer ring configured to control drug diffusion from the reservoir while a flexible, interior ring can be incorporated that is configured to be responsive to perilymph movement/pressure wave. Regardless of the configuration, the devices described herein can replace the round window membrane while retaining the natural function of the round window membrane by matching its impedance properties.

The intracochlear portion 105 can have a shape and size configured to provide a snug fit (i.e. conforming fit) within the round window 25 or medial wall 138 of the tympanic cavity 30 thereby minimizing fluid leakage from the inner ear 20 while the drug release element 110 allows for normal sound-induced vibrations to be transmitted. In some implementations, the intracochlear portion 105 can have a generally hour-glass shape. For example and as shown in FIGS. 10A-10H, the support ring 107 can include a middle portion 108 having a first diameter that is bordered by a proximal portion 106 and a distal portion 109 each having a second, larger diameter than the first diameter. The first diameter of the middle portion 108 can be sized to fit snugly within the round window 28 (or the medial wall 138) while the proximal portion 106 extends outside the window 28 on a side of the tympanic cavity 30 and the distal portion 109 extends inside the window 28 on a side of the cochlea 20. In some implementations, the diameter of the middle portion 108 can be between about 1.0 mm up to about 2.0 mm whereas the diameters of the proximal and distal portions 106, 109 can be between about 1.5 mm up to about 2.5 mm. The drug release element 110 can span the inner diameter of the support ring 107 near the distal portion 109 such that upon positioning the intracochlear portion 105 within the round window 28, the drug release element 110 can be positioned within the cochlea 20. The drug release element 110 can have a diameter between about 1.0 mm to about 3.0 mm, preferably about 2.0 mm.

In the implementation shown in FIGS. 10A-10H, the rigid or semi-rigid annular ring 107 can provide anchoring in the cochlea and can be spanned by two distensible membranes—a first membrane that is permeable to allow drug diffusion and a second membrane that is non-permeable to the drug. The drug formulation can be contained between the two membranes. The permeable membrane allows for diffusion into the cochlea while the second membrane interfaces with the middle ear. The two membranes with incompressible drug formulation between move in concert in response to pressure changes within the cochlea.

Figure 10C:
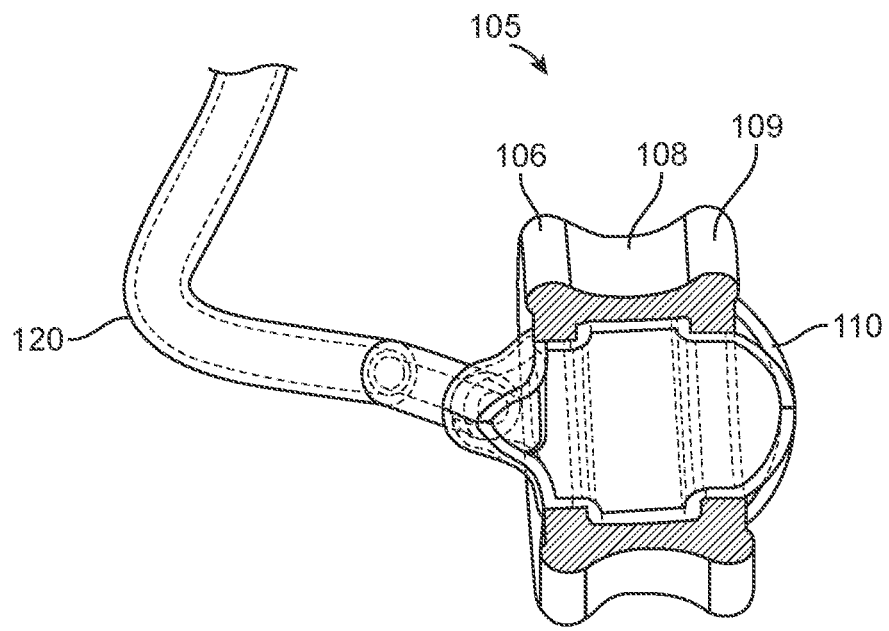
Figure 10I:
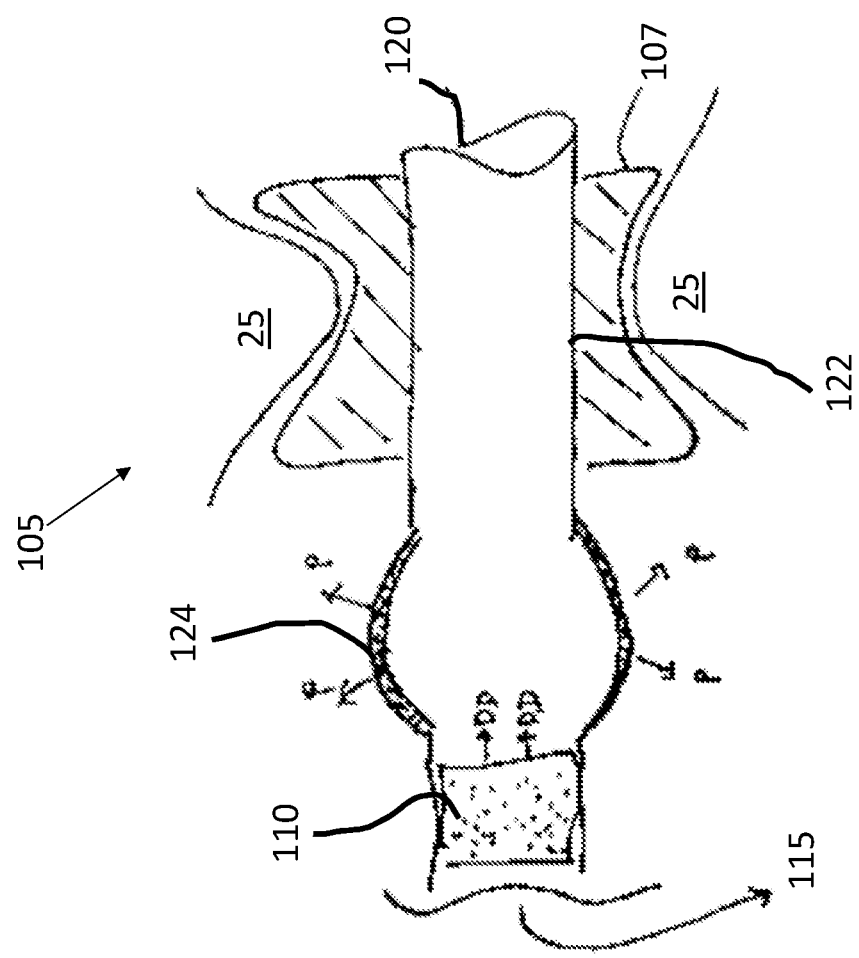
FIG. 10I shows an implementation of an intracochlear portion of a drug delivery device.

In another implementation, the intracochlear portion 105 can include a cannula 120 extending from a drug reservoir 115 and an annular anchor. The annular anchor can have an outer surface and an inner surface. The outer surface can be configured to seal against a perimeter of a round window membrane and the inner surface can encircle a segment of the shaft that extends through the anchor. The annular anchor can be formed of a conformable material or a semi-rigid material. For example, the cannula 120 can have a first segment 122 surrounded by a conforming, semi-rigid support ring 107 for fixation in the cochlea (see FIG. 10I). A second segment 124 of the cannula 120 immediately proximal to the cochlea can have a distensible wall (e.g. a balloon). A porous drug release element 110 can be positioned within a region of the cannula 120 just proximal to the second segment 124 that is configured to control drug diffusion rate into the cochlea through the first segment 122 of the cannula 120. The environment within the cochlea distal to the first segment 122 surrounded by the ring 107 can be a fluid environment filled with perilymph. The environment outside the cochlea proximal to the first segment 122 is air. The element 110 can effectively dampen the pressure wave from the cochlea and shunt it to the distensible wall of the second segment 124. Air of the middle ear thus interfaces with the impedance element and is thus more likely to function similarly to a natural round window membrane.

Figure 10K:
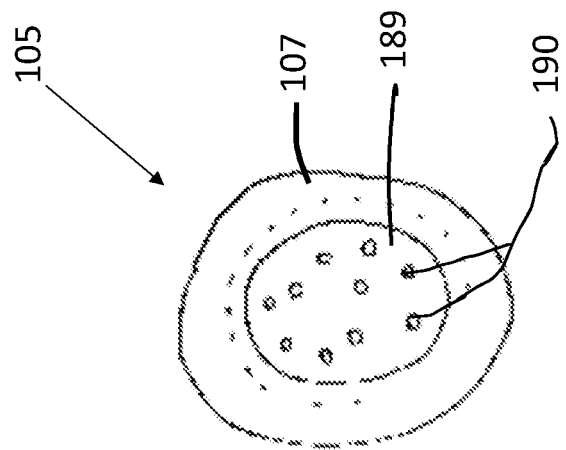
FIG. 10K shows a top plan view of the device of FIG. 10J.
Figure 10J:
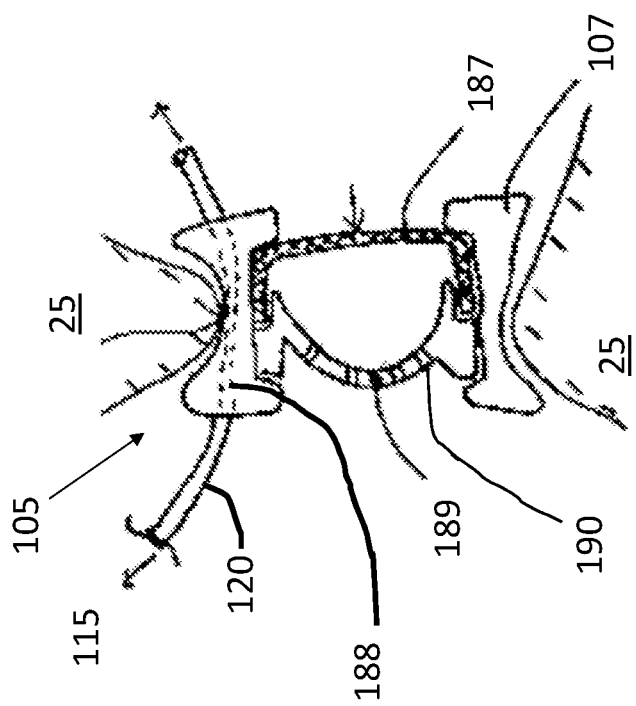
FIG. 10J shows a cross-sectional view of another implementation of an intracochlear portion of a drug delivery device.
Figure 11B:
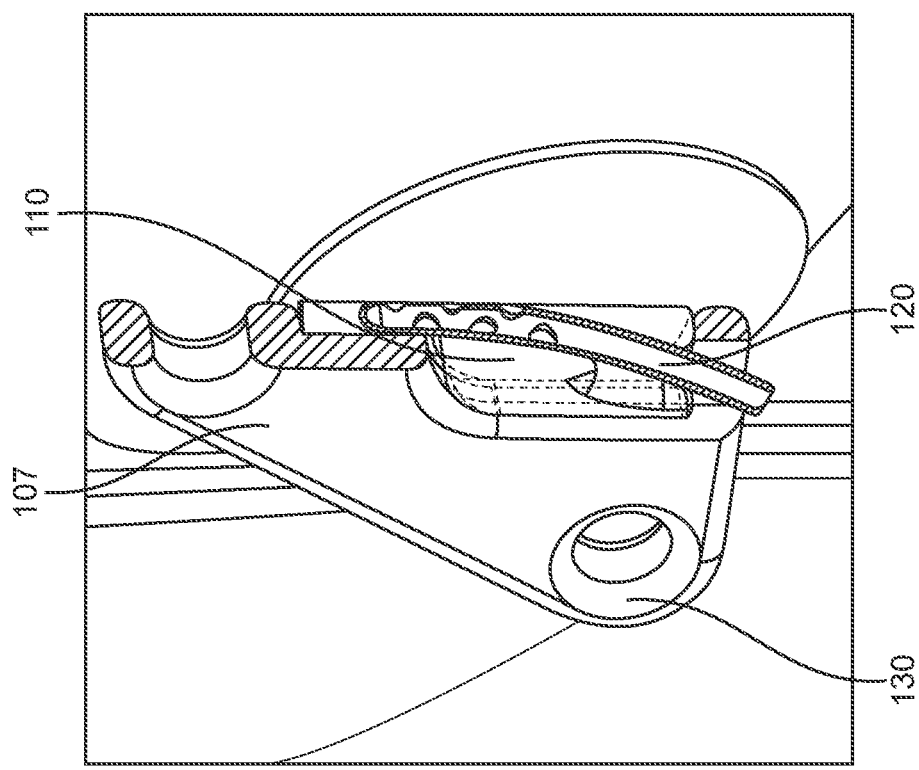
FIGS. 11A-11F show various views of an implementation of a round window diffusion implant of a drug delivery device.
Figure 11A:
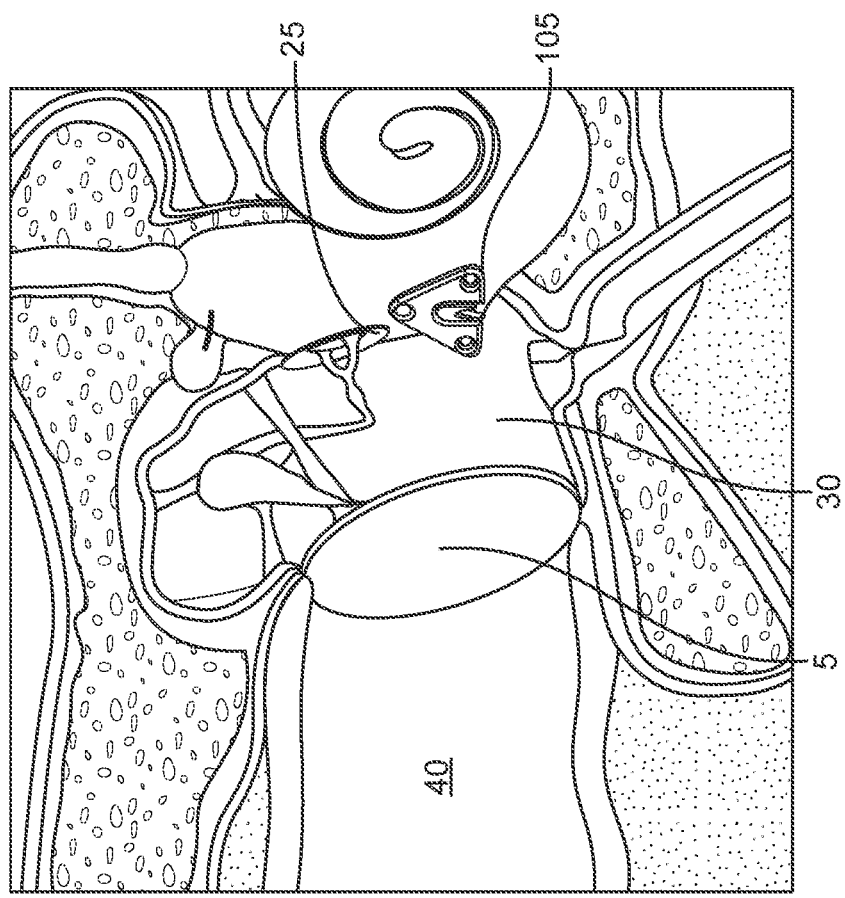
Figure 11C:
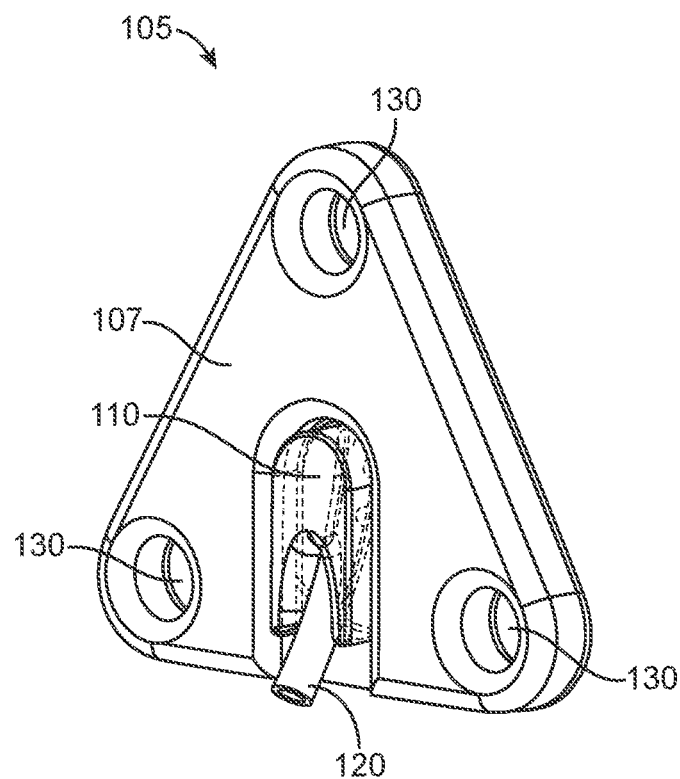
Figure 11D:
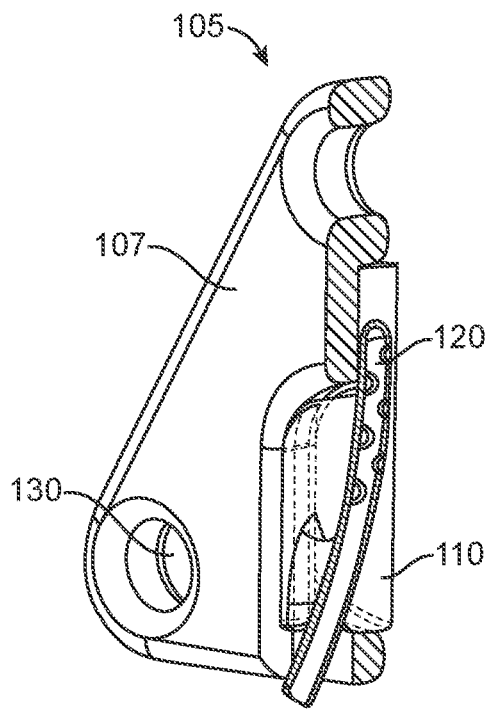
Figure 11E:
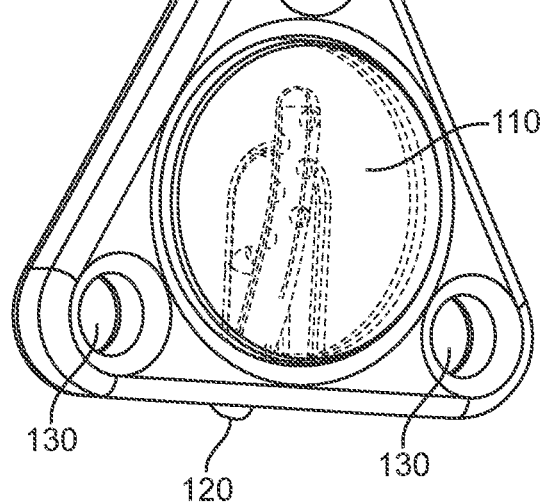
Figure 11F:
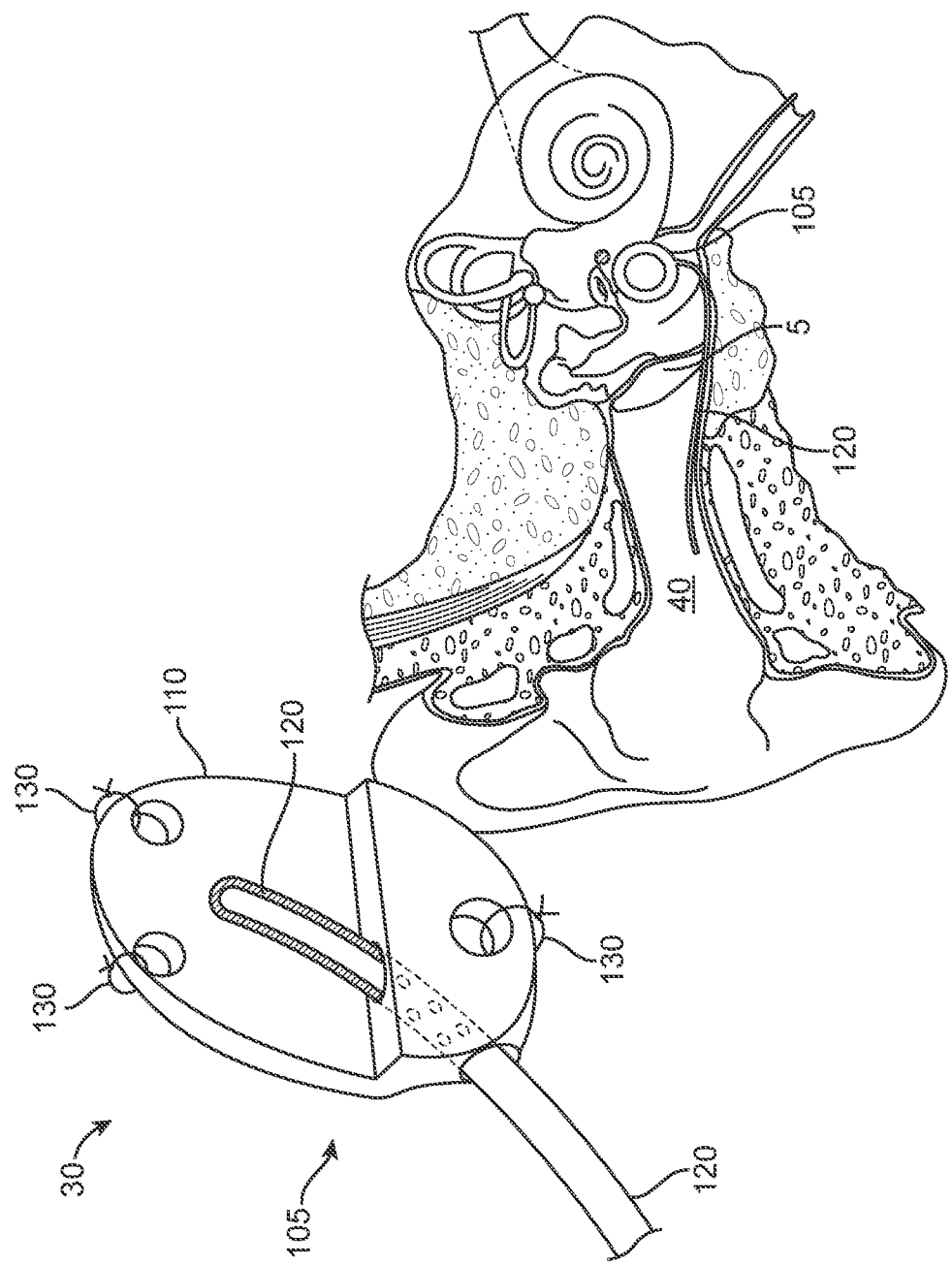

In yet another implementation, the intracochlear portion 105 can include a rigid or semi-rigid ring 107. The ring 107 is an annular anchor having an outer ring surface configured to seal against a perimeter of a round window membrane or other region of the eye and an inner ring surface. The ring 107 can be spanned by a distensible membrane 187 on a distal side (i.e. the perilymph side of the device) and includes a channel 188 extending through a portion of the ring 107 for passage of the drug delivery cannula 120 into the cochlea (see FIGS. 10J-10K). The channel 188 can extend through the annular anchor from a proximal surface of the anchor to a distal surface of the anchor. The channel 188 can have an inner diameter sufficient to receive an outer diameter of a distal end region of the drug delivery cannula 120 such that at least a portion of the cannula 120 can be received within and in some instances extend clear through the ring 107 into the perilymph side of the device. The size and/or length of the cannula 120 can provide the drug delivery from the reservoir 115 to the cochlea. In this implementation, the device need not incorporate a porous drug release element per se. Rather, the drug release element can be the cannula 120 configured to deliver drug from the reservoir 115 in a passive slow release over an extended period of time. The device can include a rigid plate 189 positioned opposite to and substantially parallel with the distensible membrane 187 on a proximal side of the device (i.e. the air side of the device). The anchor can include a chamber located within the annular anchor and defined collectively by the inner ring surface, an inner surface of the rigid plate 189, and an inner surface of the distensible membrane 187. The plate 189 can include fenestrations 190 or be otherwise porous to allow air to pass across the plate 189. The plate 189 can provide structural support and protection of the distensible membrane 187. Upon implantation of the device, the chamber within the ring 107 between the plate 189 and the membrane 187 can be filled with air and the distal surface of the distensible membrane 187 can be surrounded by perilymph. The distensible membrane 187 on the perilymph side of the device can provide the function that a natural round window membrane would otherwise provide. For example, the distensible membrane provides acoustic impedance similar to an acoustic impedance of the round window membrane. It should be appreciated that the annular anchor can include two distensible membranes and need not incorporate a rigid plate 189. For example, a first distensible membrane may be coupled to a proximal side of the annular anchor and a second distensible membrane can be coupled to the distal side of the annular anchor opposite the first distensible membrane. The first distensible membrane can be non-permeable to the therapeutic agent and the second distensible membrane can be permeable to the therapeutic agent. The at least one outlet at the distal end region of the shaft can be positioned in fluid communication with the chamber. Passive diffusion of the therapeutic agent can include passive diffusion through at least one of the distensible membranes.

The distensible components described herein (e.g. the distensible membrane 187, the second segment 124 of the cannula 120) can be formed of silicone, polyurethane, and other elastomeric polymers having a shore hardness capable of being deformed upon application of a sound pressure wave within the ear. The rigid components described herein (e.g., the fenestrated plate 189) can be formed of PEEK, titanium, and other relatively non-distensible materials that maintain their shape upon application of a sound pressure wave within the ear. The ring 107 described above can be rigid (i.e. formed of PEEK, titanium, etc.) or can be semi-rigid. Materials suitable for a semi-rigid ring 107 include, but are not limited to silicone, PTFE and other materials having a shore hardness capable of conforming to a degree relative to the anatomy in the ear to provide sufficient anchoring and sealing upon implantation.

The intracochlear portion 105 can have a drug release element 110 configured to deliver therapeutic agent through the round window membrane 27 (see FIGS. 5, and 11A-11F). The device 100 can deliver therapeutic from a reservoir that can be positioned in a variety of locations, including but not limited to, the ear canal 40, subcutaneously outside the skull 35, or within the tympanic cavity 30, or the mastoid cavity, as described elsewhere herein. The intracochlear portion 105 can be positioned such that the drug release element 110 lies against the round window membrane 27 and therapeutic agent diffuses through the membrane 27 rather than directly inside the cochlea 20.

The drug release element 110 can be any of a variety of structures as described herein. In some implementations, the drug release element 110 can be a porous foam or other porous material configured to be saturated with an aqueous solution of therapeutic agent delivered from the reservoir by the cannula 120 and then release the therapeutic onto the membrane 27. The drug release element 110 need not be formed of or incorporate a porous material per se, but rather itself can be a structure configured to control diffusion such as through a length of the path or size of an opening. For example, a length of a cannula leading from the reservoir can be sufficient to control diffusion from the reservoir to the treatment site such as for the implementation shown in FIG. 10J. The drug release element 110 can be positioned within an opening of a support structure 107 such that a proximal side of the drug release element 110 can be in fluid communication with the distal end of the cannula 120 and a distal side of the drug release element 110 can be in fluid communication with the round window membrane 27. A distal end of the cannula 120 can include one or more openings to saturate the drug release element 110. The support structure 107 can have any of a variety of configurations, but is generally shaped and sized to support the drug release element 110 such that the drug release element 110 can be positioned in contact with the round window membrane 27. In some implementations, the support structure 107 can be rigid or semi-rigid material. In other implementations, the drug release element 110 can be more malleable. The support structure 107 can include one or more retention features 139 on the intracochlear element 105 such that the support structure 107 can be affixed to the round window 25, such as by sutures or other fixation mechanisms.

Figure 12A:
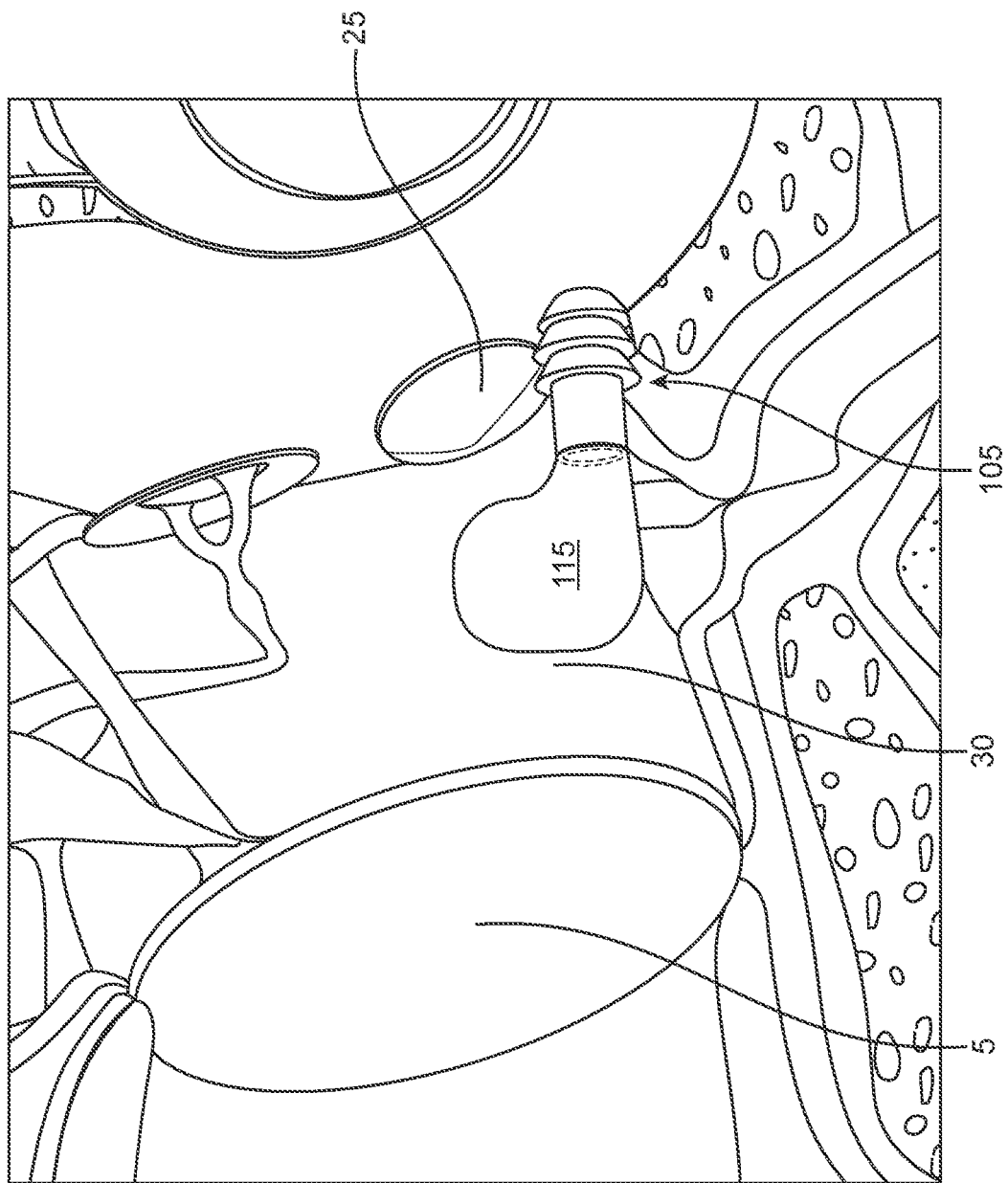
FIGS. 12A-12E show various views of another implantation of a drug delivery device.
Figure 12B:
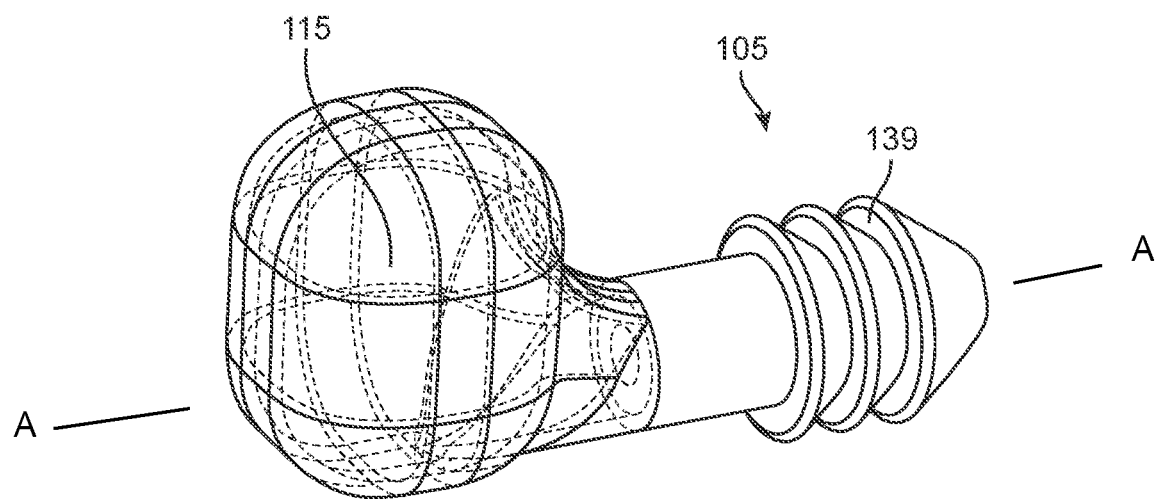
Figure 12C:
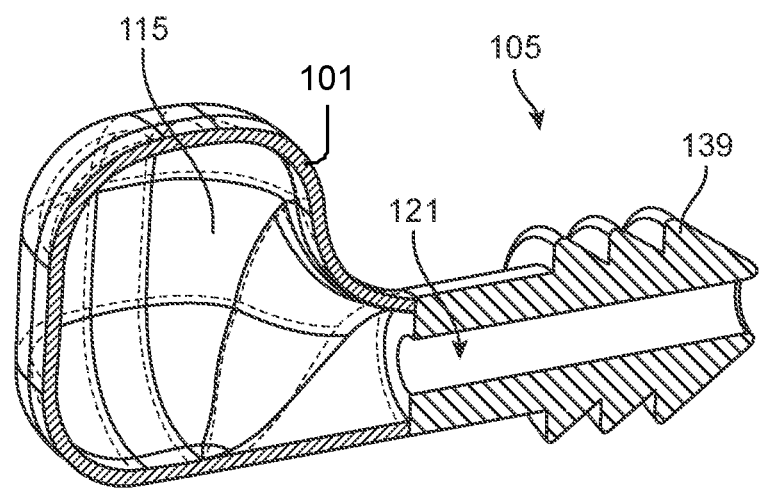
Figure 12D:
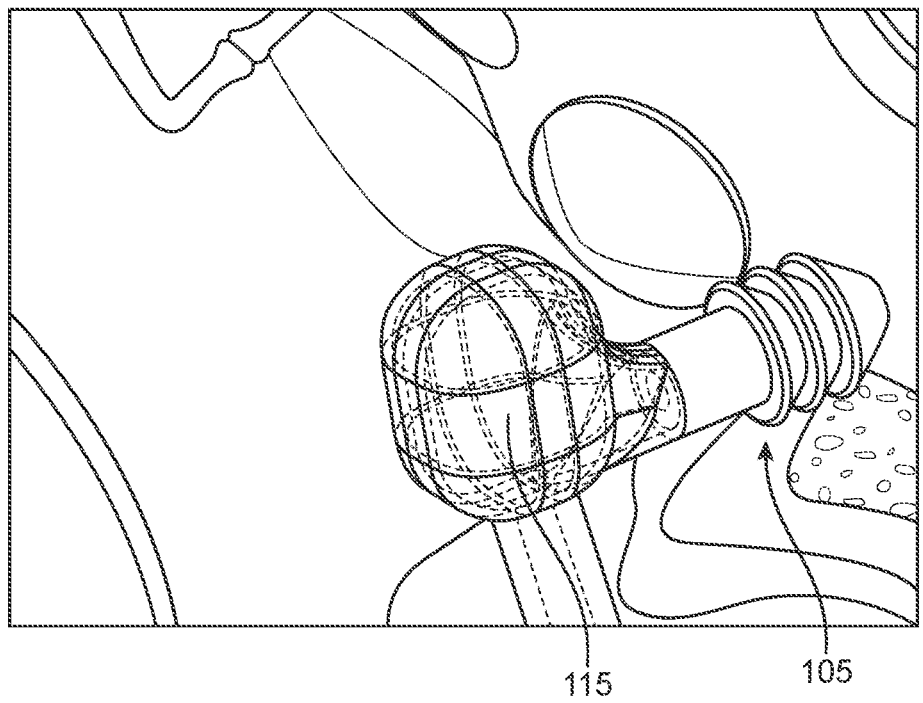

In an implementation, the device can include a reservoir 115 attached to an intracochlear portion 105 (i.e. proximal retention structure) as shown in FIGS. 12A and 12B. The intracochlear portion 105 can be self-anchoring and it can be placed into the cochleostomy. In some implementations, the intracochlear portion 105 includes a thread-form, such as helical self-tapping thread-forms on its outer surface configured to cut through and linearly advance upon rotation of the intracochlear portion 105 such that no pilot hole need be drilled in order to implant the device in position. In an implementation, the device can include a body 101 having a distal end region and a proximal end region, the body 101 configured to be implanted in a cavity of a middle ear of the patient. As with other implementations, the body 101 can define, at least in part, a reservoir 115 configured to contain the therapeutic agent. A shaft 123 can be attached to the distal end region of the body 101 and includes a lumen 121 extending through an interior of the shaft 123. The lumen 121 can include at least one inlet 113 at a proximal end region of the shaft 123 in fluid communication with the reservoir 115 and at least one outlet 117 at a distal end region of the shaft 123. As such, when the body 101 is implanted in the cavity, the shaft 123 can extend through a wall of the cavity and the at least one outlet 117 is positioned into a cochlear space. The shaft 123 can include a helical thread-form on an outer surface of the shaft 123 that is configured to cut through the linearly advance into the wall upon rotation. The device can deliver the therapeutic agent from the reservoir 115 via passive diffusion through the at least one outlet 117 of the shaft 123 into the perilymph of the cochlear space.

Figure 12E:
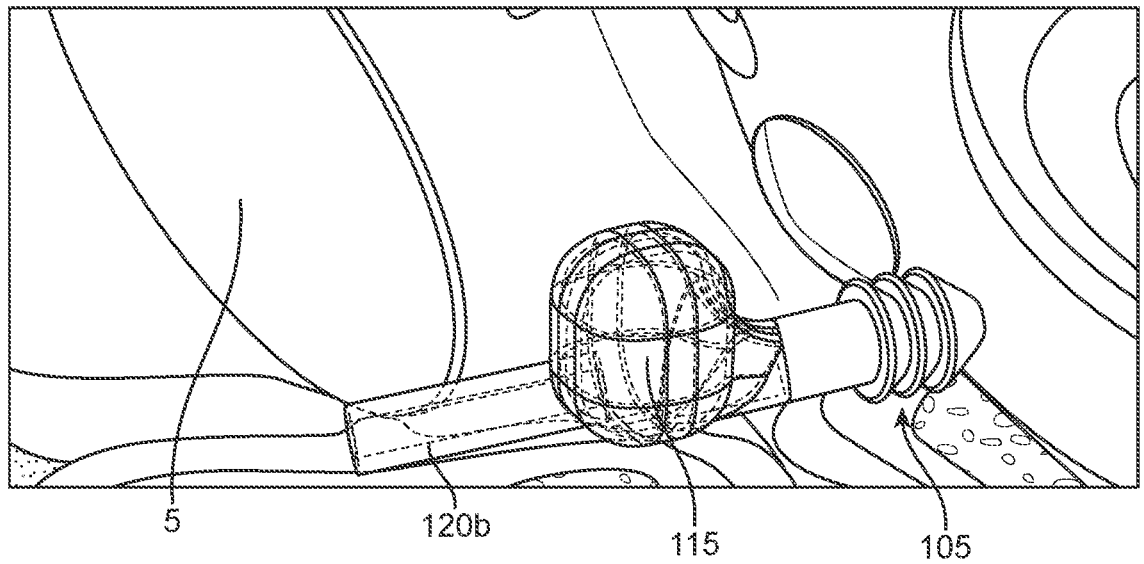

The flexible reservoir 115 can be placed in the tympanic cavity 30. The intracochlear portion 105 can have a lumen 121 that extends through the entire length of the intracochlear portion 105 from the proximal reservoir 115 to the distal delivery tip to deliver a therapeutic agent to a target treatment area (see FIG. 12C). Although the lumen 121 is shown substantially aligned with the longitudinal axis A of the shaft, the internal lumen may also be positioned eccentrically. The drug release element 110 can be positioned at a distal end of the lumen 121 or proximal end of the lumen 121 or along a length of the lumen. The length of the shaft through which the lumen extends can be sufficient to sit deep enough into the cochlea for an outlet from the lumen 121 to be exposed and to allow drug diffusion into the target treatment area. As described elsewhere herein, the reservoir 115 can be refilled such as via a proximal cannula 120. FIG. 12E shows the general placement of the refill cannula 120 used to replenish the reservoir 115, for example, via the tympanic membrane 30.

Figure 13A:
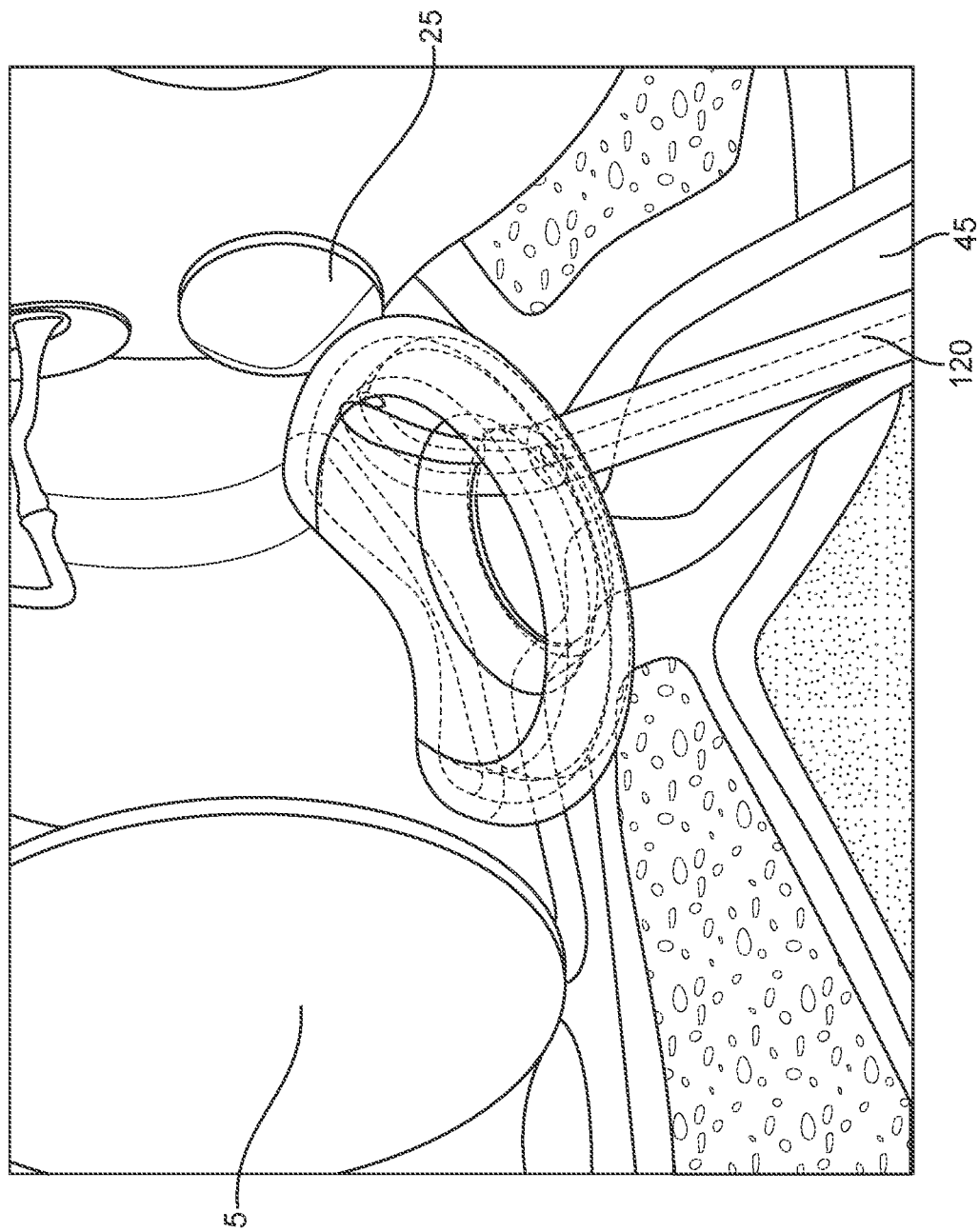
FIGS. 13A-13C show another implementation of a drug delivery device.
Figure 13B:
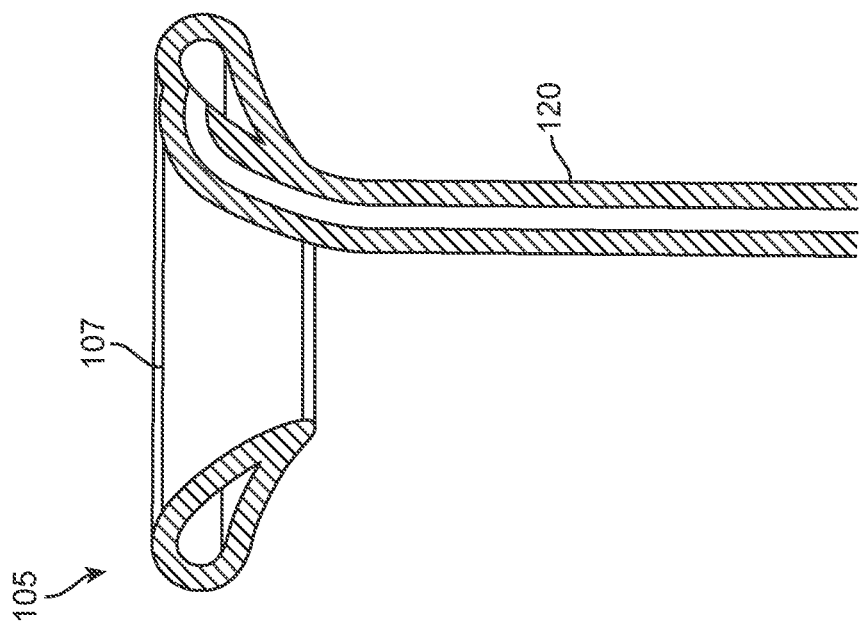
Figure 13C:
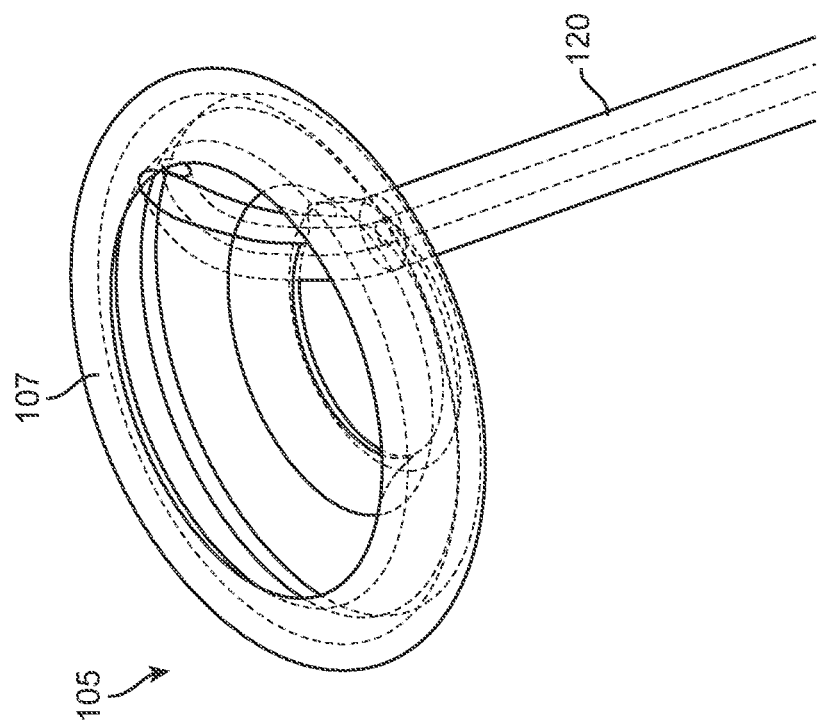

Upon implantation of the body 101 in a region of the ear, the length of the shaft 123 can be sufficient to extend from the body 101 to at least a region of the ear for treatment (e.g. the round window membrane). The shaft 123 can form at least a portion of the intracochlear portion 105 as described elsewhere herein. As such, at least a portion of the shaft 123 having a lumen 121 may be referred to herein as an intracochlear portion 105. The drug delivery devices described herein can include an implanted portion that is referred to as an intracochlear portion 105. It should be appreciated that the implanted portion of the device need not be positioned in direct communication with the cochlear space or intracochlearly. For example, in some implementations, the implanted portion 105 may be placed within the Eustachian canal 45 (see FIGS. 13A-13C). The implanted portion 105 can be a generally soft material such that it can be placed through the sinus or Eustachian canal 45. The reservoir 115 can be located in a variety of locations as described elsewhere herein and may be in communication with the implanted portion 105 via a cannula 120. The reservoir 115 can be located in the ear canal 40, subcutaneously behind the ear, or the sinus.

The contents of the reservoir 115 can be delivered according to slow diffusion rather than expelled as a fluid stream or pumped from the reservoir 115. In some implementations, the drug release element 110 can be a covering or lining having a particular porosity to the substance to be delivered and can be used to provide a particular rate of release of the substance. The drug release element 110 can be a release control mechanism, including but not limited to a wicking material, permeable silicone, packed bed, small porous structure or a porous frit, multiple porous coatings, nano-coatings, rate-limiting membranes, matrix material, a sintered porous frit, a permeable membrane, a semi-permeable membrane, a capillary tube or a tortuous channel, nano-structures, nano-channels, sintered nanoparticles and the like.

As described herein, the device can include an elongate shaft 123 having a lumen 121. The elongate shaft 123 can be an elongate, flexible cannula 120 extending between the body 101 defining, at least in part, the reservoir 115 and the intracochlear portion 105. The path taken by the cannula 120 extending between the reservoir 115 and intracochlear portion 105 can vary and may depend on where the reservoir 115 is positioned. In some implementations, the cannula 120 extends from the reservoir 115 positioned within the ear canal 40 through the tympanic membrane 5 (see FIGS. 6A-6B) or around the tympanic membrane 5 (see FIG. 7). In some implementations, the cannula 120 extends from a reservoir 115 positioned within the middle ear to an intracochlear portion 105 positioned within or through the round window membrane. In other implementations, the reservoir 115 can be positioned such that the cannula 120 bypasses the outer and middle ear and avoids disrupting the tympanic membrane 5. In other implementations, the reservoir 115 can be positioned such that the cannula 120 passes through the mastoid cortex, the middle ear, and promontory bone and avoids disrupting the tympanic membrane 5 or the round window membrane 27. The cannula 120 can also extend through the Eustachian canal 45 and connect with a reservoir 115 positioned within the sinus. The cannula 120 can be rigid or flexible (i.e. compliant). If the cannula 120 is rigid, at least a portion of the cannula 120 can be formed of a softer more flexible material. Such materials are commonly known to those of ordinary skill in the art and can include silicon- or vinyl-based materials, flexible di-(2-ethylhexyl) phthalate (DEHP) plastic, soft polyvinyl chloride (PVC) plastic, and non-latex rubber, for example.

Figure 22:
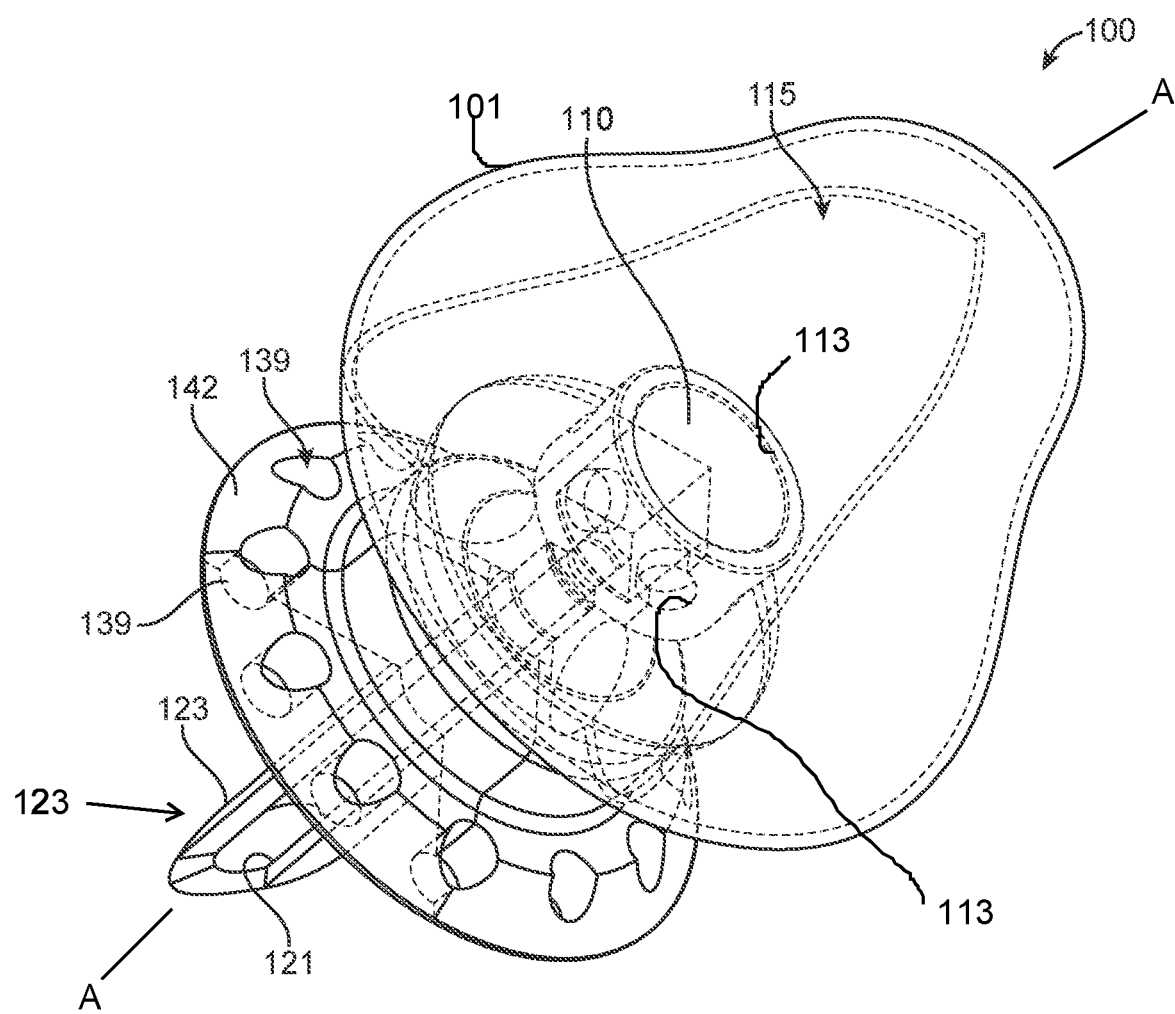
FIG. 22 shows an implementation of a drug delivery device with a separable mounting plate from a perspective view.
Figure 23:
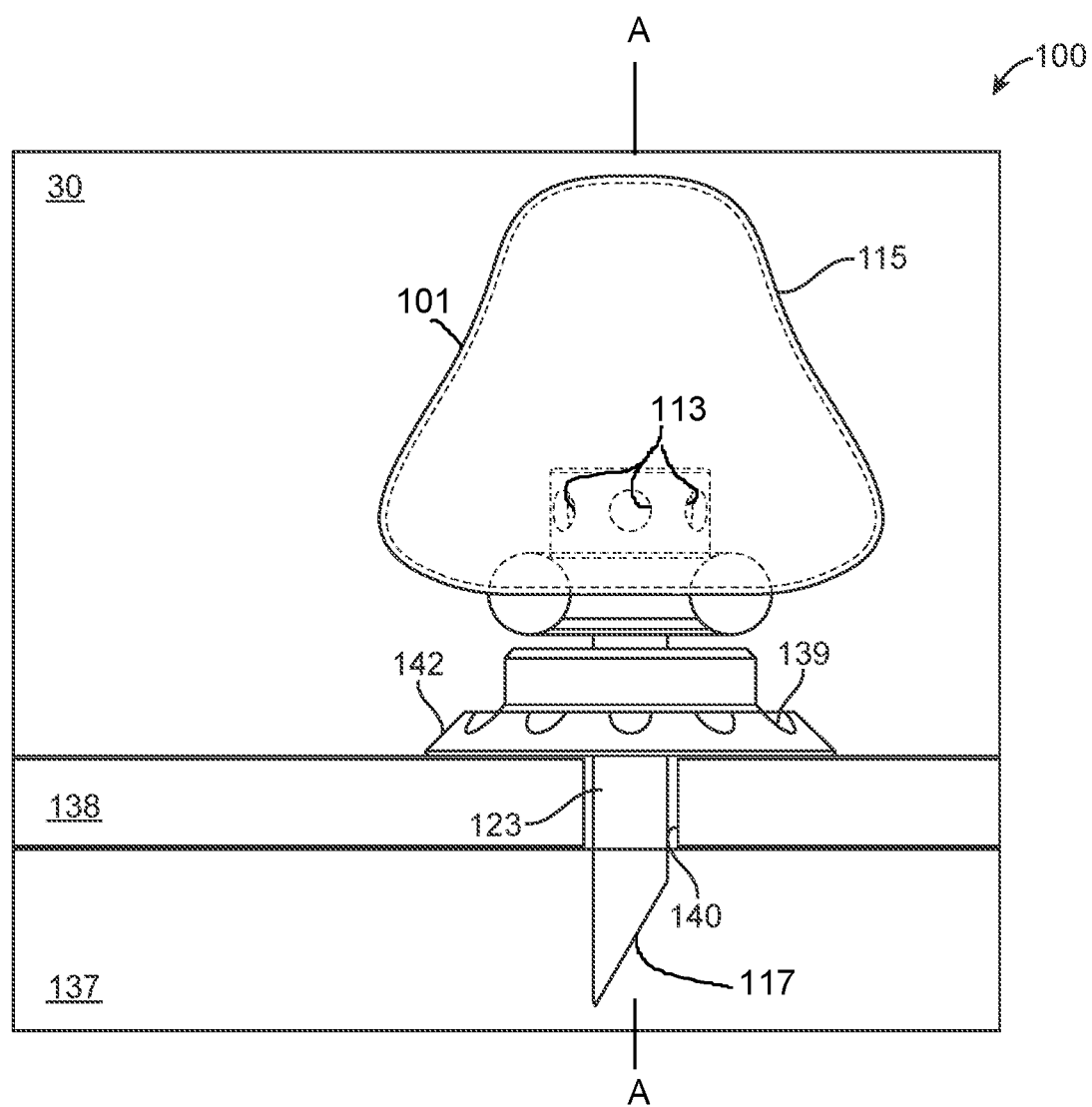
FIG. 23 shows a method of placement of a drug delivery device with a separate mounting plate as viewed from the side.

In still other implementations, which will be described in more detail below, the device need not include a cannula connecting the reservoir 115 and the intracochlear portion 105. Rather, the body 101 defining the reservoir 115 and the intracochlear portion 105 can be directly attached such that the shaft 123 attached to the distal end region of the body 101 and the lumen 121 extending through the shaft 123 provides the fluid communication between the interior of the reservoir 115 and the inner ear. The length of the shaft 123 (i.e. a length between an inlet 113 into the lumen 121 to at least one outlet 117 from the lumen 121 at a distal end region of the shaft 123) is sufficient to extend from the body 101 into the target treatment location. The reservoir 115 can be positioned within the tympanic cavity 30 and the intracochlear portion 105 positioned through or within the medial wall 138. The lumen 121 extending through the intracochlear portion 105 can be in fluid communication with the reservoir 115 at a proximal end and communicate at a distal end with the cochlear space 132 of the inner ear (see FIGS. 14 and 23). In this way, the lumen 121 of the implanted portion 105 maintains a fluid connection (i.e. remains in fluid communication) with the reservoir 115 such that the therapeutic agent can be delivered from the reservoir 115 to the cochlear space 132 via the lumen 121 (see, for example, FIGS. 14, 16, 18, and 20). The intracochlear portion 105 can be inserted through an opening 140 in the medial wall 138, including a cochleostomy, for example (FIGS. 22 and 23). The intracochlear portion 105 can be rigid or flexible throughout or have a combination of variable flexibilities along the length of the intracochlear portion 105 to facilitate implantation and positioning at specific target sites in the inner ear. Each will be described in more detail below.

Generally, the devices described herein, once implanted, are configured to minimally disrupt the natural functions of the surrounding anatomy such that therapeutic effect can be provided with minimal to no impact on acoustic impedance. For example, if a device is implanted to extend through or replace the round window membrane, at least a portion of the device is configured to function as the round window membrane would otherwise function (e.g. transmittance of a pressure wave). Similarly, if a device is implanted to extend through the bony wall of the cochlea, at least a portion of the device is configured to function as the portion of the bony wall would otherwise function.

In some implementations, the reservoir 115 and/or the intracochlear portion 105 can have one or more retention features 139. For example, where the reservoir 115 is positioned within the ear canal 40, the reservoir 115 can include retention features 139 that engage with the wall of the ear canal 40. Where the reservoir 115 is positioned within the middle ear, the reservoir 115 can include one or more retention features 139 that engage with a medial wall 138 of the tympanic space 30. In other implementations, the one or more retention features 139 include flexible support members, sutures or suture holes, anchors or anchor holes, prongs, flanges, or an expandable feature like a stent or other deformable element configured to radially expand or change shape. Various other retention features 139 are described with reference to FIGS. 14, 15A-15E, 16, 17A-17C, 18, 19A-19D, 20, 21A-21D, 22, and 23, each of which will be described in more detail below.

In some implementations, the volume of the reservoir 115 can be at least about 1 µL, 2 µL, 3 µL, 4 µL, 5 µL, 10 µL, 15 µL, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 96 µL, 97 µL, 98 µL, 99 µL, 100 µL, 125 µL, 150 µL, 175 µL, 200 µL, 225 µL, 250 µL, 275 µL, 300 µL, 325 µL, 350 µL, 375 µL, 300 µL, 425 µL, 450 µL, 475 µL, up to about 500 µL. In some implementations, the volume of the reservoir 115 is between about 5 uL to about 1 mL. As described above, the reservoir volume can vary depending on where the reservoir 115 resides. For example, a reservoir 115 positioned within the tympanic cavity 30 of the middle ear may have a smaller overall volume compared to a reservoir 115 positioned within the ear canal 40 or outside the ear (e.g. subcutaneously or within a mastoid pocket). Middle ear cavity reservoirs can have a volume sized up to about 25 µL. The maximum cross-sectional dimension of a reservoir implanted in the middle ear cavity can be up to about 5 mm. Reservoirs sized to be implanted within the mastoid cavity can be slightly larger than middle ear cavity reservoirs. Such reservoirs can have a volume up to about 1 mL. The maximum cross-sectional dimension of a reservoir sized for implantation within the mastoid cavity can be up to about 10 mm. It should be appreciated that any of a variety of volumes are considered herein, particularly where the reservoir 115 is positioned externally or under the skin. It should be appreciated that use of the term "reservoir" refers to the container holding a source volume of therapeutic agent, the source volume being sufficient for the extended delivery of the therapeutic. The "reservoir" as used herein, generally does not refer to the volume of drug that may reside within a cannula or the intracochlear portion 105 at any given time during sustained release of the therapeutic.

Because distensible (i.e. "stretchy") materials can react to changes in pressure, some portions of the device within the inner and middle ear are formed of non-distensible material that do not react to pressure changes whereas other portions of the device within the inner and middle ear may preferably be formed of distensible materials that do react to pressure changes (e.g. the distensible membrane 187). However, implanting a device into the inner ear may benefit from being collapsible and expandable. For example, FIGS. 12A-12E show an implementation of a drug delivery device 100 having a reservoir 115 configured to be implanted within the middle ear, such as within the mastoid cavity or tympanic cavity 30. The material of the body 101 defining the reservoir 115 can be flexible such that it can be collapsed for insertion and expanded upon filling. The body 101 defining the reservoir 115 need not be flexible or expandable, but rather fixed in shape and size and formed of a substantially rigid or non-compliant material. The intracochlear portion 105 having the drug release element 110 can be positioned through a cochleostomy opening near the round window 25. The reservoir 115 can include one or more retention features 139 configured to retain the reservoir 115 within the cavity. A proximal cannula 120 (see FIG. 12E) can be coupled to a region of the reservoir 115 such that the reservoir 115 can be refilled as described elsewhere herein. In some implementations, the proximal cannula 120 can provide refill access through the Eustachian canal 45 or through/around the tympanic membrane 5.

Examples of collapsible, non-distensible, substantially non-compliant materials are provided herein, including but not limited to polyethylene terephthalate (PET), nylon, and acrylics. Other materials are also considered herein, including but not limited to silicone rubber, titanium, biocompatible plastics, urethane, and acrylics. The material of the reservoir can also include urethane, nylon, Pebax®, polyurethanes, cross-linked polyethylene, fluorinated ethylene propylene (FEP), polytetrafluoroethylene (PTFE), and similar materials and blends of materials. The materials may also include multiple layers of the above materials and other materials known in the art for manufacturing expandable elements.

As mentioned herein, the reservoir 115 of the device 100 can be refilled and includes one or more penetrable refill or access ports 125. The access port 125 can be configured to be penetrated from outside the inner ear for substantially non-invasive filling, flushing, and/or refilling of the reservoir 115. Generally, the access port 125 can include a penetrable barrier configured to be penetrated. In some implementations, the access port 125 can be formed by an opening within a region of the reservoir 115 and covered by or filled with a penetrable material configured to be penetrated and resealed such that material does not leak out of the device 100 following penetration. In other implementations, the access port 125 represents an external portion of the proximal cannula 120 configured to connect with a filling needle to fill a remote reservoir 115 positioned within the ear as described above. In some implementations, the access port 125 can incorporate a needleless valve. The reservoir 115 can be positioned subcutaneously or within a mastoid pocket and the access port 125 can be accessed by penetrating the skin.

Figure 9A:
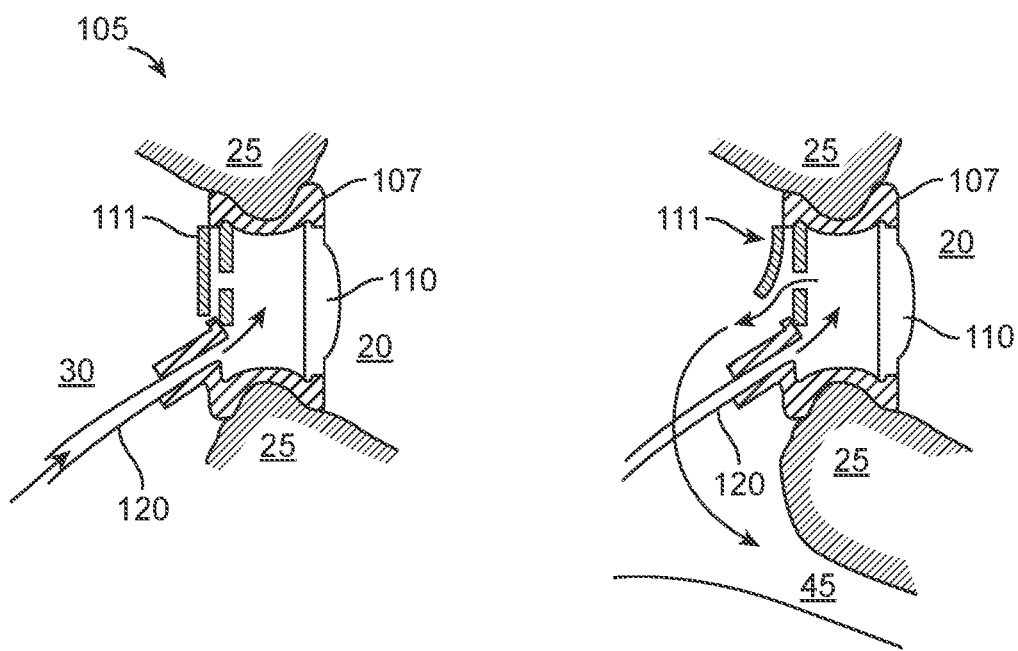
FIG. 9A shows an implementation of a drug delivery device having an implanted portion with a drain valve.

The intracochlear portion 105 can include one or more pressure relief valves 111 that can open during pressurization, for example, when refilling of the reservoir. In some implementations, the relief valve can vent excess fluid from the implant 105 and direct the fluid towards the Eustachian canal 45 and digestive system (see FIG. 9A). The valve 111 can be positioned within the proximal end portion of the intracochlear portion 105 such that upon reaching a certain filling pressure through the proximal cannula 120, the valve 111 opens and allows fluid from inside the intracochlear portion 105 to exit into the tympanic cavity 30 and out the Eustachian canal 45. This prevents damage to the intracochlear portion 105 and/or reservoir 115 and the ear, for example, during filling, refilling, and flushing of the system 100.

The devices described herein can remain in position to deliver one or more therapeutic agents to the ear for a period of time. In some implementations, drug can be delivered from the device 100 for at least about 30 days, preferably at least about 45 days, about 60 days, about 75 days, about 90 days, up to about 6 months or more. It should be appreciated the device 100 can, but need not, be removed from the ear after initial implantation. Thus, the device 100 can be refilled with fresh drug periodically during its lifetime without being removed from the patient.

Figure 9B:
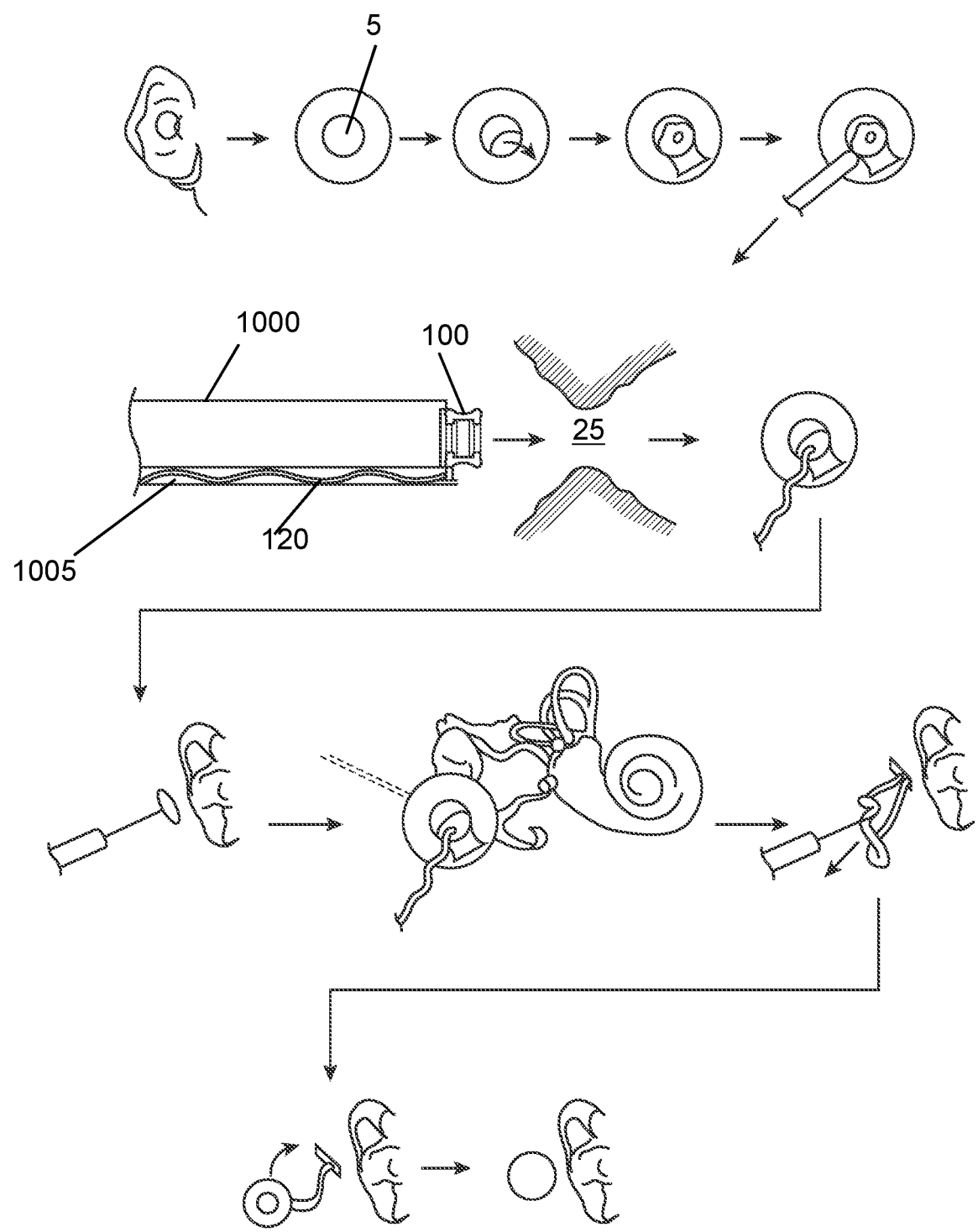
FIG. 9B shows a method of positioning the implanted portion of a drug delivery device.

An insertion instrument may be used to deliver the device 100 toward the round window 25. The approach can vary and include typical approaches that provides access to the inner ear or cochlea, including transcranial, transcanal, endaural, retroauricular (postaural), and other approaches. In some implementations, the devices described herein can be implanted using an elongate delivery tool 1000 (see FIG. 9B). The delivery tool 1000 can hold the intracochlear portion 105 near a distal end region of the tool 1000. In some implementations, the delivery tool 1000 can allow the proximal cannula 120 connecting the intracochlear portion 105 to the reservoir 115 to extend through a lumen 1005 of the delivery tool 1000. It should be appreciated that the implant methods can be performed manually or automatically (i.e. robot-assisted) or combinations thereof (i.e. semi-automatically).

It should be appreciated that the treatment devices described herein can be used in a variety of locations and implanted in a variety of ways. The implantation method and use of the treatment devices described herein can vary depending on the type of treatment device being implanted and the intended location and drug for treatment. The treatment devices described herein can be primed, implanted, filled, refilled, and/or explanted using one or more devices.

In an implementation, access to the middle ear can be achieved without cutting the tympanic membrane. Using a transcanal approach, a tympanomeatal flap in the ear canal can be created allowing the tympanic membrane to be pulled back. Alternatively, a post-aural approach can be used by creating an incision directly behind the ear, creating a channel between the ear canal wall and the mastoid process or temporal bone. The cochlea can be accessed by surgically removing the round window membrane or by creating a cochleostomy near the round window to create a new access point. The intracochlear portion 105 can be loaded within a delivery tool to drive the intracochlear portion into position. The delivery tool can be disengaged from the intracochlear portion leaving the intracochlear portion 105 in position. The middle ear access point can be closed. The proximal cannula 120, if present, can be routed as needed depending on where the reservoir 115 is to be located (i.e. along ear canal wall to postaural area). A subcutaneous port can be placed under the skin and the remaining incisions closed.

In some implementations, the device 100 can be positioned such that the drug release element 110 can be in fluid communication within the inner ear through a surgically created opening in the round window 25 or through a cochleostomy through the sidewall of the inner ear or through a cochleostomy through a medial wall separating the tympanic cavity, for example. The device 100 can be inserted through the round window 25 from the outer ear canal 35 and a tympanomeatal flap, using techniques typical of implant surgery. A suprameatal approach, an atticotomy approach, a trans-canal approach, a mastoidectomy and posterior tympanotomy approach, or a myringothomy approach for insertion of the device 100 is considered herein. In some implementations, the remote access proximal cannula 120 can pass through or around the tympanic membrane 5 and down the ear canal 40. In other implementations, the proximal cannula 120 can be fully subcutaneous and terminate near the ear, for example, behind the ear. In other implementations, the proximal cannula 120 can extend down the Eustachian tube 45 and into the nasopharynx.

Figure 14:
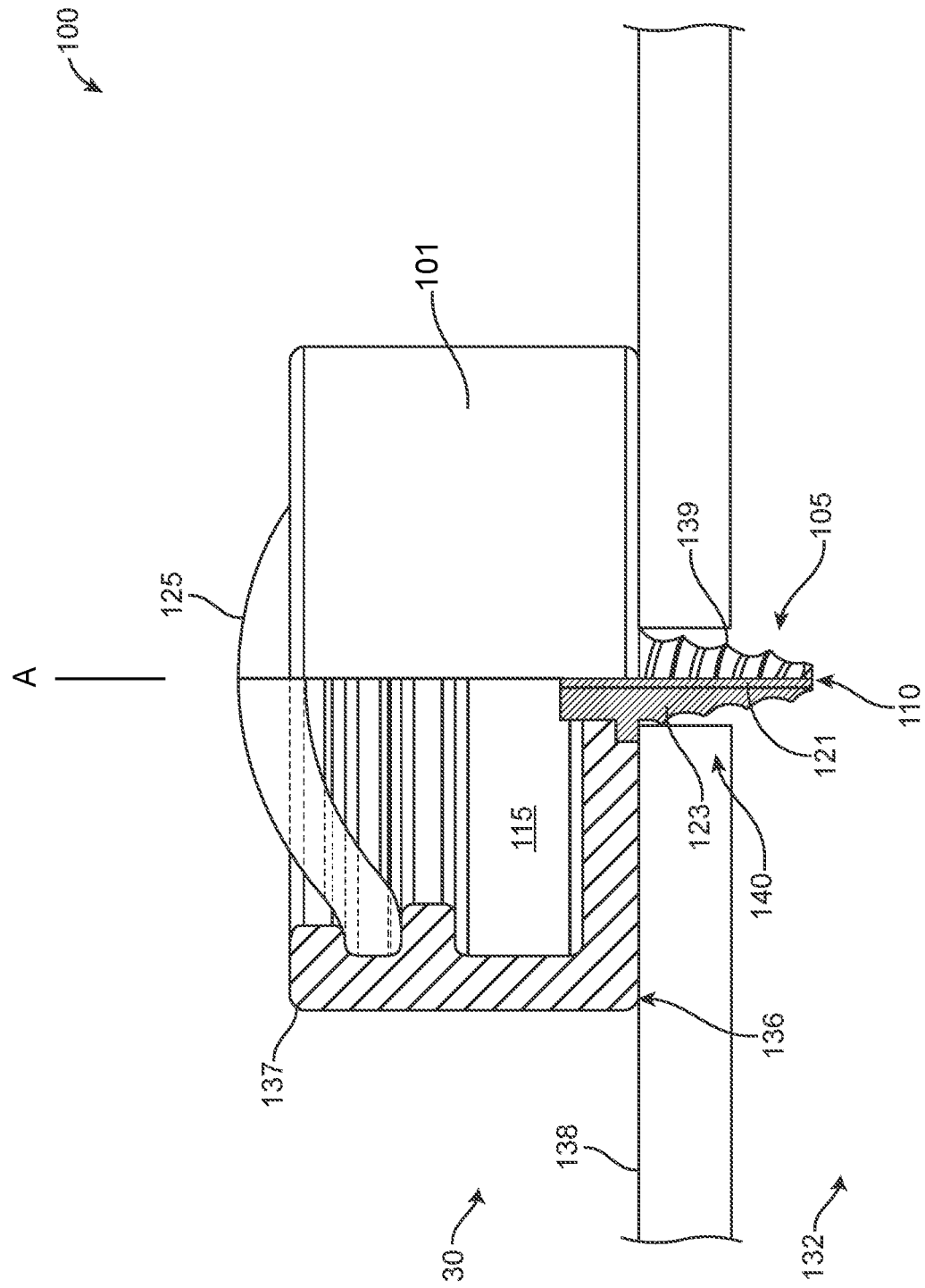
FIG. 14 shows a side view of an implementation of a drug delivery device.

FIG. 14 illustrates a further implementation of a drug delivery device 100 having an intracochlear portion 105, a body 101 defining a reservoir 115 configured to contain the therapeutic agent 133, and a drug release element 110. As described elsewhere herein, the device can include a shaft 123 attached to the distal end region of the body 101 defining the reservoir 115, the shaft 123 including a lumen 121 extending through the shaft 123. The lumen 121 can include at least one inlet 113 at a proximal end region of the shaft 123 in fluid communication with the reservoir 115 and at least one outlet 117 at a distal end region of the shaft 123. The shaft 123 can have a length between the proximal end region and the distal end region such that upon implantation of the body 101 in a region of the ear, the length is sufficient to extend from the body 101 to at least a treatment location. The porous drug release element 110 can be positioned relative to at least one of the inlet 113 and the outlet 117 from the lumen 121 of the shaft 123. The intracochlear portion 105 connects to the reservoir 115 on a proximal end and the drug release element 110 on the distal end. The reservoir 115 can be defined at least in part by a body 101. The body 101 can be a cylindrical element that is substantially rigid. Upon implantation of the device 100, the body 101 can be positioned within the tympanic cavity 30 of the patient and the intracochlear portion 105 can extend through the medial wall 138 of the tympanic cavity 30 such that the distal end of the intracochlear portion 105 is in fluid communication with the cochlear space 132. The body 101 can include a distal end region 136 and a proximal end region 137. In some implementations, a penetrable access port 125 can be located on the proximal end region 137 of the body 101. The access port 125 can be accessed by an intratympanic needle or similar device to refill the reservoir 115, for example. The reservoir need not be refilled following implantation. The distal end region 136 can be coupled to the intracochlear portion 105 such that a lumen 121 extending through the intracochlear portion can deliver the therapeutic agent 133 from the reservoir 115 into the inner ear. The lumen 121 can extend through the entire length of the intracochlear portion 105 such that the lumen 121 communicates on a proximal end with the reservoir 115 and on a distal end with the intracochlear space 132.

Since a substantial portion of the device 100 may reside within the tympanic cavity 30 post-implantation it can be beneficial to anchor the device in place for long term use. The intracochlear portion 105 can have a shape configured to aid in the retention of the device 100 within the medial wall 138 of the tympanic cavity 30. FIGS. 15A-15E illustrate various configurations of the intracochlear portion 105. In some implementations, the intracochlear portion 105 has a cone shape such that the proximal end region of the intracochlear portion 105 has a larger outer diameter than the distal end region of the intracochlear portion 105. The intracochlear portion 105 can also have a generally cylindrical shape such that the outer diameter of the proximal end region and distal end region are substantially the same (see FIG. 15E). In still further implementations, the intracochlear portion 105 can have a spool shape in which the middle portion is narrower than both the proximal end region and the distal end region of the intracochlear portion 105.

In addition, the intracochlear portion 105 can incorporate one or more retention features 139. Various retention features 139 configurations are contemplated herein. The retention features 139 can include threads such as self-tapping thread forms, flexible support members, sutures or suture holes, anchors or anchor holes, prongs, flanges, deflectable element, or an expandable feature like a stent or other deformable element configured to radially expand or change shape. The retention features 139 can be configured to engage with a region of a patient to fix the device 100 in place. In implementations, the retention features 139 can affix to a wall of the ear canal 40 or tympanic cavity 30, as described in more detail herein. Alternatively, the retention features 139 can be configured to anchor, engage or otherwise attach the device to the medial wall 138 separating the tympanic cavity 30 through an opening in the round window membrane 27. This opening can be created via cochleostomy 140, for example.

Figure 15H:
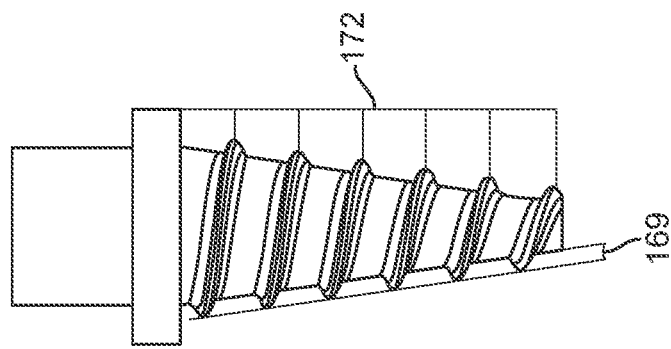
Figure 15G:
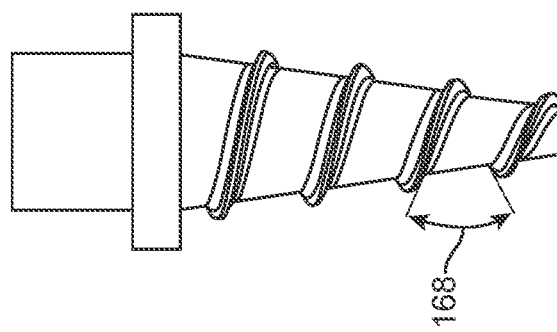
Figure 15F:
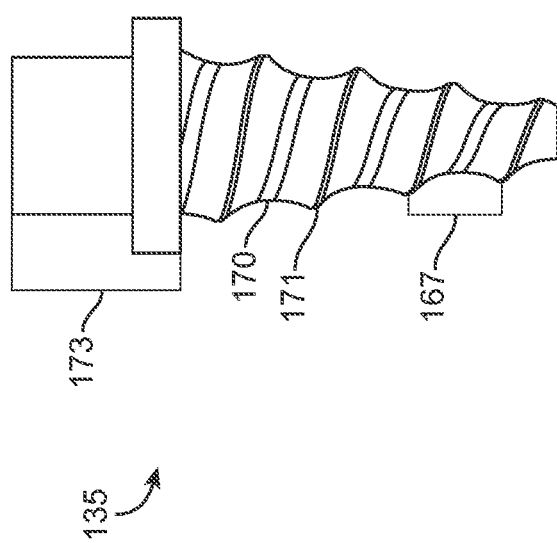

FIG. 14 illustrates an implementation of an intracochlear portion 105 having a retention feature 139 that is configured as a thread on the outer surface of the intracochlear portion 105. The threads can vary in their configuration as well (see FIGS. 15A-15C). The threads can have variable pitch 167, pitch angle 168, depth 169, root 170, crest 171, count 172, lead 173 and shape (see FIGS. 15F-15H) to secure the device and/or seal the cochleostomy. Any helical structure used to convert between rotational and linear movement or force may be incorporated on the intracochlear portion 105 to improve fixation. The retention feature 139 of the intracochlear portion 105 can also be barbed in various forms and configurations. It should also be appreciated that no separate retention feature 139 may be incorporated on the intracochlear portion 105 such that the shape of the intracochlear portion 105 alone is sufficient in fixing the device 100 in place.

The retention feature 139 can incorporate a self-tapping screw. The self-tapping screw can have a wide range of tip and thread patterns, but generally has a thread covering an entire length of the shaft from tip to head. The tip can be a corkscrew tip to engage the distal end of the screw into the bone. The self-tapping screw can allow for driving the screw into the bone without a pilot hole drilled into the bone, which can lead to leakage of perilymph. Further, the self-tapping screw can have a thread pattern designed to direct excavated bone material outward and away from the distal end of the screw.

Figure 16:
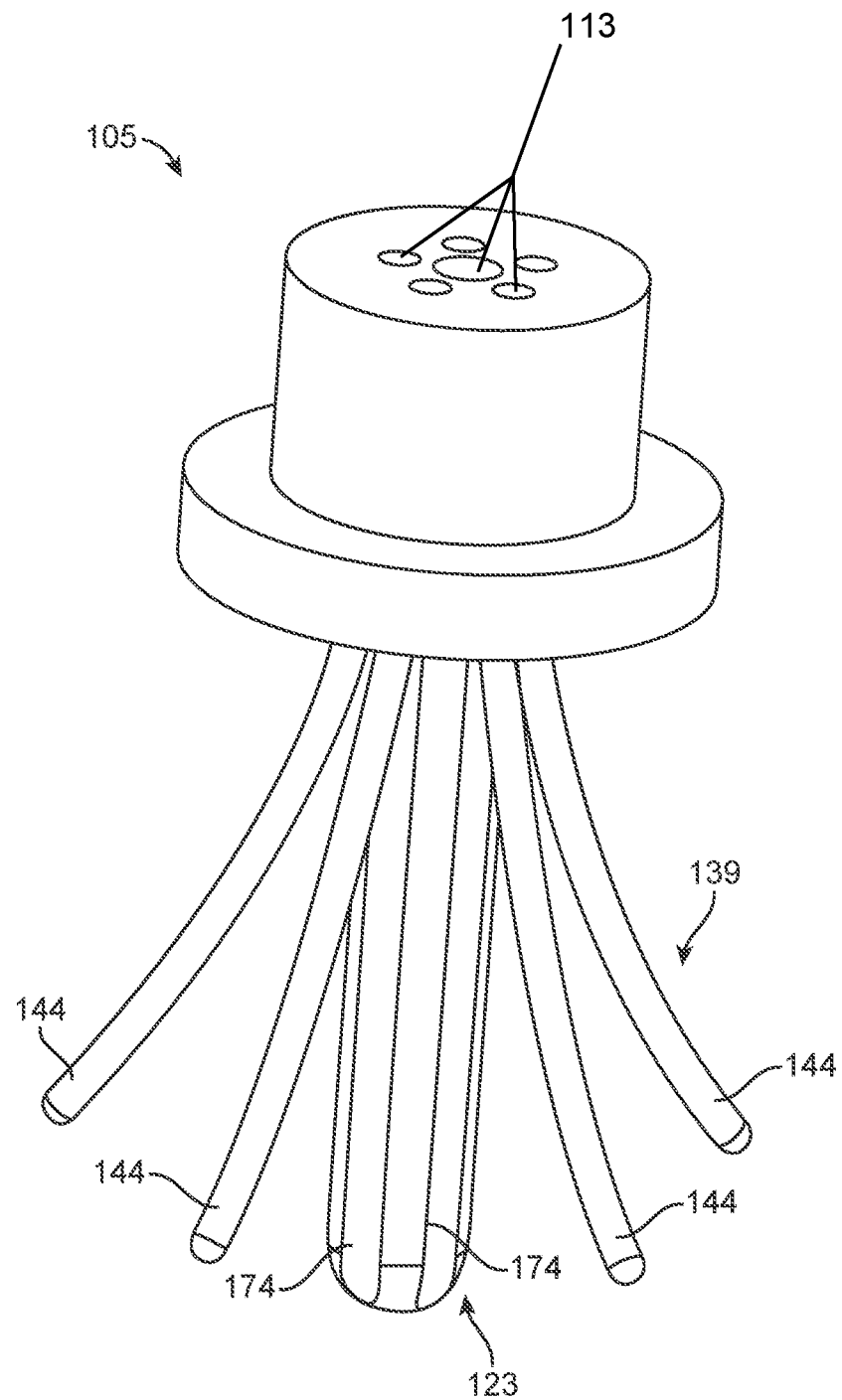
FIG. 16 shows an implementation of an implanted portion having a deformable anchoring feature.

FIG. 16 shows an implementation of an intracochlear portion 105 having retention features 139. In this implementation, the retention features 139 include one or more deformable prongs 144 configured to extend radially outward from a central longitudinal axis of the device or the longitudinal axis A of the shaft 123. In some implementations, the device includes a shaft 123 coaxial with the longitudinal axis of the device. The shaft 123 includes at least one lumen 121 extending from at least one inlet 113 on a proximal end of the shaft 123 to at least one outlet 117. The outlet 117 can be on a distal end of the shaft 123 or along at least a portion of the shaft 123 proximal to the distal end.

Figure 17A:
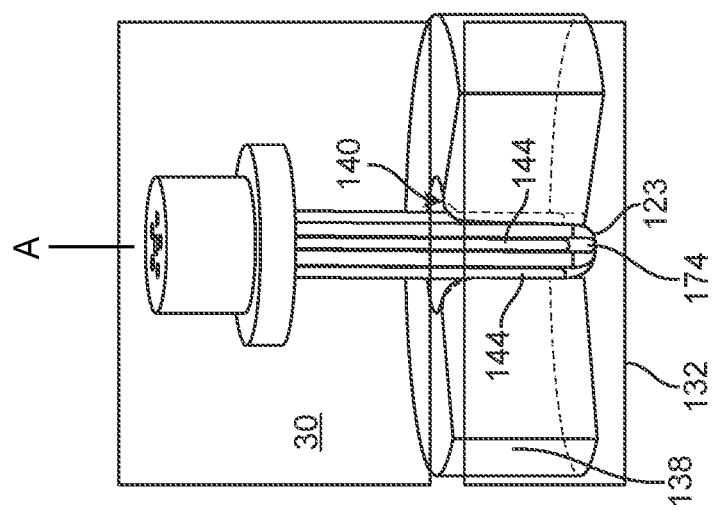
FIGS. 17A-17C show a method of deployment of the deformable anchoring feature of the implanted portion of FIG. 16 into the cochlear space as viewed from the side.
Figure 17B:
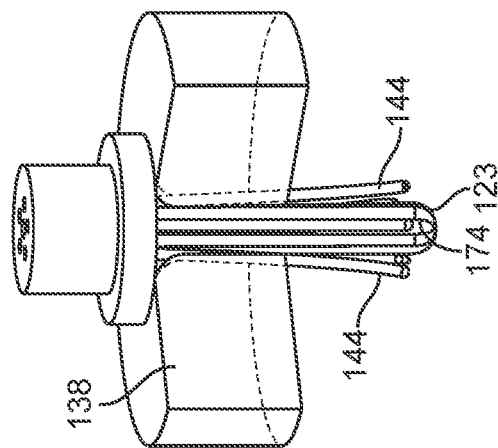
Figure 17C:
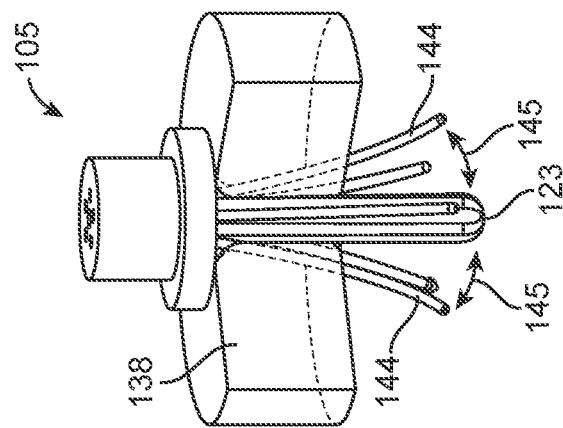

The retention feature 139 can include at least 1, 2, 3, 4, 5 or more deformable prongs 144 arranged symmetrically around the shaft 123. The prongs 144 can deform from a low-profile insertion configuration (i.e. constrained or undeployed) in which the prongs 144 are aligned with the central longitudinal axis of the device and an expanded deployed configuration in which the prongs 144 extend outward from the central longitudinal axis of the device. The shaft 123 can include one or more pockets 174 on its outer surface sized and shaped to receive each deformable prong(s) 144 when the retention feature 139 is in the undeployed (i.e. constrained) configuration (FIG. 17A). This allows for easier insertion through the medial wall 138 since the pockets 174 minimize the maximum outside diameter of the shaft 123 when the prongs 144 are positioned within the pockets 174. The prongs 144 can deform after the intracochlear portion 105 has been deployed through the cochleostomy. The deformable prongs 144 of the intracochlear portion 105 can be urged through the relatively narrow cochleostomy 140 with the prong(s) 144 in a folded or constrained configuration (FIG. 17A). The prong(s) 144 begin to deploy in a radial direction 145 (i.e. flare) from the shaft 123 of the intracochlear portion 105 as they become less constrained and the distal ends enter the cochlear space 132 (FIGS. 17C-17B). FIG. 17C depicts the prongs 144 fully deployed to prevent the reservoir (not shown in FIGS. 17A-17C) from detaching from the medial wall 138. The reservoir 115 may be attached to the intracochlear portion 105 during anchor deployment. The distal portion 136 of the rigid body 101 may be attached to the intracochlear portion 105 post anchor deployment. The prong(s) 144 may be formed of a shape memory material (SMM) or other similar material known to those of ordinary skill in the art.

Figure 18:
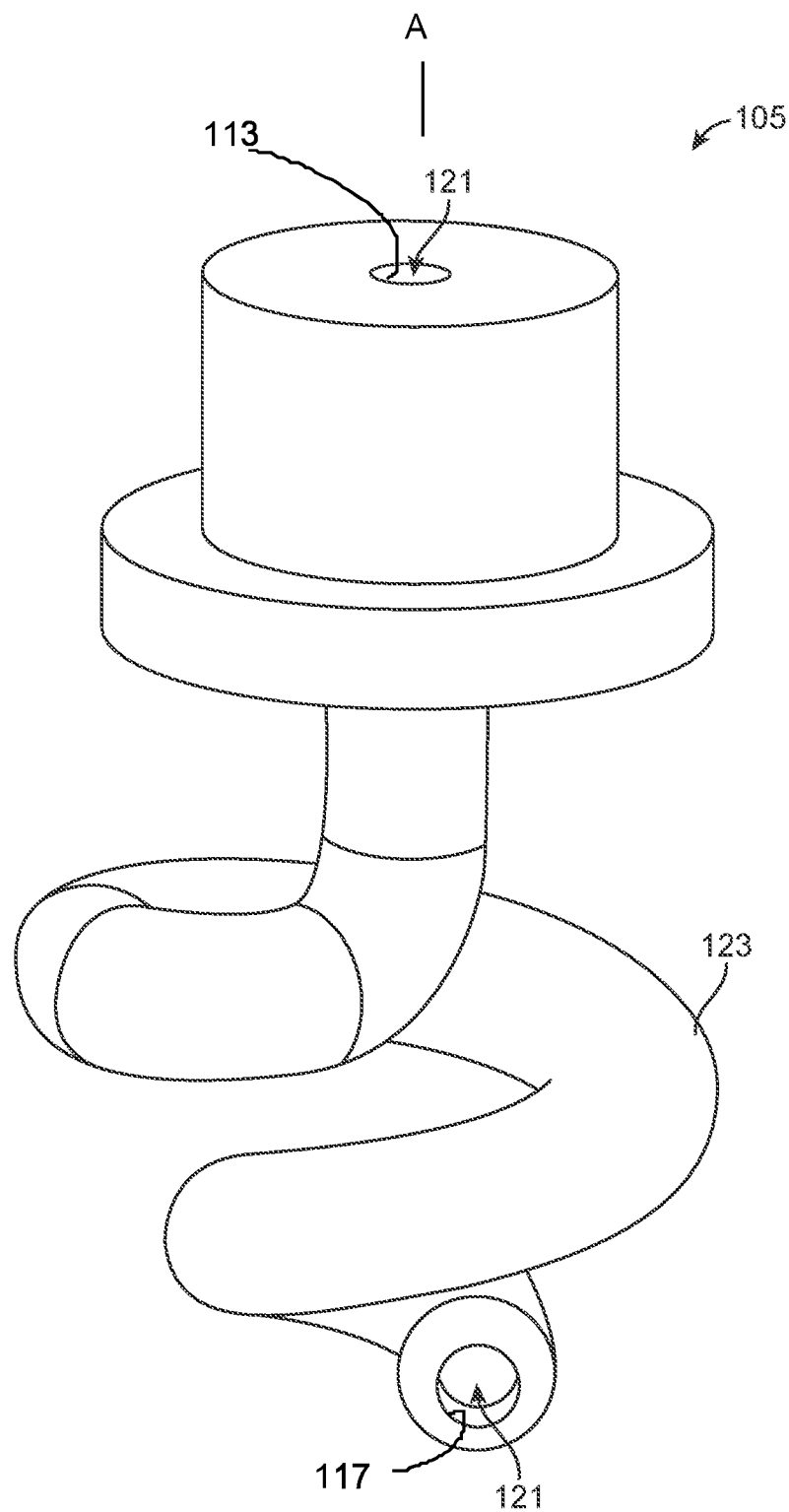
FIG. 18 shows an implementation of an implanted portion having a deformable anchoring feature.
Figure 19D:
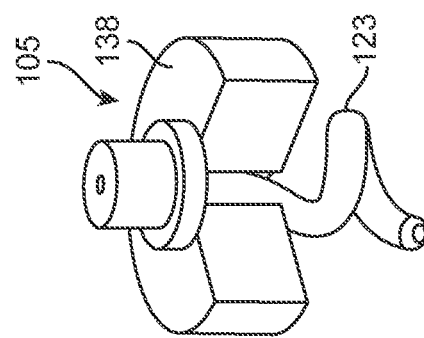
FIGS. 19A-19D show a method of deployment of the implanted portion of FIG. 18 deforming into the helical shape and into the cochlear space from a perspective view.
Figure 19C:
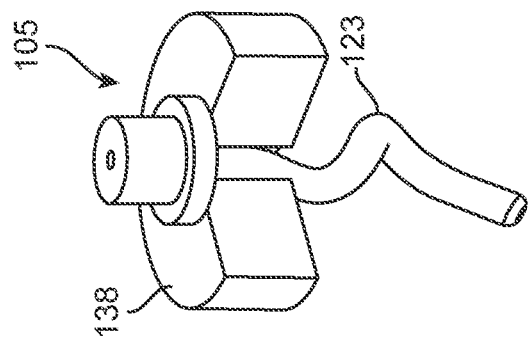
Figure 19B:
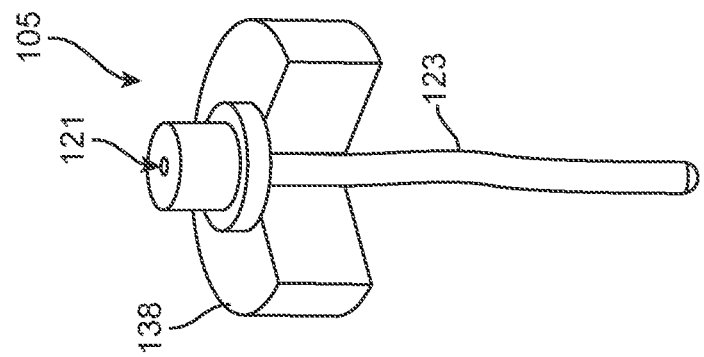
Figure 19A:
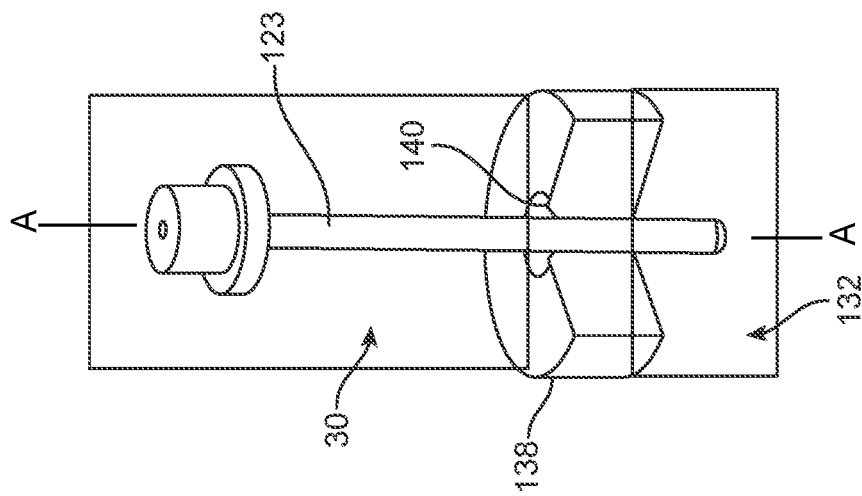

FIG. 18 shows an intracochlear portion 105 configured to change shape upon implantation to retain the device in place. The intracochlear portion 105 can change between a straight, insertion shape to a helical, deployed shape. The helical shape can be rigid or deformable and the outer diameter of the helix fills (i.e. seals) the cochleostomy 140 when the intracochlear portion 105 is inserted therethrough. The deployment is shown in sequence from the relatively rigid initial penetration of the intracochlear portion 105 through the cochleostomy while the intracochlear portion 105 has a straight, insertion configuration (FIG. 19A) to completed full deployment where the intracochlear portion 105 has achieved a full helical shape (FIG. 19D). The intracochlear portion 105 may be formed of a shape memory material (SMM) or other similar material commonly known to those of ordinary skill in the art. The material of the intracochlear portion 105 can achieve a final helical shape following implantation. The helical shape of the intracochlear portion 105 avoids excessive movement/migration of the device 100 and prevents the device from becoming dislodged. Similar to the intracochlear portion 105 shown in FIG. 14, the intracochlear portion 105 having a helical shape can include a central lumen 121 extending from a proximal end to a distal end. The lumen 121 allows for passive diffusion of the therapeutic agent 133 from the reservoir 115 to the inner ear 132. The helix of the intracochlear portion 105 can be straight such that a proximal end region of the helix and a distal end region of the helix have the same outer diameter. The helix of the intracochlear portion 105 can also be tapered such that the outer diameter of the distal end region of the helix is smaller than the outer diameter of the proximal end region of the helix. The tapering of the maximum outer dimension of the intracochlear portion 105 towards the distal end ensures the retention feature does not interfere significantly with the walls of the scala tympani (which narrow with distance from the round window membrane) while still providing an extended path length into which the drug is delivered.

A sheath or other tubular type structure can be used to retain the intracochlear portion 105 in the straight, insertion configuration. Upon removal of the sheath from the intracochlear portion 105, the intracochlear portion 105 (i.e. the prongs 144 of FIG. 16 or the helix or FIG. 18) is released to undergo shape change to their respective deployed shape. In the implementation shown in FIG. 16, the outer sheath can be used in lieu of the shaft 123 and provide enough rigidity up to the cochleostomy. To transition from the straight insertion configuration to the deployed configuration, the sheath may be withdrawn proximally and/or the device may be advanced distally as is known in the art.

Figure 20:
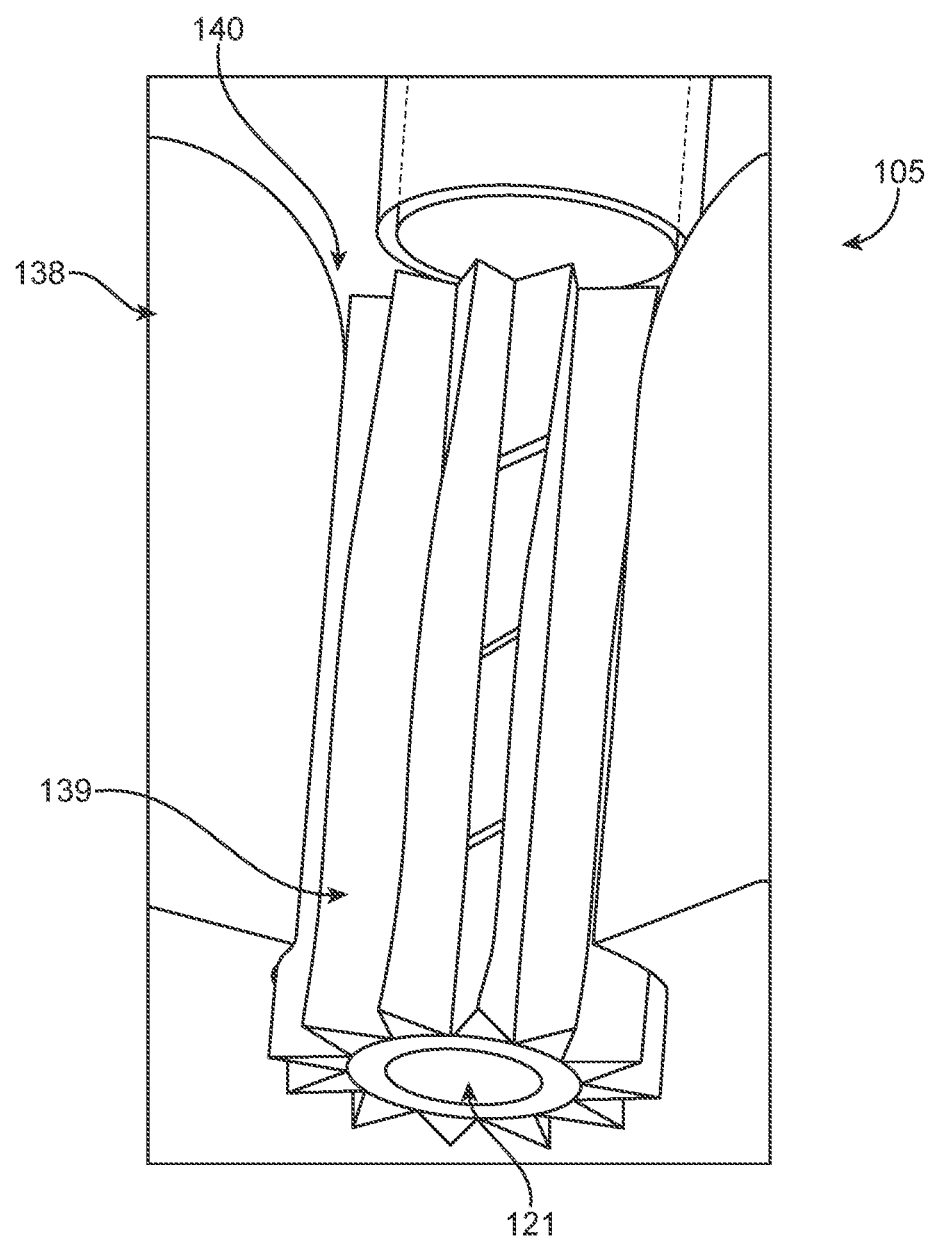
FIG. 20 shows an implementation of a implanted portion having deformable anchoring features.

FIG. 20 shows an implementation of an intracochlear portion 105 having retention features 139 configured to hold the device 100 in the tympanic cavity 30 via anchoring through and substantially sealing a cochleostomy or similar opening in the medial wall 138 separating the tympanic cavity 30 from the inner ear or intracochlear space 132. Similar to the intracochlear portion 105 shown in FIG. 14, the intracochlear portion 105 of FIG. 20 can have an outer surface having compliant, deformable retention features 139 and a central lumen 121 that allows for passive diffusion of the therapeutic agent 133 from the reservoir 115 to the inner ear 132. The retention features 139 may form a plurality of radially-extending, deformable flanges providing a maximum outer dimension to the intracochlear portion 105. Deflection of the retention features 139 can reduce the outer dimension of the intracochlear portion 105. The deformable retention features 139 can be deflected to the reduced outer dimension during implantation through the cochleostomy 140, such as using an insertion tool 148 (see FIG. 21A-21B) configured to constrain the deformable retention features 139 around the central axis of the intracochlear portion 105. The deformable retention features 139 can return to the maximum outer dimension upon release from a constraint, such as upon removal of the insertion tool 148 following deployment. The region of the retention features 139 positioned within the cochleostomy 140 can maintain the constrained outer diameter even upon release from the insertion tool 148, whereas regions of the retention features 139 positioned outside the cochleostomy 140 (e.g. proximal to and/or distal to) can return towards their maximum outer dimension providing sealing fixation of the intracochlear portion 105 within the cochleostomy 140. The intracochlear portion 105 can be generally cylindrical in cross-section such that the constrained outer diameter approximates the inner diameter of the cochleostomy. The maximum outer dimension (i.e. the cross-sectional diameter of the intracochlear portion 105 when the retention features 139 are in an unbiased configuration) can be slightly oversized with respect to the cochleostomy 140 to provide better sealing upon insertion. In some implementations, the maximum cross-sectional dimension can be less than about 5 mm, less than about 4 mm, less than about 3 mm, less than about 2 mm, down to about 0.2 mm maximum cross-sectional outer diameter. The retention features 139 may be made of silicon, rubber, or any other pliable material known by those of skill in the art that allows for deflection between the constrained state and the deployed state. The deformable retention features 139 can provide a cross-sectional shape to the intracochlear portion 105 that is cross-shaped, gear-shaped, star-shaped, and the like. Thus, each flange of the retention features 139 can have a triangular shape, a cone shape, a circular shape, a semi-circular shape, or other shape projecting away from the central axis of the lumen 121 extending through the intracochlear portion 105. In an implementation, each deformable flange can have a triangular cross-sectional shape, where the cross-section is taken along a plane perpendicular to the longitudinal axis of the lumen 121 extending through the intracochlear portion 105. Thus, the base of each flange can be wider than the apex of each flange. In another implementation, each deformable flange can have a polygonal cross-sectional shape, such as rectangular, square, or other polygonal shape. Each of the retention features 139 can be pliable so as to be pressed together and/or against the inner cylinder shape of the intracochlear portion 105 during deployment and open into a less constrained state pre- or post-deployment (e.g. on either side of the medial wall 138), for example (see FIGS. 20, and 21A-21D).

Figure 21:
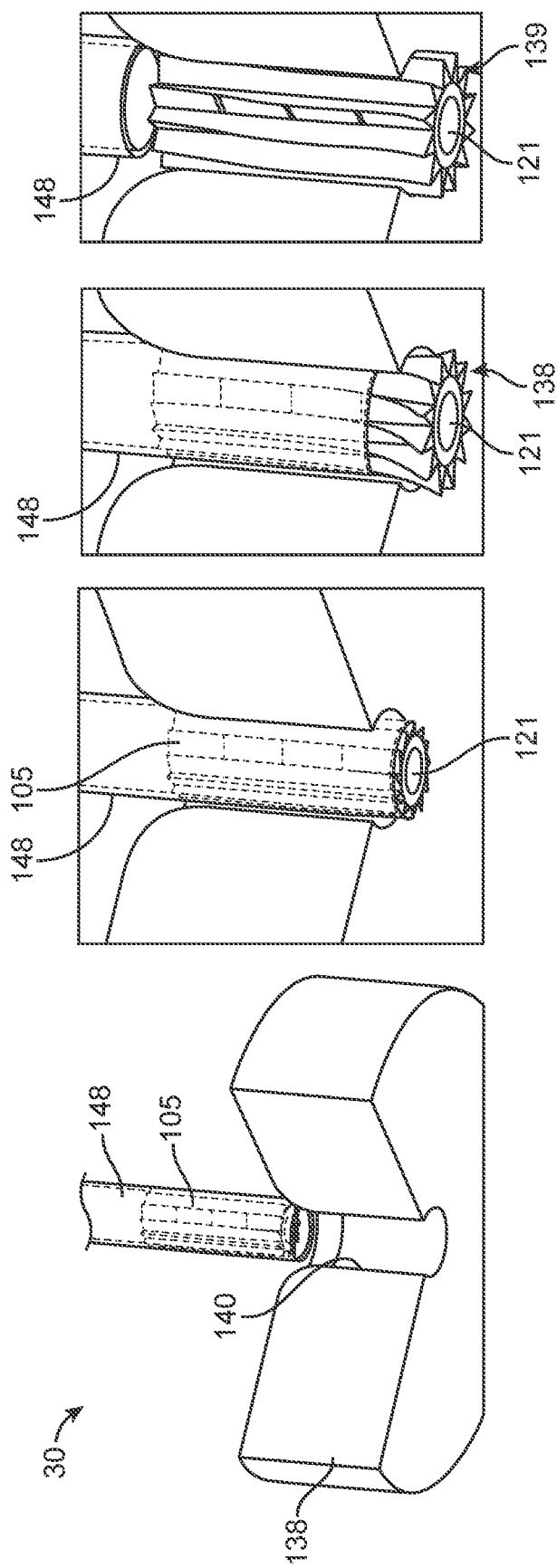
FIGS. 21A-21D show a method of deployment of the implanted portion of FIG. 20 into the cochlear space from a perspective view.

FIGS. 21A-21D show a method of deployment of a compliant intracochlear portion 105 of FIG. 20 at least partially into the cochlear space 132 from a perspective view. An introducer tool 148 can be used to position the intracochlear portion 105 having compliant retention features 139 through the opening of the cochleostomy 140. As the compliant deflectable retention features 139 extend beyond the cochleostomy 140 into the intracochlear space, the retention features 139 begin to unfold. The unfolding can be radial clockwise or counter clockwise or any other means to substantially seal the cochleostomy and anchor the device. The introducer tool 148 can be removed at this point (FIG. 21C). In some implementations, the body 101 defining the reservoir 115 can be later assembled with the intracochlear portion 105 following implantation. In some implementations, the body 101 defining the reservoir 115 can be coupled to the intracochlear portion 105 such that the device has a unitary or monolithic structure. In this implementation, the reservoir 115 may be collapsed and contained within a lumen of the introducer tool 148 during implantation of the intracochlear portion 105.

FIGS. 22 and 23 illustrate another implementation of a drug delivery device 100. The drug delivery device 100 includes a reservoir 115 in fluid communication with a shaft 123 having a lumen 121 extending from a proximal end of the shaft 123 to a distal end of the shaft 123. The reservoir 115 formed of a distensible material and is configured to remain outside the cochlea (i.e. within the middle ear). The walls of the reservoir 115 can be rigid or compliant. The device 100 can include a drug release element configured to passively control diffusion of a drug out of the reservoir 115 as described elsewhere herein. In an implementation, the drug release element 110 is positioned on a proximal end of the shaft 123 such that diffusion of drug into the lumen 121 is controlled. The drug release element 110 can also be positioned within the lumen 121 of the shaft 123 or at a distal end of outlet from the lumen 121 such that the drug release element 110 controls the diffusion of drug out of the lumen 121. A proximal end region of the shaft 123 can have a plurality of openings one or more of which have a drug release element 110 positioned therein. The plurality of openings can be positioned on a proximal-facing surface of the shaft 123 and/or on through a sidewall of the shaft 123 (see FIG. 23). Any of a variety of configurations are considered herein. Although the lumen 121 is shown substantially aligned with the longitudinal axis of the shaft, the internal lumen 121 may also be positioned eccentrically.

The device 100 can align with and be substantially symmetrical around a central axis A. Alternatively, the device 100 can be asymmetrical with respect to the central axis A. For example, the reservoir 115 can have a first portion that is substantially greater than a second portion where the first portion is positioned eccentric to an insertion axis of the device. Any of a variety of shapes of the reservoir 115 are considered herein depending upon the implantation location, angle, and arrangement relative to the surrounding anatomy. The reservoir 115 can be configured to be refilled as described elsewhere herein.

Still with respect to FIGS. 22 and 23, the device 100 may be retained in place by a mounting plate 142. The mounting plate 142 can be used to retain the reservoir 115 in the tympanic cavity 30 by securing the mounting plate 142 to the medial wall 138 separating the tympanic cavity 30. The mounting plate 142 can be secured to tissue using glue, sutures, or a variety of other means commonly known and understood by those of ordinary skill in the art. In an implementation, a perimeter region of the mounting plate 142 can have one or more retention features 139 such as suture anchor holes extending through the perimeter region of the mounting plate 142 configured to receive one or more sutures to affix the device into place. The mounting plate 142 can be separable from the device. The mounting plate 142 can have an inner bore 141 configured to receive and substantially surround the shaft 123. In some implementations, the inner bore 141 of the mounting plate 142 aligns with a central axis of the device or an insertion axis of the shaft 123.

FIGS. 22 and 23 show the shaft 123 has a beveled, needle-like tip configured to penetrate tissue. The outside surface of the shaft 123 is shown as being smooth. The outside surface of the shaft 123 can also incorporate one or more retention elements 139 as described elsewhere herein. For example, the shaft 123 may incorporate a thread pattern such as a helical, self-tapping thread such that the shaft 123 may cut through and linearly advance or penetrate bone upon rotation around the central axis A and without drilling a pilot hole through the medial wall 138. In some implementations, the shaft 123 has a self-tapping thread pattern on its outer surface and no mounting plate 142. The shaft 123 may have a length sufficient to sit deep enough into the cochlea for the lumen 121 to be exposed. The shaft 123 can be configured to substantially anchor as well as seal the device within the wall through which it extends. The shaft 123 can be tapered distally. A longitudinal axis of the shaft 123 can be coaxial with a longitudinal axis A of the device. The internal lumen 121 extending through the shaft 123 can have a longitudinal axis, which can be aligned or off-set from the longitudinal axis A of the shaft 123. As described elsewhere herein the lumen 121 extending through the shaft 123 can include at least one inlet 113 at a proximal end region of the shaft 123 in fluid communication with the reservoir 115 and at least one outlet 117 at a distal end region of the shaft 123 such that when the body 101 is implanted in a cavity. The at least one inlet 113 can include a plurality of inlets 113 configured to be in fluid communication with the reservoir 115. One or more of the inlets 113 can incorporate a porous drug release element 110 positioned within the inlet 113 (see FIG. 22). One or more of the inlets 113 can be positioned in an upper surface at the proximal end of the shaft 123 and/or through a sidewall of the proximal end region of the shaft 123 (see FIG. 23). At least a portion of the shaft 123 can extend through the wall of the cavity and the at least one outlet 117 is positioned into a cochlear space. The cavity can include the tympanic cavity or the mastoid cavity. In some implementations, the cavity is the tympanic cavity and the wall is the medial wall 138 of the tympanic cavity 30. The device can further include a porous drug release element 110 positioned relative to at least one of the inlet 113 and the outlet 117 from the lumen 121 of the shaft 123.

Figure 24D:
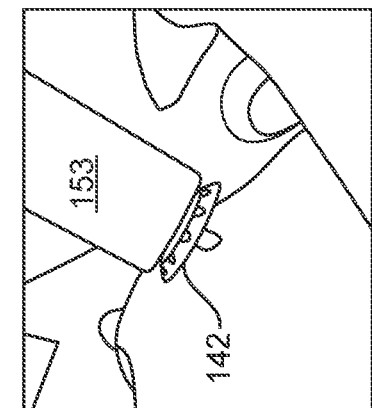
FIGS. 24A-24H show a method of deployment of a drug delivery device with a separable mounting plate.
Figure 24E:
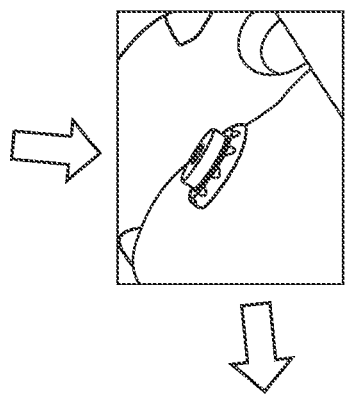
Figure 24C:
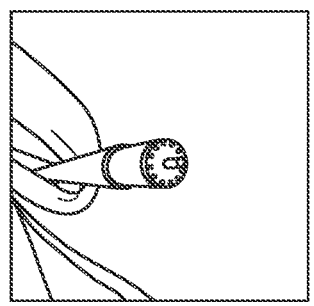
Figure 24F:
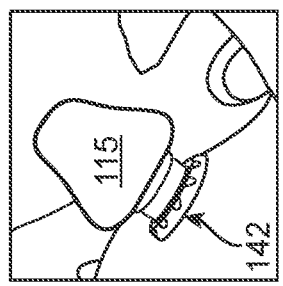
Figure 24B:
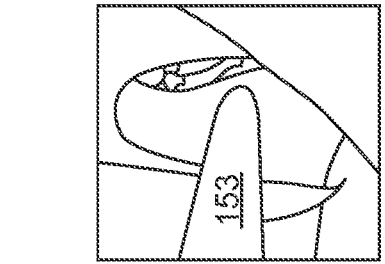
Figure 24G:
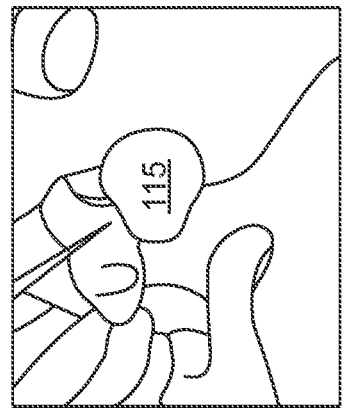
Figure 24A:
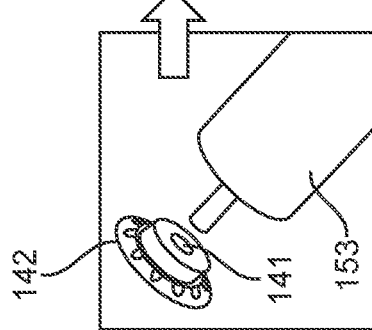
Figure 24H:
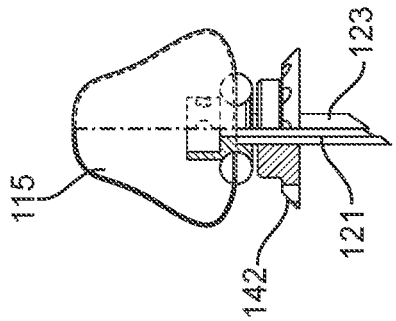

As mentioned above, the device can be assembled at the time of implantation. The mounting plate 142 can be first held by an insertion tool 153 (see FIG. 24A). In an implementation, the insertion tool 153 can have a distal holding element configured to be received within the inner bore 141 of the mounting plate 142. The insertion tool 153 having the mounting plate 142 held by the distal holding element can be guided down the ear canal 40 (FIG. 24B) and passed through the tympanic membrane 5 (i.e. via a tympomeatal flap) (FIG. 24C). The mounting plate 142 can be delivered to a wall 138 of the middle ear (FIG. 24D). The mounting plate 142 can be secured in place with adhesive, sutures or similar means and the insertion tool 153 can be removed from the ear canal 40 (FIG. 24E). A cochleostomy hole 140 can then be created using inner bore 141 of the mounting plate 142 as a guide (FIG. 24E). The implant body 101 defining the reservoir 115 can be then guided toward the cochleostomy 140 and affixed to the mounting plate 142 (FIG. 24F). FIG. 24G is a perspective view of the implanted device 100 secured in place as seen in the tympanic cavity 30.

Figure 25:
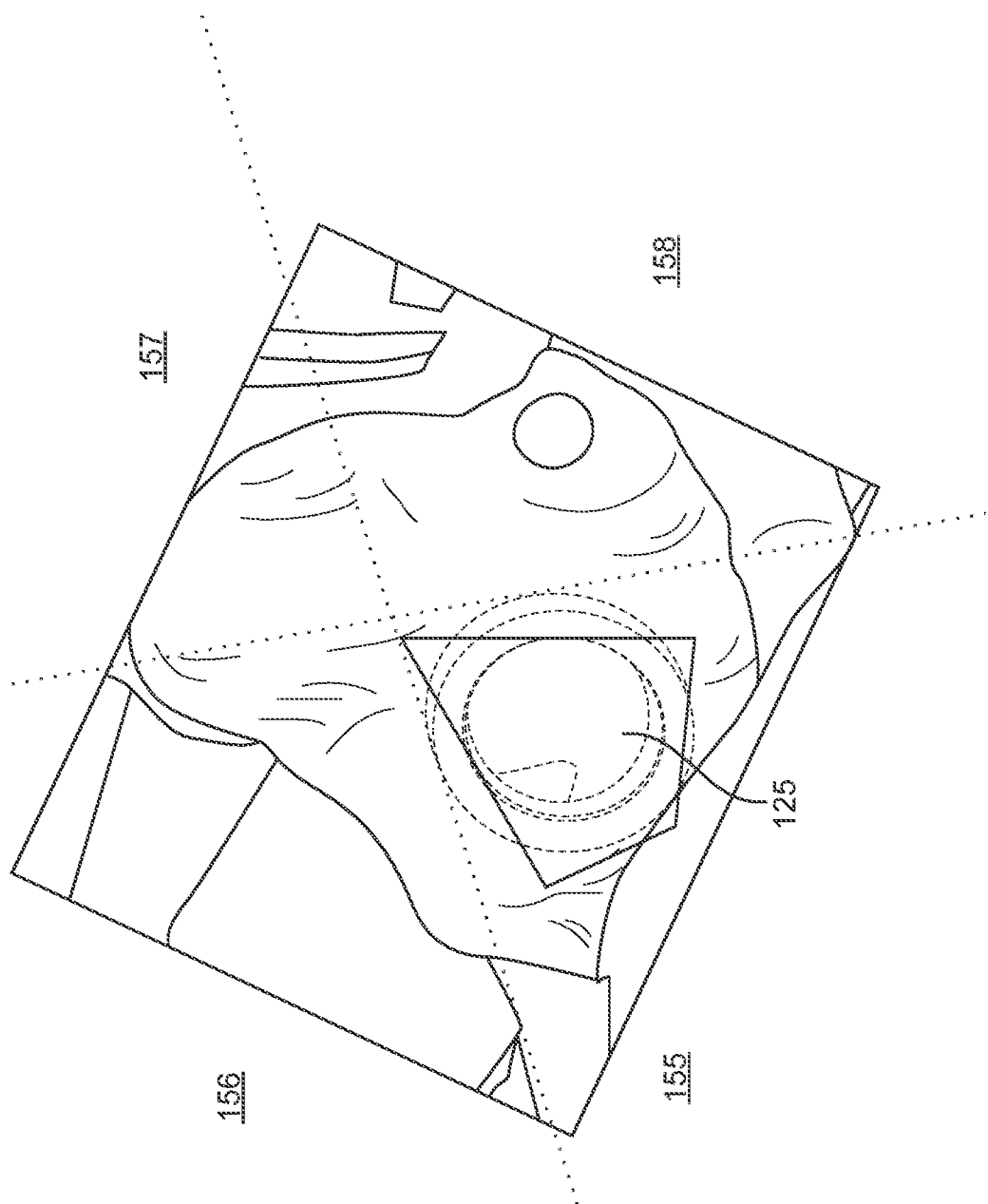
FIG. 25 shows a drug delivery device positioned on the medial wall of the middle ear.

FIG. 25 shows the drug delivery device of FIG. 23 positioned on the medial wall 138 of the middle ear behind the anterior inferior quadrant 155 of the tympanic membrane 5 with reference to other quadrants including the anterior superior quadrant 156, the posterior superior quadrant 157, and the posterior inferior quadrant 158. All quadrants correspond to the left ear. The injection site for filling and refilling the reservoir 115 with the therapeutic agent is shown in anterior inferior quadrant 155. This placement allows for preferred targeting with a transtympanic needle through the anterior inferior quadrant 155 of the tympanic membrane 5.

Figure 26:
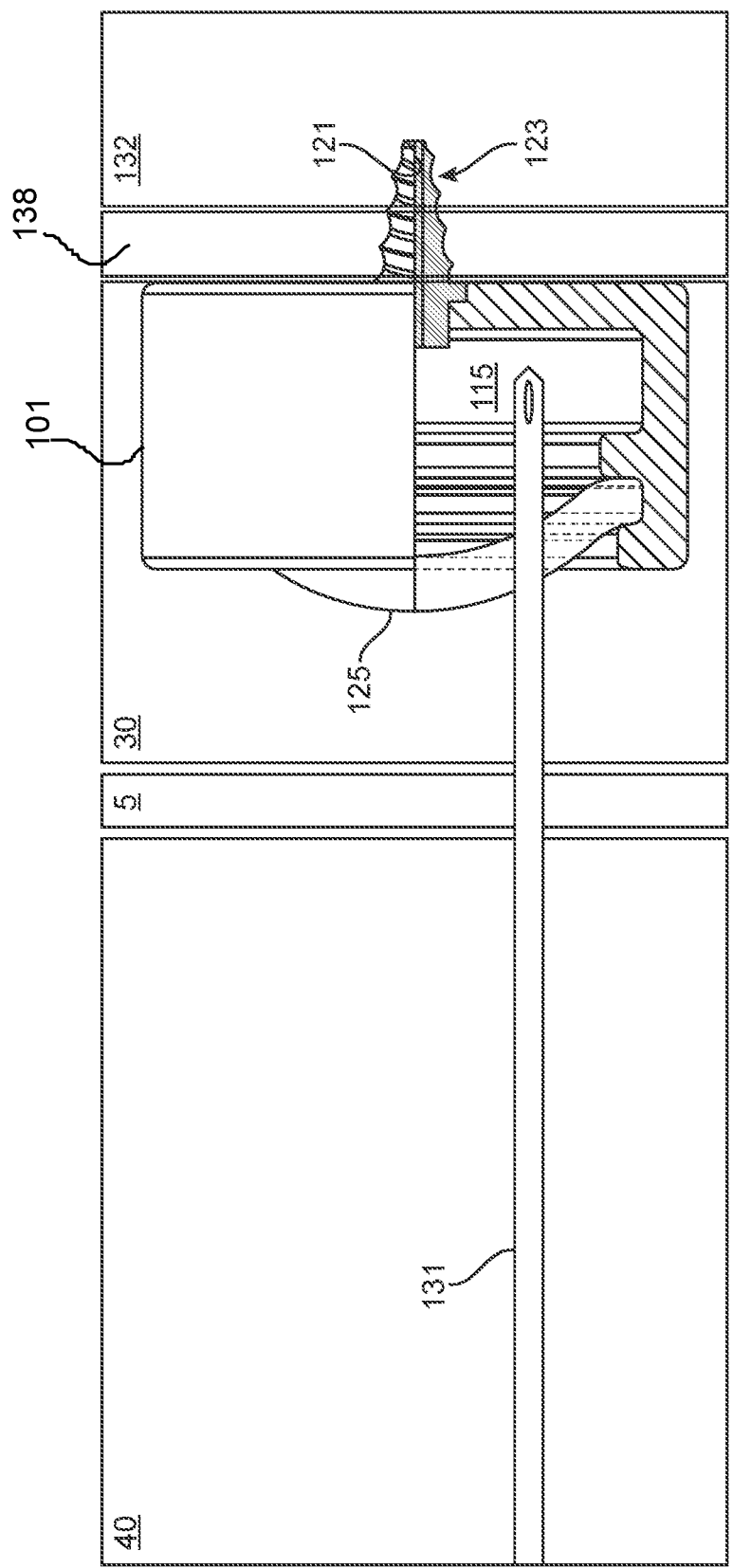
FIG. 26 shows an implementation of a trans-tympanic needle accessing the drug delivery device of FIG. 14.

FIG. 26 shows an implementation of a trans-tympanic needle 131 accessing the drug delivery device of FIG. 14 including piercing the puncturable access port 125 to conveniently fill or refill the reservoir 115 with therapeutic agent without the need to remove the implanted device from the ear. The contents of the reservoir can also be sampled or evacuated using this method of access. The needle 131 may have a single lumen for dispensing the therapeutic agent into the reservoir. In some implementations, the needle can be a dual lumen needle, two or more needles positioned substantially alongside one another, or openings positioned along the length of a single needle. These and other similar configurations serve as a vent to relieve (i.e. decrease) fluid pressure in the reservoir during filing by taking up extra fluid and also avoids accidental over filling the reservoir, for example.

Generally, the implementations of the treatment devices described herein contain drug solutions, drug suspensions and/or drug matrices. The treatment devices described herein can also contain therapeutic agents formulated as one or more solid drug core or pellets formulated to deliver the one or more therapeutic agents at therapeutically effective amounts for an extended period of time. The period of time over which the treatment device delivers therapeutically effective amounts can vary. Drug diffusion rates in the inner ear are determined by various factors, such as molecular size, configuration, concentration, liposolubility and electrical charge of the drug, for example. A few examples of drugs that may be used in the middle and inner ear include methotrexate, gentamicin, aminoglycosides and steroids. This list of drugs is not intended to be comprehensive. Other known drugs and developmental drugs may also provide beneficial treatment to the ear. In some implementations, the treatment device can be implanted to provide a therapy over the effective life of the device such that refilling the device is not necessary.

The treatment devices described herein can be used to treat and/or prevent a variety of other conditions, including but not limited to hearing loss, including hidden hearing loss, noise-induced hearing loss, age-related hearing loss, drug-induced hearing loss, such as chemotherapy-induced hearing loss or aminoglycoside-induced hearing loss, sudden sensorineural hearing loss, and the like. Any of a variety of ear disorders can be treated using the devices described herein. The treatment devices described herein can be used to treat other ear disorders such as tinnitus. The treatment devices described herein can be used to treat balance disorders including vertigo, Meniere's disease, vestibular neuronitis, labyrinthitis, and the like.

Examples of therapeutic agents that may be delivered by the treatment devices described herein and/or are described in the applications incorporated by reference herein are provided below.

Therapeutics that can be delivered from the devices described herein include but are not limited to antioxidants, anti-inflammatories, corticosteroids, steroids, aminoglycosides, antimicrobials, NMDA receptor antagonists, nootropics, anti-apoptotic agents, neurotrophins, neuroprotective agents, neural protective proteins such as ciliary neurotrophic factor (CNTF), brain-derived neurotrophic factor (BDNF), pigment epithelium-derived factor (PEDF), nerve growth factor (NGF), and the like, cannabinoids, monoclonal antibodies, other proteins, gene therapy, iRNA, cell therapies, and protein therapies like anti-VEGF.

As an example, the therapeutic agent can include, but is not necessarily limited to, antimicrobials such as antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluoromethalone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors; antioxidants, N-methyl-D-aspartate (NMDA) receptor antagonists, nootropics, anti-apoptotic agents, neurotrophins, neuroprotective agents, cannabinoids, monoclonal antibodies, other proteins, cell therapies, and gene therapy. Other therapeutic agents known to those skilled in the art which are capable of controlled, sustained release into the ear in the manner described herein are also suitable for use in accordance with implementations or features of the devices described herein.

The therapeutic agent can include, but is not limited to, sodium thiosulfate to protect against cisplatin-induced hearing loss; NMDA receptor antagonists for the treatment of tinnitus (AM-101; Auris Medical); AM-111 containing the synthetic peptide D-JNKI-1 (D-stereoisomer of c-Jun N-terminal Kinase Inhibitor 1; Auris Medical) for otoprotection in acute inner ear hearing loss; dexamethasone for the treatment of Meniere's Disease; D-methionine (Southern Illinois University) to protect against Noise-induced hearing loss; LY411575 (a selective gamma secretase inhibitor that blocks Notch activation); NT-3 neurotrophic factor; and APAF-1 inhibitors such as those described in U.S. Pat. No. 9,040,701, which is incorporated by reference here in its entirety.

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols including P407 and other combinations of polyethylene glycol and polypropylene glycol; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, cyclodextrins, polyoxyethylene stearate and the like. The carrier may also contain adjuvants such as preserving, stabilizing, wetting, colorizing, odorizing, emulsifying agents or other related materials.

While this specification contains many specifics, these should not be construed as limitations on the scope of what is claimed or of what may be claimed, but rather as descriptions of features specific to particular implementations or features. Certain features that are described in this specification in the context of separate embodiments can also be implemented in combination in a single implementation or feature. Conversely, various features that are described in the context of a single implementation or feature can also be implemented in multiple implementations or features separately or in any suitable sub-combination. Moreover, although features may be described above as acting in certain combinations and even initially claimed as such, one or more features from a claimed combination can, in some cases, be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed. The claimed subject matter has been described in conjunction with the detailed description thereof, the foregoing description is intended to illustrate and not limit the scope of the claimed subject matter of the appended claims.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of the devices and/or delivery systems to a specific configuration described in the various implementations.

Unless otherwise indicated, all numbers expressing dimensions, quantities, properties, and so forth used in the specification and claims are to be understood as being modified in instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the devices and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements, embodiments, or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An implantable device for delivering a therapeutic agent to treat an ear of a patient, the device comprising:
   a body having a distal end region and a proximal end region, wherein the body defines, at least in part, a reservoir configured to contain the therapeutic agent;
   a shaft attached to the distal end region of the body and comprising a lumen extending through the shaft, the lumen having at least one inlet at a proximal end region of the shaft in fluid communication with the reservoir and at least one outlet at a distal end region of the shaft, the shaft having a length between the proximal end region of the shaft and the distal end region of the shaft; and
   an annular anchor comprising:
      an outer ring surface configured to seal against a perimeter of a round window membrane and an inner ring surface;
      a first distensible membrane coupled to a proximal side of the annular anchor;
      a second distensible membrane coupled to a distal side of the annular anchor opposite the first distensible membrane, wherein the first distensible membrane is non-permeable to the therapeutic agent and the second distensible membrane is permeable to the therapeutic agent; and
      a chamber located within the annular anchor and defined collectively by the inner ring surface, an inner surface of the first distensible membrane, and an inner surface of the second distensible membrane,
   wherein, upon implantation of the body in a region of the ear, the length of the shaft is sufficient to extend from the body to at least the round window membrane of the ear, and
   wherein the device is configured to deliver the therapeutic agent to the ear from the reservoir via passive diffusion.

2. The implantable device of claim 1, wherein the body is sized to be implanted in a tympanic cavity or in a mastoid cavity of a middle ear of the patient.

3. The implantable device of claim 1, wherein the body is sized to be implanted in an ear canal of the patient.

4. The implantable device of claim 1, wherein the reservoir has a volume of about 5 uL to about 1 mL.

5. The implantable device of claim 1, further comprising an access port into the reservoir.

6. The implantable device of claim 5, wherein a resealable penetrable barrier is positioned within the access port that is configured to be penetrated for refilling of the reservoir with therapeutic agent.

7. The implantable device of claim 1, wherein the body is rigid.

8. The implantable device of claim 1, wherein the body is compliant.

9. The implantable device of claim 1, wherein the therapeutic agent is selected from the group consisting of corticosteroids, aminoglycosides, antimicrobials, antifungals, antivirals, non-steroidal anti-inflammatories, decongestants, anticholinesterases, mydriatics, sypathomimetics, antineoplastics, immunological drugs, hormonal agents, beta adrenergic blockers, growth factors, anhysrase inhibitors, prostaglandins, antiprostaglandins, prostaglandin precursors, antioxidants, NMDA receptor antagonists, nootropics, anti-apoptotic agents, neurotrophins, neuroprotective agents, cannabinoids, monoclonal antibodies, gene therapies, cell therapies, and inhibitors of APAF-1.

10. The implantable device of claim 1, wherein the annular anchor is formed of a conformable material.

11. The implantable device of claim 1, wherein the annular anchor is formed of a semi-rigid material.

12. The implantable device of claim 1, wherein the at least one outlet at the distal end region of the shaft is in fluid communication with the chamber.

13. The implantable device of claim 1, wherein passive diffusion of the therapeutic agent comprises passive diffusion through the second distensible membrane.

* * * * *